(12) United States Patent
Neufeld et al.

(10) Patent No.: US 8,513,194 B2
(45) Date of Patent: Aug. 20, 2013

(54) COMPOSITIONS COMPRISING SEMAPHORINS FOR THE TREATMENT OF ANGIOGENESIS RELATED DISEASES AND METHODS OF SELECTION THEREOF

(75) Inventors: Gera Neufeld, Haifa (IL); Boaz Kigel, Kiryat-Tivon (IL); Ofra Kessler, Haifa (IL); Asya Varshavsky, Haifa (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 0 days.

(21) Appl. No.: 13/313,063

(22) Filed: Dec. 7, 2011

(65) Prior Publication Data

US 2012/0101029 A1 Apr. 26, 2012

Related U.S. Application Data

(62) Division of application No. 12/738,634, filed as application No. PCT/IL2008/001307 on Oct. 2, 2008, now Pat. No. 8,088,735.

(60) Provisional application No. 60/960,910, filed on Oct. 19, 2007, provisional application No. 61/006,496, filed on Jan. 16, 2008, provisional application No. 61/071,053, filed on Apr. 10, 2008, provisional application No. 61/071,560, filed on May 6, 2008.

(51) Int. Cl.
*A61K 38/16* (2006.01)
*A61K 38/17* (2006.01)
*C07K 14/435* (2006.01)

(52) U.S. Cl.
USPC ........... 514/13.3; 514/19.3; 514/1.1; 530/350

(58) Field of Classification Search
None
See application file for complete search history.

(56) References Cited

U.S. PATENT DOCUMENTS

| 2003/0113324 A1 | 6/2003 | Alitalo et al. |
| 2007/0105133 A1 | 5/2007 | Clarke et al. |
| 2010/0247516 A1 | 9/2010 | Neufeld et al. |

FOREIGN PATENT DOCUMENTS

| WO | WO 2004/006898 | 1/2004 |
| WO | WO 2007/056470 | 5/2007 |
| WO | WO 2009/050691 | 4/2009 |
| WO | WO 2009/089461 | 7/2009 |
| WO | WO 2011/138449 | 11/2011 |

OTHER PUBLICATIONS

Benouchan et al. (2005). Anti-angiogenic strategies for cancer therapy (review). Intl. J. Oncology. 27:563-571.*
Shumizu et al. (2005). Antineovascular therapy, a novel antiangiogenic approach. Expert. Opin. Ther. Targets. 9(1):63-76.*
Neri et al. (2005). Tumour vascular targeting. Nature Reviews Cancer. 5:436-446.*
Eskens, F. (2004). Angiogenesis inhibitors in clinical development; where are we now and where are we going? British Journal of Cancer. 90:1-7.*
Sweeney et al. (2003). Resistance in the anti-angiogenic era: naysaying or a word of caution? Trends in Molecular Medicine. 9(1):24-29.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Office Action Dated Jan. 8, 2012 From the Israel Patent Office Re. Application No. 205061 and Its Translation Into English.
Communication Pursuant to Rules 70(2) and 70a(2) EPC Dated Sep. 22, 2011 From the European Patent Office Re. Application No. 08808106.2.
European Search Report and the European Search Opinion Dated Sep. 5, 2011 From the European Patent Office Re. Application No. 08808106.2.
International Preliminary Report on Patentability Dated Apr. 29, 2010 From the International Bureau of WIPO Re.: Application No. PCT/IL2008/001307.
International Search Report Dated May 28, 2009 From the International Searching Authority Re.: Application No. PCT/IL08/01307.
Notice of Allowance Dated Aug. 31, 2011 From the US Patent and Trademark Office Re. U.S. Appl. No. 12/738,634.
Official Action Dated Dec. 23, 2010 From the US Patent and Trademark Office Re. U.S. Appl. No. 12/738,634.
Official Action Dated Mar. 30, 2011 From the US Patent and Trademark Office Re. U.S. Appl. No. 12/738,634.
Response Dated Jan. 24, 2011 to Official Action of Dec. 23, 2010 From the US Patent and Trademark Office Re. U.S. Appl. No. 12/738,634.
Response Dated Jun. 30, 2011 to Official Action of Mar. 30, 2011 From the US Patent and Trademark Office Re. U.S. Appl. No. 12/738,634.
Written Opinion Dated May 28, 2009 From the International Searching Authority Re.: Application No. PCT/IL08/01307.
Banu et al. "Semaphorin 3C Regulates Endothelial Cell Function by Increasing Integrin Activity", The FASEB Journal, 20: 2150-2152, 2006. Abstract.
Bielenberg et al. "Neuropilins in Neoplasms: Expression, Regulation, and Function", Experimental Cell Research, 312: 584-593, 2006. Abstract, p. 585, Right col., § 1, p. 589, Right col., § 3, p. 591, Left col., § 2.
Christensen et al. "Proteolytic Processing Converts the Repelling Signal Sema3E Into An Inducer of Invasive Growth and Lung Metastasis", Cancer Research, 65(14): 6167-6177, Jul. 15, 2005. Abstract.
Gu et al. "Semaphorin 3E and Plexin-D1 Control Vascular Pattern Independently of Neuropilins", Science, 307(5707): 265-268, Jan. 14, 2005. Abstract.

(Continued)

*Primary Examiner* — Christine J Saoud
*Assistant Examiner* — Jon M Lockard

(57) ABSTRACT

A method of selecting a semaphorin for treating cancer in a subject is disclosed. The method comprises determining an expression of a semaphorin receptor on tumor cells of a tumor sample of the subject wherein an amount of the semaphorin receptor is indicative of the semaphorin suitable for treating the cancer in the subject. Methods of treating angiogenesis, kits for treating cancer and pharmaceutical compositions comprising semaphorins are also disclosed.

6 Claims, 14 Drawing Sheets
(4 of 14 Drawing Sheet(s) Filed in Color)

(56) References Cited

OTHER PUBLICATIONS

Neufeld et al. "Semaphorins in Cancer," Frontiers in Bioscience 10: 751-760, Jan. 1, 2005.

Palu et al. "In Pursuit of New Developments for Gene Therapy of Human Diseases", Journal of Biotechnology, 68: 1-13, 1999.

Phillips "The Challenge of Gene Therapy and DNA Delivery", Journal of Pharmacy and Pharmacology, JPP, 53: 1169-1174, 2001.

Office Action Dated Sep. 4, 2012 From the Israel Patent Office Re. Application No. 205061 and Its Translation Into English.

\* cited by examiner

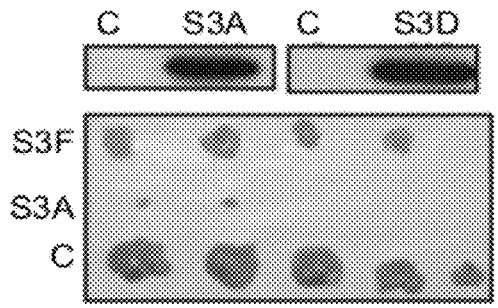
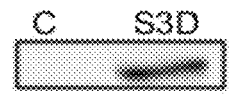
FIG. 2A
FIG.2D
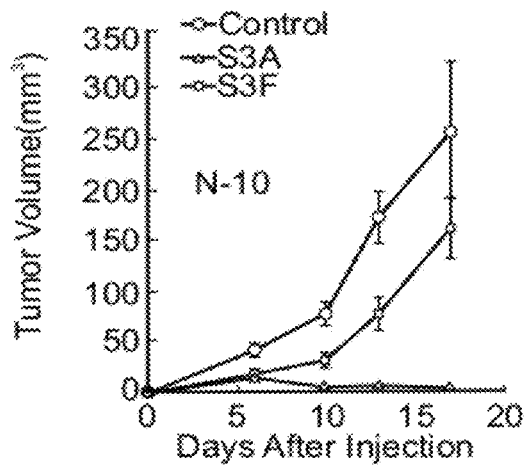
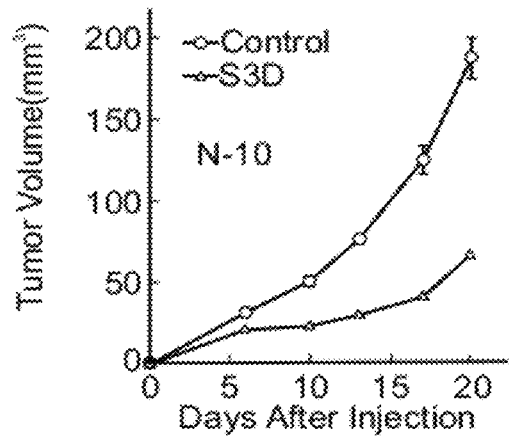
FIG.2B
FIG. 2E
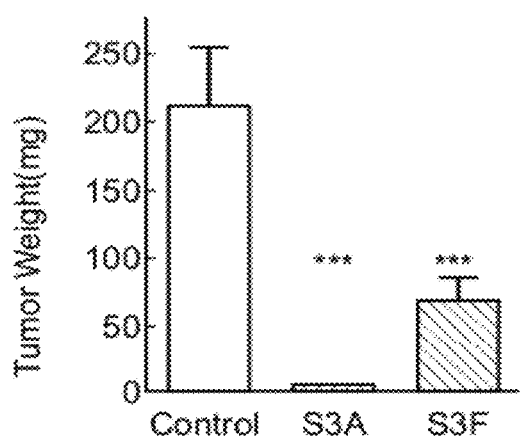
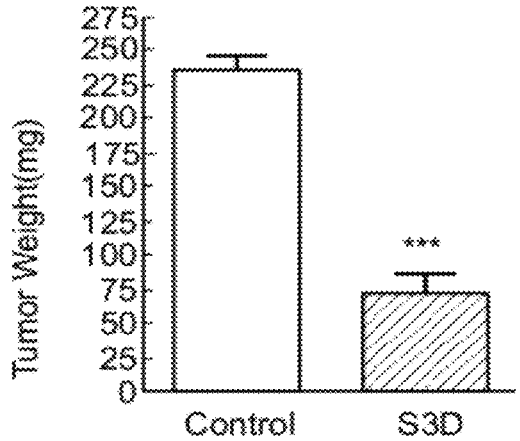
FIG.2C
FIG.2F

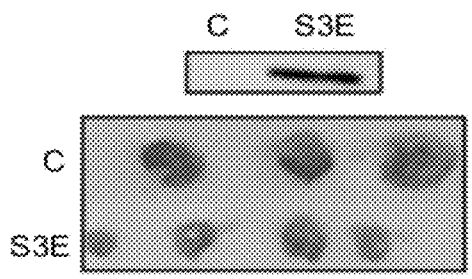
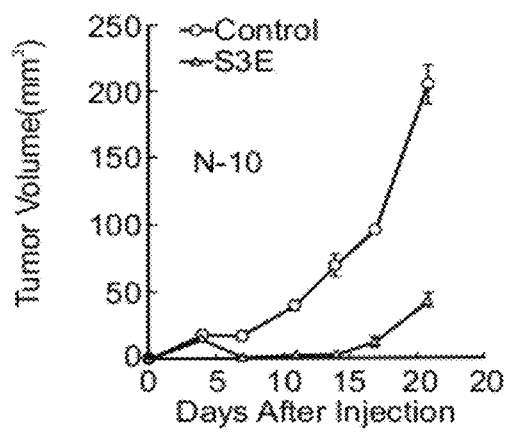
FIG.2G
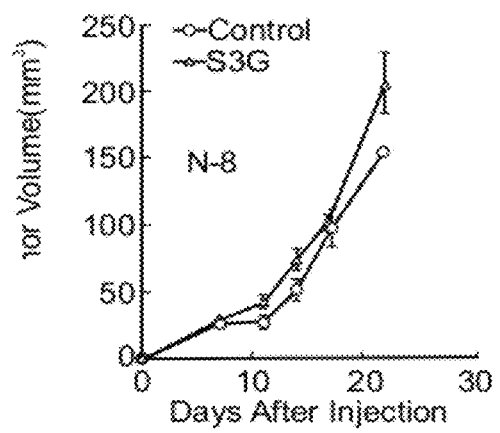
FIG.2J
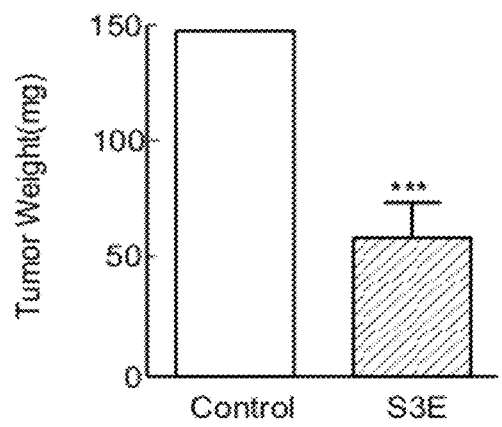
FIG.2H
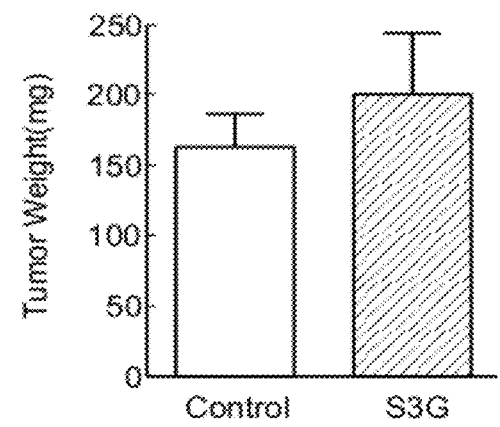
FIG.2K
FIG.2I
FIG.2L

MCF-7

```
                         SEQUENCE LISTING

<160> NUMBER OF SEQ ID NOS: 40

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ccaccttaaa atctgcaggc                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
gtgcatgaag gacagcctct                                               20

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
ttgcagtctc tgtcctccaa                                               20

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
gaaaaatgcg aatggctgat                                               20

<210> SEQ ID NO 5
<211> LENGTH: 20
<212> TYPE: DNA
<213> ORGANISM: Artificial sequence
<220> FEATURE:
```

<223> OTHER INFORMATION: Single strand DNA oligonucleotide

<400> SEQUENCE: 5
ccctgaggtt gcagaagaag                                                  20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
gtcccactgg agaactgcat                                                  20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
ggtttgagag gtccaccagg                                                  20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
ccgtggctgc ctatgactat                                                  20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
catctcgtac tggaccccac                                                  20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
tttacaacgg ctacagcgtg                                                  20

<210> SEQ ID NO 11
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 11
accacgaagg cacggaag                                                    18

<210> SEQ ID NO 12

<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 12
agccagcgga gggacag                                               17

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
agcagtgcgc tcttaaccat                                            20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
caaaggccag agagtggttc                                            20

<210> SEQ ID NO 15
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 15
gagcagctcc acagtccag                                             19

<210> SEQ ID NO 16
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 16
gtgctcgaca gcgtggt                                               17

<210> SEQ ID NO 17
<211> LENGTH: 644
<212> TYPE: PRT
<213> ORGANISM: Homo sapiens

<400> SEQUENCE: 17

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

```
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Pro Val
            100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Ile Phe Lys Arg Gly
            130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Ala Pro Lys Met Ser Glu Ile Ile Leu Glu Phe Glu Ser Phe
            180                 185                 190
Asp Leu Glu Pro Asp Ser Asn Pro Pro Gly Met Phe Cys Arg Tyr
            195                 200                 205
Asp Arg Leu Glu Ile Trp Asp Gly Phe Pro Asp Val Gly Pro His Ile
210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Ser Thr Asn Trp Ser Ala Glu
290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
            355                 360                 365
Trp Ile Thr Ile Lys Glu Gly Asn Lys Pro Val Leu Phe Gln Gly Asn
370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
            435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
```

```
                     500                 505                 510
Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
        530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Gly Ile Lys

<210> SEQ ID NO 18
<211> LENGTH: 909
<212> TYPE: PRT
<213> ORGANISM: Homo sapiens

<400> SEQUENCE: 18

Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240
```

```
Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
                260                 265                 270

Glu Asn Phe Gln Cys Asn Val Pro Leu Gly Met Glu Ser Gly Arg Ile
                275                 280                 285

Ala Asn Glu Gln Ile Ser Ala Ser Ser Thr Tyr Ser Asp Gly Arg Trp
            290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
                340                 345                 350

Gln Asn Gly Tyr Tyr Val Lys Ser Tyr Lys Leu Glu Val Ser Thr Asn
                355                 360                 365

Gly Glu Asp Trp Met Val Tyr Arg His Gly Lys Asn His Lys Val Phe
            370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Ser
            435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Thr Glu Glu Glu Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
```

```
                    660                 665                 670
Ser Ser Pro Asn Asp Arg Thr Phe Pro Asp Asp Arg Asn Phe Leu Arg
            675                 680                 685

Leu Gln Ser Asp Ser Gln Arg Glu Gly Gln Tyr Ala Arg Leu Ile Ser
        690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
            725                 730                 735

Ser Gln Glu Ser Lys Leu Leu Trp Val Ile Arg Glu Asp Gln Gly Gly
        740                 745                 750

Glu Trp Lys His Gly Arg Ile Ile Leu Pro Ser Tyr Asp Met Glu Tyr
            755                 760                 765

Gln Ile Val Phe Glu Gly Val Ile Gly Lys Gly Arg Ser Gly Glu Ile
        770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Val Asp Trp Ser
            805                 810                 815

Asn Ser Ser Ser Ala Thr Ser Gly Ser Gly Ala Pro Ser Thr Asp Lys
        820                 825                 830

Glu Lys Ser Trp Leu Tyr Thr Leu Asp Pro Ile Leu Ile Thr Ile Ile
            835                 840                 845

Ala Met Ser Ser Leu Gly Val Leu Leu Gly Ala Thr Cys Ala Gly Leu
        850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
            885                 890                 895

Lys Val Lys Met Asn His Gln Lys Cys Cys Ser Glu Ala
            900                 905

<210> SEQ ID NO 19
<211> LENGTH: 1873
<212> TYPE: PRT
<213> ORGANISM: Homo sapiens

<400> SEQUENCE: 19

Met Trp Ala Glu Ala Gly Leu Pro Arg Ala Gly Gly Ser Gln Pro
1               5                   10                  15

Pro Phe Arg Thr Phe Ser Ala Ser Asp Trp Gly Leu Thr His Leu Val
            20                  25                  30

Val His Glu Gln Thr Gly Glu Val Tyr Val Gly Ala Val Asn Arg Ile
        35                  40                  45

Tyr Lys Leu Ser Gly Asn Leu Thr Leu Leu Arg Ala His Val Thr Gly
    50                  55                  60

Pro Val Glu Asp Asn Glu Lys Cys Tyr Pro Pro Ser Val Gln Ser
65                  70                  75                  80

Cys Pro His Gly Leu Gly Ser Thr Asp Asn Val Asn Lys Leu Leu Leu
            85                  90                  95

Leu Asp Tyr Ala Ala Asn Arg Leu Leu Ala Cys Gly Ser Ala Ser Gln
        100                 105                 110

Gly Ile Cys Gln Phe Leu Arg Leu Asp Asp Leu Phe Lys Leu Gly Glu
    115                 120                 125

Pro His His Arg Lys Glu His Tyr Leu Ser Ser Val Gln Glu Ala Gly
```

```
                130                 135                 140
Ser Met Ala Gly Val Leu Ile Ala Gly Pro Gly Gln Gly Gln Ala
145                 150                 155                 160

Lys Leu Phe Val Gly Thr Pro Ile Asp Gly Lys Ser Glu Tyr Phe Pro
                165                 170                 175

Thr Leu Ser Ser Arg Arg Leu Met Ala Asn Glu Glu Asp Ala Asp Met
                180                 185                 190

Phe Gly Phe Val Tyr Gln Asp Glu Phe Val Ser Ser Gln Leu Lys Ile
                195                 200                 205

Pro Ser Asp Thr Leu Ser Lys Phe Pro Ala Phe Asp Ile Tyr Tyr Val
210                 215                 220

Tyr Ser Phe Arg Ser Glu Gln Phe Val Tyr Tyr Leu Thr Leu Gln Leu
225                 230                 235                 240

Asp Thr Gln Leu Thr Ser Pro Asp Ala Ala Gly Glu His Phe Phe Thr
                245                 250                 255

Ser Lys Ile Val Arg Leu Cys Val Asp Asp Pro Lys Tyr Ser Tyr
                260                 265                 270

Val Glu Phe Pro Ile Gly Cys Glu Gln Ala Gly Val Glu Tyr Arg Leu
                275                 280                 285

Val Gln Asp Ala Tyr Leu Ser Arg Pro Gly Arg Ala Leu Ala His Gln
290                 295                 300

Leu Gly Leu Ala Glu Asp Glu Asp Val Leu Phe Thr Val Phe Ala Gln
305                 310                 315                 320

Gly Gln Lys Asn Arg Val Lys Pro Pro Lys Glu Ser Ala Leu Cys Leu
                325                 330                 335

Phe Thr Leu Arg Ala Ile Lys Glu Lys Ile Lys Glu Arg Ile Gln Ser
                340                 345                 350

Cys Tyr Arg Gly Glu Gly Lys Leu Ser Leu Pro Trp Leu Leu Asn Lys
                355                 360                 365

Glu Leu Gly Cys Ile Asn Ser Pro Leu Gln Ile Asp Asp Asp Phe Cys
                370                 375                 380

Gly Gln Asp Phe Asn Gln Pro Leu Gly Gly Thr Val Thr Ile Glu Gly
385                 390                 395                 400

Thr Pro Leu Phe Val Asp Lys Asp Gly Leu Thr Ala Val Ala Ala
                405                 410                 415

Tyr Asp Tyr Arg Gly Arg Thr Val Val Phe Ala Gly Thr Arg Ser Gly
                420                 425                 430

Arg Ile Arg Lys Ile Leu Val Asp Leu Ser Asn Pro Gly Gly Arg Pro
                435                 440                 445

Ala Leu Ala Tyr Glu Ser Val Val Ala Gln Glu Gly Ser Pro Ile Leu
450                 455                 460

Arg Asp Leu Val Leu Ser Pro Asn His Gln Tyr Leu Tyr Ala Met Thr
465                 470                 475                 480

Glu Lys Gln Val Thr Arg Val Pro Val Glu Ser Cys Val Gln Tyr Thr
                485                 490                 495

Ser Cys Glu Leu Cys Leu Gly Ser Arg Asp Pro His Cys Gly Trp Cys
                500                 505                 510

Val Leu His Ser Ile Cys Ser Arg Arg Asp Ala Cys Glu Arg Ala Asp
                515                 520                 525

Glu Pro Gln Arg Phe Ala Ala Asp Leu Leu Gln Cys Val Gln Leu Thr
                530                 535                 540

Val Gln Pro Arg Asn Val Ser Val Thr Met Ser Gln Val Pro Leu Val
545                 550                 555                 560
```

```
Leu Gln Ala Trp Asn Val Pro Asp Leu Ser Ala Gly Val Asn Cys Ser
                565                 570                 575

Phe Glu Asp Phe Thr Glu Ser Glu Val Leu Glu Asp Gly Arg Ile
                580                 585                 590

His Cys Arg Ser Pro Ser Ala Arg Glu Val Ala Pro Ile Thr Arg Gly
                595                 600             605

Gln Gly Asp Gln Arg Val Val Lys Leu Tyr Leu Lys Ser Lys Glu Thr
                610                 615                 620

Gly Lys Lys Phe Ala Ser Val Asp Phe Val Phe Tyr Asn Cys Ser Val
625                 630                 635                 640

His Gln Ser Cys Leu Ser Cys Val Asn Gly Ser Phe Pro Cys His Trp
                645                 650                 655

Cys Lys Tyr Arg His Val Cys Thr His Asn Val Ala Asp Cys Ala Phe
                660                 665                 670

Leu Glu Gly Arg Val Asn Val Ser Glu Asp Cys Pro Gln Ile Leu Pro
                675                 680                 685

Ser Thr Gln Ile Tyr Val Pro Val Gly Val Val Lys Pro Ile Thr Leu
                690                 695                 700

Ala Ala Arg Asn Leu Pro Gln Pro Gln Ser Gly Gln Arg Gly Tyr Glu
705                 710                 715                 720

Cys Leu Phe His Ile Pro Gly Ser Pro Ala Arg Val Thr Ala Leu Arg
                725                 730                 735

Phe Asn Ser Ser Leu Gln Cys Gln Asn Ser Ser Tyr Ser Tyr Glu
                740                 745                 750

Gly Asn Asp Val Ser Asp Leu Pro Val Asn Leu Ser Val Val Trp Asn
                755                 760                 765

Gly Asn Phe Val Ile Asp Asn Pro Gln Asn Ile Gln Ala His Leu Tyr
                770                 775                 780

Lys Cys Pro Ala Leu Arg Glu Ser Cys Gly Leu Cys Leu Lys Ala Asp
785                 790                 795                 800

Pro Arg Phe Glu Cys Gly Trp Cys Val Ala Glu Arg Cys Ser Leu
                805                 810                 815

Arg His His Cys Ala Ala Asp Thr Pro Ala Ser Trp Met His Ala Arg
                820                 825                 830

His Gly Ser Ser Arg Cys Thr Asp Pro Lys Ile Leu Lys Leu Ser Pro
                835                 840                 845

Glu Thr Gly Pro Arg Gln Gly Gly Thr Arg Leu Thr Ile Thr Gly Glu
850                 855                 860

Asn Leu Gly Leu Arg Phe Glu Asp Val Arg Leu Gly Val Arg Val Gly
865                 870                 875                 880

Lys Val Leu Cys Ser Pro Val Glu Ser Glu Tyr Ile Ser Ala Glu Gln
                885                 890                 895

Ile Val Cys Glu Ile Gly Asp Ala Ser Ser Val Arg Ala His Asp Ala
                900                 905                 910

Leu Val Glu Val Cys Val Arg Asp Cys Ser Pro His Tyr Arg Ala Leu
                915                 920                 925

Ser Pro Lys Arg Phe Thr Phe Val Thr Pro Thr Phe Tyr Arg Val Ser
                930                 935                 940

Pro Ser Arg Gly Pro Leu Ser Gly Gly Thr Trp Ile Gly Ile Glu Gly
945                 950                 955                 960

Ser His Leu Asn Ala Gly Ser Asp Val Ala Val Ser Val Gly Gly Arg
                965                 970                 975

Pro Cys Ser Phe Ser Trp Arg Asn Ser Arg Glu Ile Arg Cys Leu Thr
                980                 985                 990
```

-continued

```
Pro Pro Gly Gln Ser Pro Gly Ser Ala Pro Ile Ile Ile Asn Ile Asn
        995             1000            1005

Arg Ala Gln Leu Thr Asn Pro Glu Val Lys Tyr Asn Tyr Thr Glu
    1010            1015            1020

Asp Pro Thr Ile Leu Arg Ile Asp Pro Glu Trp Ser Ile Asn Ser
    1025            1030            1035

Gly Gly Thr Leu Leu Thr Val Thr Gly Thr Asn Leu Ala Thr Val
    1040            1045            1050

Arg Glu Pro Arg Ile Arg Ala Lys Tyr Gly Gly Ile Glu Arg Glu
    1055            1060            1065

Asn Gly Cys Leu Val Tyr Asn Asp Thr Met Val Cys Arg Ala
    1070            1075            1080

Pro Ser Val Ala Asn Pro Val Arg Ser Pro Pro Glu Leu Gly Glu
    1085            1090            1095

Arg Pro Asp Glu Leu Gly Phe Val Met Asp Asn Val Arg Ser Leu
    1100            1105            1110

Leu Val Leu Asn Ser Thr Ser Phe Leu Tyr Tyr Pro Asp Pro Val
    1115            1120            1125

Leu Glu Pro Leu Ser Pro Thr Gly Leu Leu Glu Leu Lys Pro Ser
    1130            1135            1140

Ser Pro Leu Ile Leu Lys Gly Arg Asn Leu Leu Pro Pro Ala Pro
    1145            1150            1155

Gly Asn Ser Arg Leu Asn Tyr Thr Val Leu Ile Gly Ser Thr Pro
    1160            1165            1170

Cys Thr Leu Thr Val Ser Glu Thr Gln Leu Leu Cys Glu Ala Pro
    1175            1180            1185

Asn Leu Thr Gly Gln His Lys Val Thr Val Arg Ala Gly Gly Phe
    1190            1195            1200

Glu Phe Ser Pro Gly Thr Leu Gln Val Tyr Ser Asp Ser Leu Leu
    1205            1210            1215

Thr Leu Pro Ala Ile Val Gly Ile Gly Gly Gly Gly Leu Leu
    1220            1225            1230

Leu Leu Val Ile Val Ala Val Leu Ile Ala Tyr Lys Arg Lys Ser
    1235            1240            1245

Arg Asp Ala Asp Arg Thr Leu Lys Arg Leu Gln Leu Gln Met Asp
    1250            1255            1260

Asn Leu Glu Ser Arg Val Ala Leu Glu Cys Lys Glu Ala Phe Ala
    1265            1270            1275

Glu Leu Gln Thr Asp Ile His Glu Leu Thr Asn Asp Leu Asp Gly
    1280            1285            1290

Ala Gly Ile Pro Phe Leu Asp Tyr Arg Thr Tyr Ala Met Arg Val
    1295            1300            1305

Leu Phe Pro Gly Ile Glu Asp His Pro Val Leu Lys Glu Met Glu
    1310            1315            1320

Val Gln Ala Asn Val Glu Lys Ser Leu Thr Leu Phe Gly Gln Leu
    1325            1330            1335

Leu Thr Lys Lys His Phe Leu Leu Thr Phe Ile Arg Thr Leu Glu
    1340            1345            1350

Ala Gln Arg Ser Phe Ser Met Arg Asp Arg Gly Asn Val Ala Ser
    1355            1360            1365

Leu Ile Met Thr Ala Leu Gln Gly Glu Met Glu Tyr Ala Thr Gly
    1370            1375            1380

Val Leu Lys Gln Leu Leu Ser Asp Leu Ile Glu Lys Asn Leu Glu
```

-continued

```
                1385                1390                1395

Ser Lys Asn His Pro Lys Leu Leu Leu Arg Arg Thr Glu Ser Val
    1400                1405                1410

Ala Glu Lys Met Leu Thr Asn Trp Phe Thr Phe Leu Leu Tyr Lys
    1415                1420                1425

Phe Leu Lys Glu Cys Ala Gly Glu Pro Leu Phe Met Leu Tyr Cys
    1430                1435                1440

Ala Ile Lys Gln Gln Met Glu Lys Gly Pro Ile Asp Ala Ile Thr
    1445                1450                1455

Gly Glu Ala Arg Tyr Ser Leu Ser Glu Asp Lys Leu Ile Arg Gln
    1460                1465                1470

Gln Ile Asp Tyr Lys Thr Leu Thr Leu Asn Cys Val Asn Pro Glu
    1475                1480                1485

Asn Glu Asn Ala Pro Glu Val Pro Val Lys Gly Leu Asp Cys Asp
    1490                1495                1500

Thr Val Thr Gln Ala Lys Glu Lys Leu Leu Asp Ala Ala Tyr Lys
    1505                1510                1515

Gly Val Pro Tyr Ser Gln Arg Pro Lys Ala Ala Asp Met Asp Leu
    1520                1525                1530

Glu Trp Arg Gln Gly Arg Met Ala Arg Ile Ile Leu Gln Asp Glu
    1535                1540                1545

Asp Val Thr Thr Lys Ile Asp Asn Asp Trp Lys Arg Leu Asn Thr
    1550                1555                1560

Leu Ala His Tyr Gln Val Thr Asp Gly Ser Ser Val Ala Leu Val
    1565                1570                1575

Pro Lys Gln Thr Ser Ala Tyr Asn Ile Ser Asn Ser Ser Thr Phe
    1580                1585                1590

Thr Lys Ser Leu Ser Arg Tyr Glu Ser Met Leu Arg Thr Ala Ser
    1595                1600                1605

Ser Pro Asp Ser Leu Arg Ser Arg Thr Pro Met Ile Thr Pro Asp
    1610                1615                1620

Leu Glu Ser Gly Thr Lys Leu Trp His Leu Val Lys Asn His Asp
    1625                1630                1635

His Leu Asp Gln Arg Glu Gly Asp Arg Gly Ser Lys Met Val Ser
    1640                1645                1650

Glu Ile Tyr Leu Thr Arg Leu Leu Ala Thr Lys Gly Thr Leu Gln
    1655                1660                1665

Lys Phe Val Asp Asp Leu Phe Glu Thr Ile Phe Ser Thr Ala His
    1670                1675                1680

Arg Gly Ser Ala Leu Pro Leu Ala Ile Lys Tyr Met Phe Asp Phe
    1685                1690                1695

Leu Asp Glu Gln Ala Asp Lys His Gln Ile His Asp Ala Asp Val
    1700                1705                1710

Arg His Thr Trp Lys Ser Asn Cys Leu Pro Leu Arg Phe Trp Val
    1715                1720                1725

Asn Val Ile Lys Asn Pro Gln Phe Val Phe Asp Ile His Lys Asn
    1730                1735                1740

Ser Ile Thr Asp Ala Cys Leu Ser Val Val Ala Gln Thr Phe Met
    1745                1750                1755

Asp Ser Cys Ser Thr Ser Glu His Lys Leu Gly Lys Asp Ser Pro
    1760                1765                1770

Ser Asn Lys Leu Leu Tyr Ala Lys Asp Ile Pro Asn Tyr Lys Ser
    1775                1780                1785
```

```
Trp Val Glu Arg Tyr Tyr Ala Asp Ile Ala Lys Met Pro Ala Ile
    1790                1795                1800

Ser Asp Gln Asp Met Ser Ala Tyr Leu Ala Glu Gln Ser Arg Leu
    1805                1810                1815

His Leu Ser Gln Phe Asn Ser Met Ser Ala Leu His Glu Ile Tyr
    1820                1825                1830

Ser Tyr Ile Thr Lys Tyr Lys Asp Glu Ile Leu Ala Ala Leu Glu
    1835                1840                1845

Lys Asp Glu Gln Ala Arg Arg Gln Arg Leu Arg Ser Lys Leu Glu
    1850                1855                1860

Gln Val Val Asp Thr Met Ala Leu Ser Ser
    1865                1870

<210> SEQ ID NO 20
<211> LENGTH: 1894
<212> TYPE: PRT
<213> ORGANISM: Homo sapiens

<400> SEQUENCE: 20

Met Glu Gln Arg Arg Pro Trp Pro Arg Ala Leu Glu Val Asp Ser Arg
1               5                   10                  15

Ser Val Val Leu Leu Ser Val Val Trp Val Leu Leu Ala Pro Pro Ala
                20                  25                  30

Ala Gly Met Pro Gln Phe Ser Thr Phe His Ser Glu Asn Arg Asp Trp
            35                  40                  45

Thr Phe Asn His Leu Thr Val His Gln Gly Thr Gly Ala Val Tyr Val
        50                  55                  60

Gly Ala Ile Asn Arg Val Tyr Lys Leu Thr Gly Asn Leu Thr Ile Gln
65                  70                  75                  80

Val Ala His Lys Thr Gly Pro Glu Glu Asp Asn Lys Ser Cys Tyr Pro
                85                  90                  95

Pro Leu Ile Val Gln Pro Cys Ser Glu Val Leu Thr Leu Thr Asn Asn
            100                 105                 110

Val Asn Lys Leu Leu Ile Ile Asp Tyr Ser Glu Asn Arg Leu Leu Ala
        115                 120                 125

Cys Gly Ser Leu Tyr Gln Gly Val Cys Lys Leu Leu Arg Leu Asp Asp
    130                 135                 140

Leu Phe Ile Leu Val Glu Pro Ser His Lys Lys Glu His Tyr Leu Ser
145                 150                 155                 160

Ser Val Asn Lys Thr Gly Thr Met Tyr Gly Val Ile Val Arg Ser Glu
                165                 170                 175

Gly Glu Asp Gly Lys Leu Phe Ile Gly Thr Ala Val Asp Gly Lys Gln
            180                 185                 190

Asp Tyr Phe Pro Thr Leu Ser Ser Arg Lys Leu Pro Arg Asp Pro Glu
        195                 200                 205

Ser Ser Ala Met Leu Asp Tyr Glu Leu His Ser Asp Phe Val Ser Ser
    210                 215                 220

Leu Ile Lys Ile Pro Ser Asp Thr Leu Ala Leu Val Ser His Phe Asp
225                 230                 235                 240

Ile Phe Tyr Ile Tyr Gly Phe Ala Ser Gly Gly Phe Val Tyr Phe Leu
                245                 250                 255

Thr Val Gln Pro Glu Thr Pro Glu Gly Val Ala Ile Asn Ser Ala Gly
            260                 265                 270

Asp Leu Phe Tyr Thr Ser Arg Ile Val Arg Leu Cys Lys Asp Asp Pro
        275                 280                 285
```

-continued

```
Lys Phe His Ser Tyr Val Ser Leu Pro Phe Gly Cys Thr Arg Ala Gly
290                 295                 300

Val Glu Tyr Arg Leu Leu Gln Ala Ala Tyr Leu Ala Lys Pro Gly Asp
305                 310                 315                 320

Ser Leu Ala Gln Ala Phe Asn Ile Thr Ser Gln Asp Asp Val Leu Phe
            325                 330                 335

Ala Ile Phe Ser Lys Gly Gln Lys Gln Tyr His His Pro Pro Asp Asp
            340                 345                 350

Ser Ala Leu Cys Ala Phe Pro Ile Arg Ala Ile Asn Leu Gln Ile Lys
            355                 360                 365

Glu Arg Leu Gln Ser Cys Tyr Gln Gly Glu Gly Asn Leu Glu Leu Asn
370                 375                 380

Trp Leu Leu Gly Lys Asp Val Gln Cys Thr Lys Ala Pro Val Pro Ile
385                 390                 395                 400

Asp Asp Asn Phe Cys Gly Leu Asp Ile Asn Gln Pro Leu Gly Gly Ser
            405                 410                 415

Thr Pro Val Glu Gly Leu Thr Leu Tyr Thr Thr Ser Arg Asp Arg Met
            420                 425                 430

Thr Ser Val Ala Ser Tyr Val Tyr Asn Gly Tyr Ser Val Val Phe Val
            435                 440                 445

Gly Thr Lys Ser Gly Lys Leu Lys Lys Ile Arg Ala Asp Gly Pro Pro
450                 455                 460

His Gly Gly Val Gln Tyr Glu Met Val Ser Val Leu Lys Asp Gly Ser
465                 470                 475                 480

Pro Ile Leu Arg Asp Met Ala Phe Ser Ile Asp Gln Arg Tyr Leu Tyr
            485                 490                 495

Val Met Ser Glu Arg Gln Val Thr Arg Val Pro Val Glu Ser Cys Glu
            500                 505                 510

Gln Tyr Thr Thr Cys Gly Glu Cys Leu Ser Ser Gly Asp Pro His Cys
            515                 520                 525

Gly Trp Cys Ala Leu His Asn Met Cys Ser Arg Arg Asp Lys Cys Gln
            530                 535                 540

Gln Ala Trp Glu Pro Asn Arg Phe Ala Ala Ser Ile Ser Gln Cys Val
545                 550                 555                 560

Ser Leu Ala Val His Pro Ser Ser Ile Ser Val Ser Glu His Ser Arg
            565                 570                 575

Leu Leu Ser Leu Val Val Ser Asp Ala Pro Asp Leu Ser Ala Gly Ile
            580                 585                 590

Ala Cys Ala Phe Gly Asn Leu Thr Glu Val Glu Gly Gln Val Ser Gly
            595                 600                 605

Ser Gln Val Ile Cys Ile Ser Pro Gly Pro Lys Asp Val Pro Val Ile
610                 615                 620

Pro Leu Asp Gln Asp Trp Phe Gly Leu Glu Leu Gln Leu Arg Ser Lys
625                 630                 635                 640

Glu Thr Gly Lys Ile Phe Val Ser Thr Glu Phe Lys Phe Tyr Asn Cys
            645                 650                 655

Ser Ala His Gln Leu Cys Leu Ser Cys Val Asn Ser Ala Phe Arg Cys
            660                 665                 670

His Trp Cys Lys Tyr Arg Asn Leu Cys Thr His Asp Pro Thr Thr Cys
            675                 680                 685

Ser Phe Gln Glu Gly Arg Ile Asn Ile Ser Glu Asp Cys Pro Gln Leu
            690                 695                 700

Val Pro Thr Glu Glu Ile Leu Ile Pro Val Gly Glu Val Lys Pro Ile
705                 710                 715                 720
```

Thr Leu Lys Ala Arg Asn Leu Pro Gln Pro Gln Ser Gly Gln Arg Gly
            725                 730                 735

Tyr Glu Cys Val Leu Asn Ile Gln Gly Ala Ile His Arg Val Pro Ala
            740                 745                 750

Leu Arg Phe Asn Ser Ser Val Gln Cys Gln Asn Ser Ser Tyr Gln
            755                 760                 765

Tyr Asp Gly Met Asp Ile Ser Asn Leu Ala Val Asp Phe Ala Val Val
            770                 775                 780

Trp Asn Gly Asn Phe Ile Ile Asp Asn Pro Gln Asp Leu Lys Val His
785                 790                 795                 800

Leu Tyr Lys Cys Ala Ala Gln Arg Glu Ser Cys Gly Leu Cys Leu Lys
            805                 810                 815

Ala Asp Arg Lys Phe Glu Cys Gly Trp Cys Ser Gly Glu Arg Arg Cys
            820                 825                 830

Thr Leu His Gln His Cys Thr Ser Pro Ser Ser Pro Trp Leu Asp Trp
            835                 840                 845

Ser Ser His Asn Val Lys Cys Ser Asn Pro Gln Ile Thr Glu Ile Leu
            850                 855                 860

Thr Val Ser Gly Pro Pro Glu Gly Gly Thr Arg Val Thr Ile His Gly
865                 870                 875                 880

Val Asn Leu Gly Leu Asp Phe Ser Glu Ile Ala His His Val Gln Val
            885                 890                 895

Ala Gly Val Pro Cys Thr Pro Leu Pro Gly Glu Tyr Ile Ile Ala Glu
            900                 905                 910

Gln Ile Val Cys Glu Met Gly His Ala Leu Val Gly Thr Thr Ser Gly
            915                 920                 925

Pro Val Arg Leu Cys Ile Gly Glu Cys Lys Pro Glu Phe Met Thr Lys
            930                 935                 940

Ser His Gln Gln Tyr Thr Phe Val Asn Pro Ser Val Leu Ser Leu Asn
945                 950                 955                 960

Pro Ile Arg Gly Pro Glu Ser Gly Gly Thr Met Val Thr Ile Thr Gly
            965                 970                 975

His Tyr Leu Gly Ala Gly Ser Ser Val Ala Val Tyr Leu Gly Asn Gln
            980                 985                 990

Thr Cys Glu Phe Tyr Gly Arg Ser Met Ser Glu Ile Val Cys Val Ser
            995                 1000                1005

Pro Pro Ser Ser Asn Gly Leu Gly Pro Val Pro Val Ser Val Ser
        1010                1015                1020

Val Asp Arg Ala His Val Asp Ser Asn Leu Gln Phe Glu Tyr Ile
        1025                1030                1035

Asp Asp Pro Arg Val Gln Arg Ile Glu Pro Glu Trp Ser Ile Ala
        1040                1045                1050

Ser Gly His Thr Pro Leu Thr Ile Thr Gly Phe Asn Leu Asp Val
        1055                1060                1065

Ile Gln Glu Pro Arg Ile Arg Val Lys Phe Asn Gly Lys Glu Ser
        1070                1075                1080

Val Asn Val Cys Lys Val Val Asn Thr Thr Thr Leu Thr Cys Leu
        1085                1090                1095

Ala Pro Ser Leu Thr Thr Asp Tyr Arg Pro Gly Leu Asp Thr Val
        1100                1105                1110

Glu Arg Pro Asp Glu Phe Gly Phe Val Phe Asn Asn Val Gln Ser
        1115                1120                1125

Leu Leu Ile Tyr Asn Asp Thr Lys Phe Ile Tyr Tyr Pro Asn Pro

```
                1130              1135              1140
Thr Phe Glu Leu Leu Ser Pro Thr Gly Val Leu Asp Gln Lys Pro
    1145              1150              1155
Gly Ser Pro Ile Ile Leu Lys Gly Lys Asn Leu Cys Pro Pro Ala
    1160              1165              1170
Ser Gly Gly Ala Lys Leu Asn Tyr Thr Val Leu Ile Gly Glu Thr
    1175              1180              1185
Pro Cys Ala Val Thr Val Ser Glu Thr Gln Leu Leu Cys Glu Pro
    1190              1195              1200
Pro Asn Leu Thr Gly Gln His Lys Val Met Val His Val Gly Gly
    1205              1210              1215
Met Val Phe Ser Pro Gly Ser Val Ser Val Ile Ser Asp Ser Leu
    1220              1225              1230
Leu Thr Leu Pro Ala Ile Val Ser Ile Ala Ala Gly Gly Ser Leu
    1235              1240              1245
Leu Leu Ile Ile Val Ile Ile Val Leu Ile Ala Tyr Lys Arg Lys
    1250              1255              1260
Ser Arg Glu Asn Asp Leu Thr Leu Lys Arg Leu Gln Met Gln Met
    1265              1270              1275
Asp Asn Leu Glu Ser Arg Val Ala Leu Glu Cys Lys Glu Ala Phe
    1280              1285              1290
Ala Glu Leu Gln Thr Asp Ile Asn Glu Leu Thr Ser Asp Leu Asp
    1295              1300              1305
Arg Ser Gly Ile Pro Tyr Leu Asp Tyr Arg Thr Tyr Ala Met Arg
    1310              1315              1320
Val Leu Phe Pro Gly Ile Glu Asp His Pro Val Leu Arg Glu Leu
    1325              1330              1335
Glu Val Gln Gly Asn Gly Gln Gln His Val Glu Lys Ala Leu Lys
    1340              1345              1350
Leu Phe Ala Gln Leu Ile Asn Asn Lys Val Phe Leu Leu Thr Phe
    1355              1360              1365
Ile Arg Thr Leu Glu Leu Gln Arg Ser Phe Ser Met Arg Asp Arg
    1370              1375              1380
Gly Asn Val Ala Ser Leu Ile Met Thr Gly Leu Gln Gly Arg Leu
    1385              1390              1395
Glu Tyr Ala Thr Asp Val Leu Lys Gln Leu Leu Ser Asp Leu Ile
    1400              1405              1410
Asp Lys Asn Leu Glu Asn Lys Asn His Pro Lys Leu Leu Leu Arg
    1415              1420              1425
Arg Thr Glu Ser Val Ala Glu Lys Met Leu Thr Asn Trp Phe Ala
    1430              1435              1440
Phe Leu Leu His Lys Phe Leu Lys Glu Cys Ala Gly Glu Pro Leu
    1445              1450              1455
Phe Met Leu Tyr Cys Ala Ile Lys Gln Gln Met Glu Lys Gly Pro
    1460              1465              1470
Ile Asp Ala Ile Thr Gly Glu Ala Arg Tyr Ser Leu Ser Glu Asp
    1475              1480              1485
Lys Leu Ile Arg Gln Gln Ile Glu Tyr Lys Thr Leu Ile Leu Asn
    1490              1495              1500
Cys Val Asn Pro Asp Asn Glu Asn Ser Pro Glu Ile Pro Val Lys
    1505              1510              1515
Val Leu Asn Cys Asp Thr Ile Thr Gln Val Lys Glu Lys Ile Leu
    1520              1525              1530
```

```
Asp Ala Val Tyr Lys Asn Val Pro Tyr Ser Gln Arg Pro Arg Ala
1535                1540                1545

Val Asp Met Asp Leu Glu Trp Arg Gln Gly Arg Ile Ala Arg Val
1550                1555                1560

Val Leu Gln Asp Glu Asp Ile Thr Thr Lys Ile Glu Gly Asp Trp
1565                1570                1575

Lys Arg Leu Asn Thr Leu Met His Tyr Gln Val Ser Asp Arg Ser
1580                1585                1590

Val Val Ala Leu Val Pro Lys Gln Thr Ser Ser Tyr Asn Ile Pro
1595                1600                1605

Ala Ser Ala Ser Ile Ser Arg Thr Ser Ile Ser Arg Tyr Asp Ser
1610                1615                1620

Ser Phe Arg Tyr Thr Gly Ser Pro Asp Ser Leu Arg Ser Arg Ala
1625                1630                1635

Pro Met Ile Thr Pro Asp Leu Glu Ser Gly Val Lys Val Trp His
1640                1645                1650

Leu Val Lys Asn His Asp His Gly Asp Gln Lys Glu Gly Asp Arg
1655                1660                1665

Gly Ser Lys Met Val Ser Glu Ile Tyr Leu Thr Arg Leu Leu Ala
1670                1675                1680

Thr Lys Gly Thr Leu Gln Lys Phe Val Asp Asp Leu Phe Glu Thr
1685                1690                1695

Leu Phe Ser Thr Val His Arg Gly Ser Ala Leu Pro Leu Ala Ile
1700                1705                1710

Lys Tyr Met Phe Asp Phe Leu Asp Glu Gln Ala Asp Arg His Ser
1715                1720                1725

Ile His Asp Thr Asp Val Arg His Thr Trp Lys Ser Asn Cys Leu
1730                1735                1740

Pro Leu Arg Phe Trp Val Asn Val Ile Lys Asn Pro Gln Phe Val
1745                1750                1755

Phe Asp Ile His Lys Gly Ser Ile Thr Asp Ala Cys Leu Ser Val
1760                1765                1770

Val Ala Gln Thr Phe Met Asp Ser Cys Ser Thr Ser Glu His Arg
1775                1780                1785

Leu Gly Lys Asp Ser Pro Ser Asn Lys Leu Leu Tyr Ala Lys Asp
1790                1795                1800

Ile Pro Ser Tyr Lys Ser Trp Val Glu Arg Tyr Tyr Ala Asp Ile
1805                1810                1815

Ala Lys Leu Pro Ala Ile Ser Asp Gln Asp Met Asn Ala Tyr Leu
1820                1825                1830

Ala Glu Gln Ser Arg Leu His Ala Val Glu Phe Asn Met Leu Ser
1835                1840                1845

Ala Leu Asn Glu Ile Tyr Ser Tyr Val Ser Lys Tyr Ser Glu Glu
1850                1855                1860

Leu Ile Gly Ala Leu Glu Gln Asp Glu Gln Ala Arg Arg Gln Arg
1865                1870                1875

Leu Ala Tyr Lys Val Glu Gln Leu Ile Asn Ala Met Ser Ile Glu
1880                1885                1890

Ser

<210> SEQ ID NO 21
<211> LENGTH: 1871
<212> TYPE: PRT
<213> ORGANISM: Homo sapiens
```

<400> SEQUENCE: 21

```
Met Pro Ser Val Cys Leu Leu Leu Leu Phe Leu Ala Val Gly Gly
1               5                   10                  15

Ala Leu Gly Asn Arg Pro Phe Arg Ala Phe Val Val Thr Asp Thr Thr
            20                  25                  30

Leu Thr His Leu Ala Val His Arg Val Thr Gly Glu Val Phe Val Gly
            35                  40                  45

Ala Val Asn Arg Val Phe Lys Leu Ala Pro Asn Leu Thr Glu Leu Arg
50                  55                  60

Ala His Val Thr Gly Pro Val Glu Asp Asn Ala Arg Cys Tyr Pro Pro
65                  70                  75                  80

Pro Ser Met Arg Val Cys Ala His Arg Leu Ala Pro Val Asp Asn Ile
                85                  90                  95

Asn Lys Leu Leu Leu Ile Asp Tyr Ala Ala Arg Arg Leu Val Ala Cys
                100                 105                 110

Gly Ser Ile Trp Gln Gly Ile Cys Gln Phe Leu Arg Leu Asp Asp Leu
            115                 120                 125

Phe Lys Leu Gly Glu Pro His His Arg Lys Glu His Tyr Leu Ser Gly
130                 135                 140

Ala Gln Glu Pro Asp Ser Met Ala Gly Val Ile Val Glu Gln Gly Gln
145                 150                 155                 160

Gly Pro Ser Lys Leu Phe Val Gly Thr Ala Val Asp Gly Lys Ser Glu
                165                 170                 175

Tyr Phe Pro Thr Leu Ser Ser Arg Lys Leu Ile Ser Asp Glu Asp Ser
            180                 185                 190

Ala Asp Met Phe Ser Leu Val Tyr Gln Asp Glu Phe Val Ser Ser Gln
            195                 200                 205

Ile Lys Ile Pro Ser Asp Thr Leu Ser Leu Tyr Pro Ala Phe Asp Ile
210                 215                 220

Tyr Tyr Ile Tyr Gly Phe Val Ser Ala Ser Phe Val Tyr Phe Leu Thr
225                 230                 235                 240

Leu Gln Leu Asp Thr Gln Gln Thr Leu Leu Asp Thr Ala Gly Glu Lys
            245                 250                 255

Phe Phe Thr Ser Lys Ile Val Arg Met Cys Ala Gly Asp Ser Glu Phe
            260                 265                 270

Tyr Ser Tyr Val Glu Phe Pro Ile Gly Cys Ser Trp Arg Gly Val Glu
            275                 280                 285

Tyr Arg Leu Val Gln Ser Ala His Leu Ala Lys Pro Gly Leu Leu Leu
290                 295                 300

Ala Gln Ala Leu Gly Val Pro Ala Asp Glu Asp Val Leu Phe Thr Ile
305                 310                 315                 320

Phe Ser Gln Gly Gln Lys Asn Arg Ala Ser Pro Arg Gln Thr Ile
            325                 330                 335

Leu Cys Leu Phe Thr Leu Ser Asn Ile Asn Ala His Ile Arg Arg Arg
            340                 345                 350

Ile Gln Ser Cys Tyr Arg Gly Glu Gly Thr Leu Ala Leu Pro Trp Leu
            355                 360                 365

Leu Asn Lys Glu Leu Pro Cys Ile Asn Thr Pro Met Gln Ile Asn Gly
370                 375                 380

Asn Phe Cys Gly Leu Val Leu Asn Gln Pro Leu Gly Gly Leu His Val
385                 390                 395                 400

Ile Glu Gly Leu Pro Leu Leu Ala Asp Ser Thr Asp Gly Met Ala Ser
                405                 410                 415
```

-continued

```
Val Ala Ala Tyr Thr Tyr Arg Gln His Ser Val Val Phe Ile Gly Thr
            420                 425                 430

Arg Ser Gly Ser Leu Lys Lys Val Arg Val Asp Gly Phe Gln Asp Ala
            435                 440                 445

His Leu Tyr Glu Thr Val Pro Val Val Asp Gly Ser Pro Ile Leu Arg
            450                 455                 460

Asp Leu Leu Phe Ser Pro Asp His Arg His Ile Tyr Leu Leu Ser Glu
465                 470                 475                 480

Lys Gln Val Ser Gln Leu Pro Val Glu Thr Cys Glu Gln Tyr Gln Ser
                485                 490                 495

Cys Ala Ala Cys Leu Gly Ser Gly Asp Pro His Cys Gly Trp Cys Val
            500                 505                 510

Leu Arg His Arg Cys Cys Arg Glu Gly Ala Cys Leu Gly Ala Ser Ala
            515                 520                 525

Pro His Gly Phe Ala Glu Glu Leu Ser Lys Cys Val Gln Val Arg Val
            530                 535                 540

Arg Pro Asn Asn Val Ser Val Thr Ser Pro Gly Val Gln Leu Thr Val
545                 550                 555                 560

Thr Leu His Asn Val Pro Asp Leu Ser Ala Gly Val Ser Cys Ala Phe
                565                 570                 575

Glu Ala Ala Ala Glu Asn Glu Ala Val Leu Leu Pro Ser Gly Glu Leu
            580                 585                 590

Leu Cys Pro Ser Pro Ser Leu Gln Glu Leu Arg Ala Leu Thr Arg Gly
            595                 600                 605

His Gly Ala Thr Arg Thr Val Arg Leu Gln Leu Leu Ser Lys Glu Thr
            610                 615                 620

Gly Val Arg Phe Ala Gly Ala Asp Phe Val Phe Tyr Asn Cys Ser Val
625                 630                 635                 640

Leu Gln Ser Cys Met Ser Cys Val Gly Ser Pro Tyr Pro Cys His Trp
                645                 650                 655

Cys Lys Tyr Arg His Thr Cys Thr Ser Arg Pro His Glu Cys Ser Phe
            660                 665                 670

Gln Glu Gly Arg Val His Ser Pro Glu Gly Cys Pro Glu Ile Leu Pro
            675                 680                 685

Ser Gly Asp Leu Leu Ile Pro Val Gly Val Met Gln Pro Leu Thr Leu
690                 695                 700

Arg Ala Lys Asn Leu Pro Gln Pro Gln Ser Gly Gln Lys Asn Tyr Glu
705                 710                 715                 720

Cys Val Val Arg Val Gln Gly Arg Gln Gln Arg Val Pro Ala Val Arg
                725                 730                 735

Phe Asn Ser Ser Ser Val Gln Cys Gln Asn Ala Ser Tyr Ser Tyr Glu
            740                 745                 750

Gly Asp Glu His Gly Asp Thr Glu Leu Asp Phe Ser Val Val Trp Asp
            755                 760                 765

Gly Asp Phe Pro Ile Asp Lys Pro Pro Ser Phe Arg Ala Leu Leu Tyr
            770                 775                 780

Lys Cys Trp Ala Gln Arg Pro Ser Cys Gly Leu Cys Leu Lys Ala Asp
785                 790                 795                 800

Pro Arg Phe Asn Cys Gly Trp Cys Ile Ser Glu His Arg Cys Gln Leu
                805                 810                 815

Arg Thr His Cys Pro Ala Pro Lys Thr Asn Trp Met His Leu Ser Gln
            820                 825                 830

Lys Gly Thr Arg Cys Ser His Pro Arg Ile Thr Gln Ile His Pro Leu
            835                 840                 845
```

-continued

Val Gly Pro Lys Glu Gly Gly Thr Arg Val Thr Ile Val Gly Asp Asn
850                 855                 860

Leu Gly Leu Leu Ser Arg Glu Val Gly Leu Arg Val Ala Gly Val Arg
865                 870                 875                 880

Cys Asn Ser Ile Pro Ala Glu Tyr Ile Ser Ala Glu Arg Ile Val Cys
                    885                 890                 895

Glu Met Glu Glu Ser Leu Val Pro Ser Pro Pro Gly Pro Val Glu
            900                 905                 910

Leu Cys Val Gly Asp Cys Ser Ala Asp Phe Arg Thr Gln Ser Glu Gln
                915                 920                 925

Val Tyr Ser Phe Val Thr Pro Thr Phe Asp Gln Val Ser Pro Ser Arg
930                 935                 940

Gly Pro Ala Ser Gly Gly Thr Arg Leu Thr Ile Ser Gly Ser Ser Leu
945                 950                 955                 960

Asp Ala Gly Ser Arg Val Thr Val Thr Val Arg Asp Ser Glu Cys Gln
                965                 970                 975

Phe Val Arg Arg Asp Ala Lys Ala Ile Val Cys Ile Ser Pro Leu Ser
                980                 985                 990

Thr Leu Gly Pro Ser Gln Ala Pro Ile Thr Leu Ala Ile Asp Arg Ala
            995                 1000                1005

Asn Ile Ser Ser Pro Gly Leu Ile Tyr Thr Tyr Thr Gln Asp Pro
    1010                1015                1020

Thr Val Thr Arg Leu Glu Pro Thr Trp Ser Ile Ile Asn Gly Ser
    1025                1030                1035

Thr Ala Ile Thr Val Ser Gly Thr His Leu Leu Thr Val Gln Glu
    1040                1045                1050

Pro Arg Val Arg Ala Lys Tyr Arg Gly Ile Glu Thr Thr Asn Thr
    1055                1060                1065

Cys Gln Val Ile Asn Asp Thr Ala Met Leu Cys Lys Ala Pro Gly
    1070                1075                1080

Ile Phe Leu Gly Arg Pro Gln Pro Arg Ala Gln Gly Glu His Pro
    1085                1090                1095

Asp Glu Phe Gly Phe Leu Leu Asp His Val Gln Thr Ala Arg Ser
    1100                1105                1110

Leu Asn Arg Ser Ser Phe Thr Tyr Tyr Pro Asp Pro Ser Phe Glu
    1115                1120                1125

Pro Leu Gly Pro Ser Gly Val Leu Asp Val Lys Pro Gly Ser His
    1130                1135                1140

Val Val Leu Lys Gly Lys Asn Leu Ile Pro Ala Ala Ala Gly Ser
    1145                1150                1155

Ser Arg Leu Asn Tyr Thr Val Leu Ile Gly Gly Gln Pro Cys Ser
    1160                1165                1170

Leu Thr Val Ser Asp Thr Gln Leu Leu Cys Asp Ser Pro Ser Gln
    1175                1180                1185

Thr Gly Arg Gln Pro Val Met Val Leu Val Gly Gly Leu Glu Phe
    1190                1195                1200

Trp Leu Gly Thr Leu His Ile Ser Ala Glu Arg Ala Leu Thr Leu
    1205                1210                1215

Pro Ala Met Met Gly Leu Ala Ala Gly Gly Gly Leu Leu Leu Leu
    1220                1225                1230

Ala Ile Thr Ala Val Leu Val Ala Tyr Lys Arg Lys Thr Gln Asp
    1235                1240                1245

Ala Asp Arg Thr Leu Lys Arg Leu Gln Leu Gln Met Asp Asn Leu

-continued

```
            1250                1255                1260
Glu Ser Arg Val Ala Leu Glu Cys Lys Glu Ala Phe Ala Glu Leu
    1265                1270                1275
Gln Thr Asp Ile Asn Glu Leu Thr Asn His Met Asp Glu Val Gln
    1280                1285                1290
Ile Pro Phe Leu Asp Tyr Arg Thr Tyr Ala Val Arg Val Leu Phe
    1295                1300                1305
Pro Gly Ile Glu Ala His Pro Val Leu Lys Glu Leu Asp Thr Pro
    1310                1315                1320
Pro Asn Val Glu Lys Ala Leu Arg Leu Phe Gly Gln Leu Leu His
    1325                1330                1335
Ser Arg Ala Phe Val Leu Thr Phe Ile His Thr Leu Glu Ala Gln
    1340                1345                1350
Ser Ser Phe Ser Met Arg Asp Arg Gly Thr Val Ala Ser Leu Thr
    1355                1360                1365
Met Val Ala Leu Gln Ser Arg Leu Asp Tyr Ala Thr Gly Leu Leu
    1370                1375                1380
Lys Gln Leu Leu Ala Asp Leu Ile Glu Lys Asn Leu Glu Ser Lys
    1385                1390                1395
Asn His Pro Lys Leu Leu Leu Arg Arg Thr Glu Ser Val Ala Glu
    1400                1405                1410
Lys Met Leu Thr Asn Trp Phe Thr Phe Leu Leu His Lys Phe Leu
    1415                1420                1425
Lys Glu Cys Ala Gly Glu Pro Leu Phe Leu Leu Tyr Cys Ala Ile
    1430                1435                1440
Lys Gln Gln Met Glu Lys Gly Pro Ile Asp Ala Ile Thr Gly Glu
    1445                1450                1455
Ala Arg Tyr Ser Leu Ser Glu Asp Lys Leu Ile Arg Gln Gln Ile
    1460                1465                1470
Asp Tyr Lys Thr Leu Thr Leu His Cys Val Cys Pro Glu Asn Glu
    1475                1480                1485
Gly Ser Ala Gln Val Pro Val Lys Val Leu Asn Cys Asp Ser Ile
    1490                1495                1500
Thr Gln Ala Lys Asp Lys Leu Leu Asp Thr Val Tyr Lys Gly Ile
    1505                1510                1515
Pro Tyr Ser Gln Arg Pro Lys Ala Glu Asp Met Asp Leu Glu Trp
    1520                1525                1530
Arg Gln Gly Arg Met Thr Arg Ile Ile Leu Gln Asp Glu Asp Val
    1535                1540                1545
Thr Thr Lys Ile Glu Cys Asp Trp Lys Arg Leu Asn Ser Leu Ala
    1550                1555                1560
His Tyr Gln Val Thr Asp Gly Ser Leu Val Ala Leu Val Pro Lys
    1565                1570                1575
Gln Val Ser Ala Tyr Asn Met Ala Asn Ser Phe Thr Phe Thr Arg
    1580                1585                1590
Ser Leu Ser Arg Tyr Glu Ser Leu Leu Arg Thr Ala Ser Ser Pro
    1595                1600                1605
Asp Ser Leu Arg Ser Arg Ala Pro Met Ile Thr Pro Asp Gln Glu
    1610                1615                1620
Thr Gly Thr Lys Leu Trp His Leu Val Lys Asn His Asp His Ala
    1625                1630                1635
Asp His Arg Glu Gly Asp Arg Gly Ser Lys Met Val Ser Glu Ile
    1640                1645                1650
```

```
Tyr Leu Thr Arg Leu Leu Ala Thr Lys Gly Thr Leu Gln Lys Phe
    1655                1660                1665

Val Asp Asp Leu Phe Glu Thr Val Phe Ser Thr Ala His Arg Gly
1670                1675                1680

Ser Ala Leu Pro Leu Ala Ile Lys Tyr Met Phe Asp Phe Leu Asp
    1685                1690                1695

Glu Gln Ala Asp Gln Arg Gln Ile Ser Asp Pro Asp Val Arg His
1700                1705                1710

Thr Trp Lys Ser Asn Cys Leu Pro Leu Arg Phe Trp Val Asn Val
    1715                1720                1725

Ile Lys Asn Pro Gln Phe Val Phe Asp Ile His Lys Asn Ser Ile
1730                1735                1740

Thr Asp Ala Cys Leu Ser Val Val Ala Gln Thr Phe Met Asp Ser
    1745                1750                1755

Cys Ser Thr Ser Glu His Arg Leu Gly Lys Asp Ser Pro Ser Asn
1760                1765                1770

Lys Leu Leu Tyr Ala Lys Asp Ile Pro Asn Tyr Lys Ser Trp Val
    1775                1780                1785

Glu Arg Tyr Tyr Arg Asp Ile Ala Lys Met Ala Ser Ile Ser Asp
1790                1795                1800

Gln Asp Met Asp Ala Tyr Leu Val Glu Gln Ser Arg Leu His Ala
    1805                1810                1815

Ser Asp Phe Ser Val Leu Ser Ala Leu Asn Glu Leu Tyr Phe Tyr
1820                1825                1830

Val Thr Lys Tyr Arg Gln Glu Ile Leu Thr Ala Leu Asp Arg Asp
    1835                1840                1845

Ala Ser Cys Arg Lys His Lys Leu Arg Gln Lys Leu Glu Gln Ile
1850                1855                1860

Ile Ser Leu Val Ser Ser Asp Ser
    1865                1870

<210> SEQ ID NO 22
<211> LENGTH: 1894
<212> TYPE: PRT
<213> ORGANISM: Homo sapiens

<400> SEQUENCE: 22

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
            20                  25                  30

Leu Ser Gln Lys Gln Arg Ser Phe Val Thr Phe Arg Gly Glu Pro Ala
        35                  40                  45

Glu Gly Phe Asn His Leu Val Val Asp Glu Arg Thr Gly His Ile Tyr
    50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140
```

```
Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
            165                 170                 175

Ser Asn Leu Asp Asp Lys Leu Phe Ile Ala Thr Ala Val Asp Gly Lys
        180                 185                 190

Pro Glu Tyr Phe Pro Thr Ile Ser Ser Arg Lys Leu Thr Lys Asn Ser
    195                 200                 205

Glu Ala Asp Gly Met Phe Ala Tyr Val Phe His Asp Glu Phe Val Ala
210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365

Glu Arg Leu Gln Ser Cys Tyr Arg Gly Glu Gly Thr Leu Asp Leu Ala
    370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                405                 410                 415

Asp Met Val Arg Gly Ile Pro Val Phe Thr Glu Asp Arg Asp Arg Met
            420                 425                 430

Thr Ser Val Ile Ala Tyr Val Tyr Lys Asn His Ser Leu Ala Phe Val
        435                 440                 445

Gly Thr Lys Ser Gly Lys Leu Lys Lys Ile Arg Val Asp Gly Pro Arg
    450                 455                 460

Gly Asn Ala Leu Gln Tyr Glu Thr Val Gln Val Asp Pro Gly Pro
465                 470                 475                 480

Val Leu Arg Asp Met Ala Phe Ser Lys Asp His Glu Gln Leu Tyr Ile
                485                 490                 495

Met Ser Glu Arg Gln Leu Thr Arg Val Pro Val Glu Ser Cys Gly Gln
            500                 505                 510

Tyr Gln Ser Cys Gly Glu Cys Leu Gly Ser Gly Asp Pro His Cys Gly
        515                 520                 525

Trp Cys Val Leu His Asn Thr Cys Thr Arg Lys Glu Arg Cys Glu Arg
    530                 535                 540

Ser Lys Glu Pro Arg Arg Phe Ala Ser Glu Met Lys Gln Cys Val Arg
545                 550                 555                 560

Leu Thr Val His Pro Asn Asn Ile Ser Val Ser Gln Tyr Asn Val Leu
                565                 570                 575
```

-continued

```
Leu Val Leu Glu Thr Tyr Asn Val Pro Glu Leu Ser Ala Gly Val Asn
        580                 585                 590
Cys Thr Phe Glu Asp Leu Ser Glu Met Asp Gly Leu Val Val Gly Asn
        595                 600                 605
Gln Ile Gln Cys Tyr Ser Pro Ala Ala Lys Glu Val Pro Arg Ile Ile
        610                 615                 620
Thr Glu Asn Gly Asp His His Val Val Gln Leu Gln Leu Lys Ser Lys
625                 630                 635                 640
Glu Thr Gly Met Thr Phe Ala Ser Thr Ser Phe Val Phe Tyr Asn Cys
                645                 650                 655
Ser Val His Asn Ser Cys Leu Ser Cys Val Glu Ser Pro Tyr Arg Cys
                660                 665                 670
His Trp Cys Lys Tyr Arg His Val Cys Thr His Asp Pro Lys Thr Cys
                675                 680                 685
Ser Phe Gln Glu Gly Arg Val Lys Leu Pro Glu Asp Cys Pro Gln Leu
        690                 695                 700
Leu Arg Val Asp Lys Ile Leu Val Pro Val Glu Val Ile Lys Pro Ile
705                 710                 715                 720
Thr Leu Lys Ala Lys Asn Leu Pro Gln Pro Gln Ser Gly Gln Arg Gly
                725                 730                 735
Tyr Glu Cys Ile Leu Asn Ile Gln Gly Ser Glu Gln Arg Val Pro Ala
                740                 745                 750
Leu Arg Phe Asn Ser Ser Val Gln Cys Gln Asn Thr Ser Tyr Ser
        755                 760                 765
Tyr Glu Gly Met Glu Ile Asn Asn Leu Pro Val Glu Leu Thr Val Val
        770                 775                 780
Trp Asn Gly His Phe Asn Ile Asp Asn Pro Ala Gln Asn Lys Val His
785                 790                 795                 800
Leu Tyr Lys Cys Gly Ala Met Arg Glu Ser Cys Gly Leu Cys Leu Lys
                805                 810                 815
Ala Asp Pro Asp Phe Ala Cys Gly Trp Cys Gln Gly Pro Gly Gln Cys
                820                 825                 830
Thr Leu Arg Gln His Cys Pro Ala Gln Glu Ser Gln Trp Leu Glu Leu
        835                 840                 845
Ser Gly Ala Lys Ser Lys Cys Thr Asn Pro Arg Ile Thr Glu Ile Ile
        850                 855                 860
Pro Val Thr Gly Pro Arg Glu Gly Gly Thr Lys Val Thr Ile Arg Gly
865                 870                 875                 880
Glu Asn Leu Gly Leu Glu Phe Arg Asp Ile Ala Ser His Val Lys Val
                885                 890                 895
Ala Gly Val Glu Cys Ser Pro Leu Val Asp Gly Tyr Ile Pro Ala Glu
                900                 905                 910
Gln Ile Val Cys Glu Met Gly Glu Ala Lys Pro Ser Gln His Ala Gly
                915                 920                 925
Phe Val Glu Ile Cys Val Ala Val Cys Arg Pro Glu Phe Met Ala Arg
        930                 935                 940
Ser Ser Gln Leu Tyr Tyr Phe Met Thr Leu Thr Leu Ser Asp Leu Lys
945                 950                 955                 960
Pro Ser Arg Gly Pro Met Ser Gly Gly Thr Gln Val Thr Ile Thr Gly
                965                 970                 975
Thr Asn Leu Asn Ala Gly Ser Asn Val Val Val Met Phe Gly Lys Gln
        980                 985                 990
Pro Cys Leu Phe His Arg Arg Ser  Pro Ser Tyr Ile Val  Cys Asn Thr
```

-continued

```
             995                1000               1005
Thr Ser  Ser Asp Glu Val Leu Glu Met Lys Val Ser  Val Gln Val
    1010                 1015               1020

Asp Arg  Ala Lys Ile His Gln Asp Leu Val Phe Gln  Tyr Val Glu
    1025                 1030               1035

Asp Pro  Thr Ile Val Arg Ile Glu Pro Glu Trp Ser  Ile Val Ser
    1040                 1045               1050

Gly Asn  Thr Pro Ile Ala Val Trp Gly Thr His Leu  Asp Leu Ile
    1055                 1060               1065

Gln Asn  Pro Gln Ile Arg Ala Lys His Gly Gly Lys  Glu His Ile
    1070                 1075               1080

Asn Ile  Cys Glu Val Leu Asn Ala Thr Glu Met Thr  Cys Gln Ala
    1085                 1090               1095

Pro Ala  Leu Ala Leu Gly Pro Asp His Gln Ser Asp  Leu Thr Glu
    1100                 1105               1110

Arg Pro  Glu Glu Phe Gly Phe Ile Leu Asp Asn Val  Gln Ser Leu
    1115                 1120               1125

Leu Ile  Leu Asn Lys Thr Asn Phe Thr Tyr Tyr Pro  Asn Pro Val
    1130                 1135               1140

Phe Glu  Ala Phe Gly Pro Ser Gly Ile Leu Glu Leu  Lys Pro Gly
    1145                 1150               1155

Thr Pro  Ile Ile Leu Lys Gly Lys Asn Leu Ile Pro  Pro Val Ala
    1160                 1165               1170

Gly Gly  Asn Val Lys Leu Asn Tyr Thr Val Leu Val  Gly Glu Lys
    1175                 1180               1185

Pro Cys  Thr Val Thr Val Ser Asp Val Gln Leu Leu  Cys Glu Ser
    1190                 1195               1200

Pro Asn  Leu Ile Gly Arg His Lys Val Met Ala Arg  Val Gly Gly
    1205                 1210               1215

Met Glu  Tyr Ser Pro Gly Met Val Tyr Ile Ala Pro  Asp Ser Pro
    1220                 1225               1230

Leu Ser  Leu Pro Ala Ile Val Ser Ile Ala Val Ala  Gly Gly Leu
    1235                 1240               1245

Leu Ile  Ile Phe Ile Val Ala Val Leu Ile Ala Tyr  Lys Arg Lys
    1250                 1255               1260

Ser Arg  Glu Ser Asp Leu Thr Leu Lys Arg Leu Gln  Met Gln Met
    1265                 1270               1275

Asp Asn  Leu Glu Ser Arg Val Ala Leu Glu Cys Lys  Glu Ala Phe
    1280                 1285               1290

Ala Glu  Leu Gln Thr Asp Ile His Glu Leu Thr Ser  Asp Leu Asp
    1295                 1300               1305

Gly Ala  Gly Ile Pro Phe Leu Asp Tyr Arg Thr Tyr  Thr Met Arg
    1310                 1315               1320

Val Leu  Phe Pro Gly Ile Glu Asp His Pro Val Leu  Arg Asp Leu
    1325                 1330               1335

Glu Val  Pro Gly Tyr Arg Gln Glu Arg Val Glu Lys  Gly Leu Lys
    1340                 1345               1350

Leu Phe  Ala Gln Leu Ile Asn Asn Lys Val Phe Leu  Leu Ser Phe
    1355                 1360               1365

Ile Arg  Thr Leu Glu Ser Gln Arg Ser Phe Ser Met  Arg Asp Arg
    1370                 1375               1380

Gly Asn  Val Ala Ser Leu Ile Met Thr Val Leu Gln  Ser Lys Leu
    1385                 1390               1395
```

-continued

```
Glu Tyr Ala Thr Asp Val Leu Lys Gln Leu Leu Ala Asp Leu Ile
    1400                1405                1410

Asp Lys Asn Leu Glu Ser Lys Asn His Pro Lys Leu Leu Leu Arg
    1415                1420                1425

Arg Thr Glu Ser Val Ala Glu Lys Met Leu Thr Asn Trp Phe Thr
    1430                1435                1440

Phe Leu Leu Tyr Lys Phe Leu Lys Glu Cys Ala Gly Glu Pro Leu
    1445                1450                1455

Phe Ser Leu Phe Cys Ala Ile Lys Gln Gln Met Glu Lys Gly Pro
    1460                1465                1470

Ile Asp Ala Ile Thr Gly Glu Ala Arg Tyr Ser Leu Ser Glu Asp
    1475                1480                1485

Lys Leu Ile Arg Gln Gln Ile Asp Tyr Lys Thr Leu Val Leu Ser
    1490                1495                1500

Cys Val Ser Pro Asp Asn Ala Asn Ser Pro Glu Val Pro Val Lys
    1505                1510                1515

Ile Leu Asn Cys Asp Thr Ile Thr Gln Val Lys Glu Lys Ile Leu
    1520                1525                1530

Asp Ala Ile Phe Lys Asn Val Pro Cys Ser His Arg Pro Lys Ala
    1535                1540                1545

Ala Asp Met Asp Leu Glu Trp Arg Gln Gly Ser Gly Ala Arg Met
    1550                1555                1560

Ile Leu Gln Asp Glu Asp Ile Thr Thr Lys Ile Glu Asn Asp Trp
    1565                1570                1575

Lys Arg Leu Asn Thr Leu Ala His Tyr Gln Val Pro Asp Gly Ser
    1580                1585                1590

Val Val Ala Leu Val Ser Lys Gln Val Thr Ala Tyr Asn Ala Val
    1595                1600                1605

Asn Asn Ser Thr Val Ser Arg Thr Ser Ala Ser Lys Tyr Glu Asn
    1610                1615                1620

Met Ile Arg Tyr Thr Gly Ser Pro Asp Ser Leu Arg Ser Arg Thr
    1625                1630                1635

Pro Met Ile Thr Pro Asp Leu Glu Ser Gly Val Lys Met Trp His
    1640                1645                1650

Leu Val Lys Asn His Glu His Gly Asp Gln Lys Glu Gly Asp Arg
    1655                1660                1665

Gly Ser Lys Met Val Ser Glu Ile Tyr Leu Thr Arg Leu Leu Ala
    1670                1675                1680

Thr Lys Gly Thr Leu Gln Lys Phe Val Asp Asp Leu Phe Glu Thr
    1685                1690                1695

Ile Phe Ser Thr Ala His Arg Gly Ser Ala Leu Pro Leu Ala Ile
    1700                1705                1710

Lys Tyr Met Phe Asp Phe Leu Asp Glu Gln Ala Asp Lys His Gly
    1715                1720                1725

Ile His Asp Pro His Val Arg His Thr Trp Lys Ser Asn Cys Leu
    1730                1735                1740

Pro Leu Arg Phe Trp Val Asn Met Ile Lys Asn Pro Gln Phe Val
    1745                1750                1755

Phe Asp Ile His Lys Asn Ser Ile Thr Asp Ala Cys Leu Ser Val
    1760                1765                1770

Val Ala Gln Thr Phe Met Asp Ser Cys Ser Thr Ser Glu His Arg
    1775                1780                1785

Leu Gly Lys Asp Ser Pro Ser Asn Lys Leu Leu Tyr Ala Lys Asp
    1790                1795                1800
```

```
Ile Pro Ser Tyr Lys Asn Trp Val Glu Arg Tyr Tyr Ser Asp Ile
    1805                1810                1815

Gly Lys Met Pro Ala Ile Ser Asp Gln Asp Met Asn Ala Tyr Leu
1820                1825                1830

Ala Glu Gln Ser Arg Met His Met Asn Glu Phe Asn Thr Met Ser
    1835                1840                1845

Ala Leu Ser Glu Ile Phe Ser Tyr Val Gly Lys Tyr Ser Glu Glu
    1850                1855                1860

Ile Leu Gly Pro Leu Asp His Asp Asp Gln Cys Gly Lys Gln Lys
    1865                1870                1875

Leu Ala Tyr Lys Leu Glu Gln Val Ile Thr Leu Met Ser Leu Asp
    1880                1885                1890

Ser

<210> SEQ ID NO 23
<211> LENGTH: 492
<212> TYPE: PRT
<213> ORGANISM: Homo sapiens

<400> SEQUENCE: 23

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
            20                  25                  30

Leu Ser Gln Lys Gln Arg Ser Phe Val Thr Phe Arg Gly Glu Pro Ala
        35                  40                  45

Glu Gly Phe Asn His Leu Val Val Asp Glu Arg Thr Gly His Ile Tyr
    50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
            100                 105                 110

Asn Val Asn Lys Met Leu Leu Ile Asp Tyr Lys Glu Asn Arg Leu Ile
        115                 120                 125

Ala Cys Gly Ser Leu Tyr Gln Gly Ile Cys Lys Leu Leu Arg Leu Glu
    130                 135                 140

Asp Leu Phe Lys Leu Gly Glu Pro Tyr His Lys Lys Glu His Tyr Leu
145                 150                 155                 160

Ser Gly Val Asn Glu Ser Gly Ser Val Phe Gly Val Ile Val Ser Tyr
                165                 170                 175

Ser Asn Leu Asp Asp Lys Leu Phe Ile Ala Thr Ala Val Asp Gly Lys
            180                 185                 190

Pro Glu Tyr Phe Pro Thr Ile Ser Ser Arg Lys Leu Thr Lys Asn Ser
        195                 200                 205

Glu Ala Asp Gly Met Phe Ala Tyr Val Phe His Asp Glu Phe Val Ala
    210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
                245                 250                 255

Leu Thr Leu Gln Pro Glu Met Val Ser Pro Pro Gly Ser Thr Thr Lys
            260                 265                 270
```

```
Glu Gln Val Tyr Thr Ser Lys Leu Val Arg Leu Cys Lys Glu Asp Thr
            275                 280                 285

Ala Phe Asn Ser Tyr Val Glu Val Pro Ile Gly Cys Glu Arg Ser Gly
    290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Leu Leu Phe
                325                 330                 335

Thr Val Phe Ser Lys Gly Gln Lys Arg Lys Met Lys Ser Leu Asp Glu
                340                 345                 350

Ser Ala Leu Cys Ile Phe Ile Leu Lys Gln Ile Asn Asp Arg Ile Lys
                355                 360                 365

Glu Arg Leu Gln Ser Cys Tyr Arg Gly Glu Gly Thr Leu Asp Leu Ala
            370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
                    405                 410                 415

Asp Met Val Arg Gly Ile Pro Val Phe Thr Glu Asp Arg Asp Arg Met
                420                 425                 430

Thr Ser Val Ile Ala Tyr Val Tyr Lys Asn His Ser Leu Ala Phe Val
                435                 440                 445

Gly Thr Lys Ser Gly Lys Leu Lys Lys Met Pro Gly Thr Ser Leu Cys
            450                 455                 460

Pro Thr Leu Glu Leu Gln Thr Gly Pro Arg Ser His Arg Ala Thr Val
465                 470                 475                 480

Thr Leu Glu Leu Leu Phe Ser Ser Cys Ser Ser Asn
                485                 490

<210> SEQ ID NO 24
<211> LENGTH: 522
<212> TYPE: PRT
<213> ORGANISM: Homo sapiens

<400> SEQUENCE: 24

Met Lys Ala Met Pro Trp Asn Trp Thr Cys Leu Leu Ser His Leu Leu
1               5                   10                  15

Met Val Gly Met Gly Ser Ser Thr Leu Leu Thr Arg Gln Pro Ala Pro
            20                  25                  30

Leu Ser Gln Lys Gln Arg Ser Phe Val Thr Phe Arg Gly Glu Pro Ala
        35                  40                  45

Glu Gly Phe Asn His Leu Val Val Asp Glu Arg Thr Gly His Ile Tyr
    50                  55                  60

Leu Gly Ala Val Asn Arg Ile Tyr Lys Leu Ser Ser Asp Leu Lys Val
65                  70                  75                  80

Leu Val Thr His Glu Thr Gly Pro Asp Glu Asp Asn Pro Lys Cys Tyr
                85                  90                  95

Pro Pro Arg Ile Val Gln Thr Cys Asn Glu Pro Leu Thr Thr Thr Asn
                100                 105                 110

Asn Val Asn Lys Met Leu Leu Ile Asp Tyr Lys Glu Asn Arg Leu Ile
            115                 120                 125

Ala Cys Gly Ser Leu Tyr Gln Gly Ile Cys Lys Leu Leu Arg Leu Glu
        130                 135                 140

Asp Leu Phe Lys Leu Gly Glu Pro Tyr His Lys Lys Glu His Tyr Leu
145                 150                 155                 160
```

-continued

```
Ser Gly Val Asn Glu Ser Gly Val Phe Gly Val Val Ser Tyr
            165                 170                 175

Ser Asn Leu Asp Asp Lys Leu Phe Ile Ala Thr Ala Val Asp Gly Lys
        180                 185                 190

Pro Glu Tyr Phe Pro Thr Ile Ser Ser Arg Lys Leu Thr Lys Asn Ser
            195                 200                 205

Glu Ala Asp Gly Met Phe Ala Tyr Val Phe His Asp Glu Phe Val Ala
        210                 215                 220

Ser Met Ile Lys Ile Pro Ser Asp Thr Phe Thr Ile Ile Pro Asp Phe
225                 230                 235                 240

Asp Ile Tyr Tyr Val Tyr Gly Phe Ser Ser Gly Asn Phe Val Tyr Phe
            245                 250                 255

Leu Thr Leu Gln Pro Glu Met Val Ser Pro Gly Ser Thr Thr Lys
            260                 265                 270

Glu Gln Val Tyr Thr Ser Lys Leu Val Arg Leu Cys Lys Glu Asp Thr
        275                 280                 285

Ala Phe Asn Ser Tyr Val Glu Val Pro Ile Gly Cys Glu Arg Ser Gly
        290                 295                 300

Val Glu Tyr Arg Leu Leu Gln Ala Ala Tyr Leu Ser Lys Ala Gly Ala
305                 310                 315                 320

Val Leu Gly Arg Thr Leu Gly Val His Pro Asp Asp Asp Leu Leu Phe
            325                 330                 335

Thr Val Phe Ser Lys Gly Gln Lys Arg Lys Met Lys Ser Leu Asp Glu
            340                 345                 350

Ser Ala Leu Cys Ile Phe Ile Leu Lys Gln Ile Asn Asp Arg Ile Lys
        355                 360                 365

Glu Arg Leu Gln Ser Cys Tyr Arg Gly Glu Gly Thr Leu Asp Leu Ala
        370                 375                 380

Trp Leu Lys Val Lys Asp Ile Pro Cys Ser Ser Ala Leu Leu Thr Ile
385                 390                 395                 400

Asp Asp Asn Phe Cys Gly Leu Asp Met Asn Ala Pro Leu Gly Val Ser
            405                 410                 415

Asp Met Val Arg Gly Ile Pro Val Phe Thr Glu Asp Arg Asp Arg Met
            420                 425                 430

Thr Ser Val Ile Ala Tyr Val Tyr Lys Asn His Ser Leu Ala Phe Val
        435                 440                 445

Gly Thr Lys Ser Gly Lys Leu Lys Lys Ser Phe Gly Thr Gly Pro Gln
        450                 455                 460

Gly Gly Ile Thr Gln Glu Trp Ile Gly Val Glu Gly Asp Pro Pro Gly
465                 470                 475                 480

Ala Asn Ile Ala Ser Gln Glu Gln Met Leu Cys Val Tyr Leu Gln Cys
            485                 490                 495

Ser Ser His Lys Ala Ile Ser Asp Gln Arg Val Gln Pro Leu Leu Cys
            500                 505                 510

Cys Phe Leu Asn Val Pro Gly Asn Ser Ser
            515                 520
```

<210> SEQ ID NO 25
<211> LENGTH: 1925
<212> TYPE: PRT
<213> ORGANISM: Homo sapiens

<400> SEQUENCE: 25

```
Met Ala Pro Arg Ala Ala Gly Gly Ala Pro Leu Ser Arg Ala Ala
1               5                   10                  15
```

-continued

```
Ala Ala Ser Pro Pro Phe Gln Thr Pro Pro Arg Cys Pro Val Pro
             20              25              30
Leu Leu Leu Leu Leu Leu Leu Gly Ala Arg Ala Gly Ala Leu Glu
         35              40              45
Ile Gln Arg Arg Phe Pro Ser Pro Thr Pro Thr Asn Asn Phe Ala Leu
 50              55              60
Asp Gly Ala Ala Gly Thr Val Tyr Leu Ala Ala Val Asn Arg Leu Tyr
 65              70              75              80
Gln Leu Ser Gly Ala Asn Leu Ser Leu Glu Ala Glu Ala Ala Val Gly
             85              90              95
Pro Val Pro Asp Ser Pro Leu Cys His Ala Pro Gln Leu Pro Gln Ala
             100             105             110
Ser Cys Glu His Pro Arg Arg Leu Thr Asp Asn Tyr Asn Lys Ile Leu
             115             120             125
Gln Leu Asp Pro Gly Gln Gly Leu Val Val Val Cys Gly Ser Ile Tyr
             130             135             140
Gln Gly Phe Cys Gln Leu Arg Arg Arg Gly Asn Ile Ser Ala Val Ala
 145             150             155             160
Val Arg Phe Pro Ala Ala Pro Pro Ala Glu Pro Val Thr Val Phe
                 165             170             175
Pro Ser Met Leu Asn Val Ala Ala Asn His Pro Asn Ala Ser Thr Val
                 180             185             190
Gly Leu Val Leu Pro Pro Ala Gly Ala Gly Gly Ser Arg Leu Leu
                 195             200             205
Val Gly Ala Thr Tyr Thr Gly Tyr Gly Ser Ser Phe Phe Pro Arg Asn
 210             215             220
Arg Ser Leu Glu Asp His Arg Phe Glu Asn Thr Pro Glu Ile Ala Ile
 225             230             235             240
Arg Ser Leu Asp Thr Arg Gly Asp Leu Ala Lys Leu Phe Thr Phe Asp
                 245             250             255
Leu Asn Pro Ser Asp Asp Asn Ile Leu Lys Ile Lys Gln Gly Ala Lys
                 260             265             270
Glu Gln His Lys Leu Gly Phe Val Ser Ala Phe Leu His Pro Ser Asp
             275             280             285
Pro Pro Pro Gly Ala Gln Ser Tyr Ala Tyr Leu Ala Leu Asn Ser Glu
 290             295             300
Ala Arg Ala Gly Asp Lys Glu Ser Gln Ala Arg Ser Leu Leu Ala Arg
 305             310             315             320
Ile Cys Leu Pro His Gly Ala Gly Gly Asp Ala Lys Lys Leu Thr Glu
                 325             330             335
Ser Tyr Ile Gln Leu Gly Leu Gly Cys Ala Gly Gly Ala Gly Arg Gly
             340             345             350
Asp Leu Tyr Ser Arg Leu Val Ser Val Phe Pro Ala Arg Glu Arg Leu
             355             360             365
Phe Ala Val Phe Glu Arg Pro Gln Gly Ser Pro Ala Ala Arg Ala Ala
 370             375             380
Pro Ala Ala Leu Cys Ala Phe Arg Phe Ala Asp Val Arg Ala Ala Ile
 385             390             395             400
Arg Ala Ala Arg Thr Ala Cys Phe Val Glu Pro Ala Pro Asp Val Val
                 405             410             415
Ala Val Leu Asp Ser Val Val Gln Gly Thr Gly Pro Ala Cys Glu Arg
                 420             425             430
Lys Leu Asn Ile Gln Leu Gln Pro Glu Gln Leu Asp Cys Gly Ala Ala
             435             440             445
```

```
His Leu Gln His Pro Leu Ser Ile Leu Gln Pro Lys Ala Thr Pro
    450                 455                 460

Val Phe Arg Ala Pro Gly Leu Thr Ser Val Ala Val Ala Ser Val Asn
465                 470                 475                 480

Asn Tyr Thr Ala Val Phe Leu Gly Thr Val Asn Gly Arg Leu Leu Lys
                    485                 490                 495

Ile Asn Leu Asn Glu Ser Met Gln Val Val Ser Arg Arg Val Val Thr
                500                 505                 510

Val Ala Tyr Gly Glu Pro Val His His Val Met Gln Phe Asp Pro Ala
            515                 520                 525

Asp Ser Gly Tyr Leu Tyr Leu Met Thr Ser His Gln Met Ala Arg Val
            530                 535                 540

Lys Val Ala Ala Cys Asn Val His Ser Thr Cys Gly Asp Cys Val Gly
545                 550                 555                 560

Ala Ala Asp Ala Tyr Cys Gly Trp Cys Ala Leu Glu Thr Arg Cys Thr
                565                 570                 575

Leu Gln Gln Asp Cys Thr Asn Ser Ser Gln Gln His Phe Trp Thr Ser
                580                 585                 590

Ala Ser Glu Gly Pro Ser Arg Cys Pro Ala Met Thr Val Leu Pro Ser
            595                 600                 605

Glu Ile Asp Val Arg Gln Glu Tyr Pro Gly Met Ile Leu Gln Ile Ser
610                 615                 620

Gly Ser Leu Pro Ser Leu Ser Gly Met Glu Met Ala Cys Asp Tyr Gly
625                 630                 635                 640

Asn Asn Ile Arg Thr Val Ala Arg Val Pro Gly Pro Ala Phe Gly His
                645                 650                 655

Gln Ile Ala Tyr Cys Asn Leu Leu Pro Arg Asp Gln Phe Pro Pro Phe
                660                 665                 670

Pro Pro Asn Gln Asp His Val Thr Val Glu Met Ser Val Arg Val Asn
            675                 680                 685

Gly Arg Asn Ile Val Lys Ala Asn Phe Thr Ile Tyr Asp Cys Ser Arg
    690                 695                 700

Thr Ala Gln Val Tyr Pro His Thr Ala Cys Thr Ser Cys Leu Ser Ala
705                 710                 715                 720

Gln Trp Pro Cys Phe Trp Cys Ser Gln Gln His Ser Cys Val Ser Asn
                725                 730                 735

Gln Ser Arg Cys Glu Ala Ser Pro Asn Pro Thr Ser Pro Gln Asp Cys
                740                 745                 750

Pro Arg Thr Leu Leu Ser Pro Leu Ala Pro Val Pro Thr Gly Gly Ser
            755                 760                 765

Gln Asn Ile Leu Val Pro Leu Ala Asn Thr Ala Phe Phe Gln Gly Ala
            770                 775                 780

Ala Leu Glu Cys Ser Phe Gly Leu Glu Glu Ile Phe Glu Ala Val Trp
785                 790                 795                 800

Val Asn Glu Ser Val Val Arg Cys Asp Gln Val Val Leu His Thr Thr
                805                 810                 815

Arg Lys Ser Gln Val Phe Pro Leu Ser Leu Gln Leu Lys Gly Arg Pro
                820                 825                 830

Ala Arg Phe Leu Asp Ser Pro Glu Pro Met Thr Val Met Val Tyr Asn
                835                 840                 845

Cys Ala Met Gly Ser Pro Asp Cys Ser Gln Cys Leu Gly Arg Glu Asp
850                 855                 860

Leu Gly His Leu Cys Met Trp Ser Asp Gly Cys Arg Leu Arg Gly Pro
```

-continued

```
            865                 870                 875                 880
Leu Gln Pro Met Ala Gly Thr Cys Pro Ala Pro Glu Ile Arg Ala Ile
                    885                 890                 895
Glu Pro Leu Ser Gly Pro Leu Asp Gly Gly Thr Leu Leu Thr Ile Arg
                    900                 905                 910
Gly Arg Asn Leu Gly Arg Arg Leu Ser Asp Val Ala His Gly Val Trp
                    915                 920                 925
Ile Gly Gly Val Ala Cys Glu Pro Leu Pro Asp Arg Tyr Thr Val Ser
            930                 935                 940
Glu Glu Ile Val Cys Val Thr Gly Pro Ala Pro Gly Pro Leu Ser Gly
945                 950                 955                 960
Val Val Thr Val Asn Ala Ser Lys Gly Lys Ser Arg Asp Arg Phe
                    965                 970                 975
Ser Tyr Val Leu Pro Leu Val His Ser Leu Glu Pro Thr Met Gly Pro
                    980                 985                 990
Lys Ala Gly Gly Thr Arg Ile Thr Ile His Gly Asn Asp Leu His Val
                    995                 1000                1005
Gly Ser Glu Leu Gln Val Leu Val Asn Asp Thr Asp Pro Cys Thr
        1010            1015                1020
Glu Leu Met Arg Thr Asp Thr Ser Ile Ala Cys Thr Met Pro Glu
        1025            1030                1035
Gly Ala Leu Pro Ala Pro Val Pro Val Cys Val Arg Phe Glu Arg
        1040            1045                1050
Arg Gly Cys Val His Gly Asn Leu Thr Phe Trp Tyr Met Gln Asn
        1055            1060                1065
Pro Val Ile Thr Ala Ile Ser Pro Arg Arg Ser Pro Val Ser Gly
        1070            1075                1080
Gly Arg Thr Ile Thr Val Ala Gly Glu Arg Phe His Met Val Gln
        1085            1090                1095
Asn Val Ser Met Ala Val His His Ile Gly Arg Glu Pro Thr Leu
        1100            1105                1110
Cys Lys Val Leu Asn Ser Thr Leu Ile Thr Cys Pro Ser Pro Gly
        1115            1120                1125
Ala Leu Ser Asn Ala Ser Ala Pro Val Asp Phe Phe Ile Asn Gly
        1130            1135                1140
Arg Ala Tyr Ala Asp Glu Val Ala Val Ala Glu Glu Leu Leu Asp
        1145            1150                1155
Pro Glu Glu Ala Gln Arg Gly Ser Arg Phe Arg Leu Asp Tyr Leu
        1160            1165                1170
Pro Asn Pro Gln Phe Ser Thr Ala Lys Arg Glu Lys Trp Ile Lys
        1175            1180                1185
His His Pro Gly Glu Pro Leu Thr Leu Val Ile His Lys Glu Gln
        1190            1195                1200
Asp Ser Leu Gly Leu Gln Ser His Glu Tyr Arg Val Lys Ile Gly
        1205            1210                1215
Gln Val Ser Cys Asp Ile Gln Ile Val Ser Asp Arg Ile Ile His
        1220            1225                1230
Cys Ser Val Asn Glu Ser Leu Gly Ala Ala Val Gly Gln Leu Pro
        1235            1240                1245
Ile Thr Ile Gln Val Gly Asn Phe Asn Gln Thr Ile Ala Thr Leu
        1250            1255                1260
Gln Leu Gly Gly Ser Glu Thr Ala Ile Ile Val Ser Ile Val Ile
        1265            1270                1275
```

```
Cys Ser Val Leu Leu Leu Leu Ser Val Val Ala Leu Phe Val Phe
    1280              1285              1290

Cys Thr Lys Ser Arg Arg Ala Glu Arg Tyr Trp Gln Lys Thr Leu
    1295              1300              1305

Leu Gln Met Glu Glu Met Glu Ser Gln Ile Arg Glu Glu Ile Arg
    1310              1315              1320

Lys Gly Phe Ala Glu Leu Gln Thr Asp Met Thr Asp Leu Thr Lys
    1325              1330              1335

Glu Leu Asn Arg Ser Gln Gly Ile Pro Phe Leu Glu Tyr Lys His
    1340              1345              1350

Phe Val Thr Arg Thr Phe Phe Pro Lys Cys Ser Ser Leu Tyr Glu
    1355              1360              1365

Glu Arg Tyr Val Leu Pro Ser Gln Thr Leu Asn Ser Gln Gly Ser
    1370              1375              1380

Ser Gln Ala Gln Glu Thr His Pro Leu Leu Gly Glu Trp Lys Ile
    1385              1390              1395

Pro Glu Ser Cys Arg Pro Asn Met Glu Glu Gly Ile Ser Leu Phe
    1400              1405              1410

Ser Ser Leu Leu Asn Asn Lys His Phe Leu Ile Val Phe Val His
    1415              1420              1425

Ala Leu Glu Gln Gln Lys Asp Phe Ala Val Arg Asp Arg Cys Ser
    1430              1435              1440

Leu Ala Ser Leu Leu Thr Ile Ala Leu His Gly Lys Leu Glu Tyr
    1445              1450              1455

Tyr Thr Ser Ile Met Lys Glu Leu Leu Val Asp Leu Ile Asp Ala
    1460              1465              1470

Ser Ala Ala Lys Asn Pro Lys Leu Met Leu Arg Arg Thr Glu Ser
    1475              1480              1485

Val Val Glu Lys Met Leu Thr Asn Trp Met Ser Ile Cys Met Tyr
    1490              1495              1500

Ser Cys Leu Arg Glu Thr Val Gly Glu Pro Phe Phe Leu Leu Leu
    1505              1510              1515

Cys Ala Ile Lys Gln Gln Ile Asn Lys Gly Ser Ile Asp Ala Ile
    1520              1525              1530

Thr Gly Lys Ala Arg Tyr Thr Leu Asn Glu Glu Trp Leu Leu Arg
    1535              1540              1545

Glu Asn Ile Glu Ala Lys Pro Arg Asn Leu Asn Val Ser Phe Gln
    1550              1555              1560

Gly Cys Gly Met Asp Ser Leu Ser Val Arg Ala Met Asp Thr Asp
    1565              1570              1575

Thr Leu Thr Gln Val Lys Glu Lys Ile Leu Glu Ala Phe Cys Lys
    1580              1585              1590

Asn Val Pro Tyr Ser Gln Trp Pro Arg Ala Glu Asp Val Asp Leu
    1595              1600              1605

Glu Trp Phe Ala Ser Ser Thr Gln Ser Tyr Ile Leu Arg Asp Leu
    1610              1615              1620

Asp Asp Thr Ser Val Val Glu Asp Gly Arg Lys Lys Leu Asn Thr
    1625              1630              1635

Leu Ala His Tyr Lys Ile Pro Glu Gly Ala Ser Leu Ala Met Ser
    1640              1645              1650

Leu Ile Asp Lys Lys Asp Asn Thr Leu Gly Arg Val Lys Asp Leu
    1655              1660              1665

Asp Thr Glu Lys Tyr Phe His Leu Val Leu Pro Thr Asp Glu Leu
    1670              1675              1680
```

-continued

Ala Glu Pro Lys Lys Ser His Arg Gln Ser His Arg Lys Lys Val
    1685                1690                1695

Leu Pro Glu Ile Tyr Leu Thr Arg Leu Leu Ser Thr Lys Gly Thr
    1700                1705                1710

Leu Gln Lys Phe Leu Asp Asp Leu Phe Lys Ala Ile Leu Ser Ile
    1715                1720                1725

Arg Glu Asp Lys Pro Pro Leu Ala Val Lys Tyr Phe Phe Asp Phe
    1730                1735                1740

Leu Glu Glu Gln Ala Glu Lys Arg Gly Ile Ser Asp Pro Asp Thr
    1745                1750                1755

Leu His Ile Trp Lys Thr Asn Ser Leu Pro Leu Arg Phe Trp Val
    1760                1765                1770

Asn Ile Leu Lys Asn Pro Gln Phe Val Phe Asp Ile Asp Lys Thr
    1775                1780                1785

Asp His Ile Asp Ala Cys Leu Ser Val Ile Ala Gln Ala Phe Ile
    1790                1795                1800

Asp Ala Cys Ser Ile Ser Asp Leu Gln Leu Gly Lys Asp Ser Pro
    1805                1810                1815

Thr Asn Lys Leu Leu Tyr Ala Lys Glu Ile Pro Glu Tyr Arg Lys
    1820                1825                1830

Ile Val Gln Arg Tyr Tyr Lys Gln Ile Gln Asp Met Thr Pro Leu
    1835                1840                1845

Ser Glu Gln Glu Met Asn Ala His Leu Ala Glu Ser Arg Lys
    1850                1855                1860

Tyr Gln Asn Glu Phe Asn Thr Asn Val Ala Met Ala Glu Ile Tyr
    1865                1870                1875

Lys Tyr Ala Lys Arg Tyr Arg Pro Gln Ile Met Ala Ala Leu Glu
    1880                1885                1890

Ala Asn Pro Thr Ala Arg Arg Thr Gln Leu Gln His Lys Phe Glu
    1895                1900                1905

Gln Val Val Ala Leu Met Glu Asp Asn Ile Tyr Glu Cys Tyr Ser
    1910                1915                1920

Glu Ala
    1925

<210> SEQ ID NO 26
<211> LENGTH: 771
<212> TYPE: PRT
<213> ORGANISM: Homo sapiens

<400> SEQUENCE: 26

Met Gly Trp Leu Thr Arg Ile Val Cys Leu Phe Trp Gly Val Leu
1               5                   10                  15

Thr Ala Arg Ala Asn Tyr Gln Asn Gly Lys Asn Asn Val Pro Arg Leu
    20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
                100                 105                 110

```
Glu Cys Ala Asn Phe Ile Lys Val Leu Lys Ala Tyr Asn Gln Thr His
            115                 120                 125
Leu Tyr Ala Cys Gly Thr Gly Ala Phe His Pro Ile Cys Thr Tyr Ile
            130                 135                 140
Glu Ile Gly His His Pro Glu Asp Asn Ile Phe Lys Leu Glu Asn Ser
145                 150                 155                 160
His Phe Glu Asn Gly Arg Gly Lys Ser Pro Tyr Asp Pro Lys Leu Leu
            165                 170                 175
Thr Ala Ser Leu Leu Ile Asp Gly Glu Leu Tyr Ser Gly Thr Ala Ala
            180                 185                 190
Asp Phe Met Gly Arg Asp Phe Ala Ile Phe Arg Thr Leu Gly His His
            195                 200                 205
His Pro Ile Arg Thr Glu Gln His Asp Ser Arg Trp Leu Asn Asp Pro
            210                 215                 220
Lys Phe Ile Ser Ala His Leu Ile Ser Glu Ser Asp Asn Pro Glu Asp
225                 230                 235                 240
Asp Lys Val Tyr Phe Phe Arg Glu Asn Ala Ile Asp Gly Glu His
            245                 250                 255
Ser Gly Lys Ala Thr His Ala Arg Ile Gly Gln Ile Cys Lys Asn Asp
            260                 265                 270
Phe Gly Gly His Arg Ser Leu Val Asn Lys Trp Thr Thr Phe Leu Lys
            275                 280                 285
Ala Arg Leu Ile Cys Ser Val Pro Gly Pro Asn Gly Ile Asp Thr His
            290                 295                 300
Phe Asp Glu Leu Gln Asp Val Phe Leu Met Asn Phe Lys Asp Pro Lys
305                 310                 315                 320
Asn Pro Val Val Tyr Gly Val Phe Thr Thr Ser Ser Asn Ile Phe Lys
            325                 330                 335
Gly Ser Ala Val Cys Met Tyr Ser Met Ser Asp Val Arg Arg Val Phe
            340                 345                 350
Leu Gly Pro Tyr Ala His Arg Asp Gly Pro Asn Tyr Gln Trp Val Pro
            355                 360                 365
Tyr Gln Gly Arg Val Pro Tyr Pro Arg Pro Gly Thr Cys Pro Ser Lys
            370                 375                 380
Thr Phe Gly Gly Phe Asp Ser Thr Lys Asp Leu Pro Asp Asp Val Ile
385                 390                 395                 400
Thr Phe Ala Arg Ser His Pro Ala Met Tyr Asn Pro Val Phe Pro Met
            405                 410                 415
Asn Asn Arg Pro Ile Val Ile Lys Thr Asp Val Asn Tyr Gln Phe Thr
            420                 425                 430
Gln Ile Val Val Asp Arg Val Asp Ala Glu Asp Gly Gln Tyr Asp Val
            435                 440                 445
Met Phe Ile Gly Thr Asp Val Gly Thr Val Leu Lys Val Val Ser Ile
450                 455                 460
Pro Lys Glu Thr Trp Tyr Asp Leu Glu Glu Val Leu Leu Glu Glu Met
465                 470                 475                 480
Thr Val Phe Arg Glu Pro Thr Ala Ile Ser Ala Met Glu Leu Ser Thr
            485                 490                 495
Lys Gln Gln Gln Leu Tyr Ile Gly Ser Thr Ala Gly Val Ala Gln Leu
            500                 505                 510
Pro Leu His Arg Cys Asp Ile Tyr Gly Lys Ala Cys Ala Glu Cys Cys
            515                 520                 525
Leu Ala Arg Asp Pro Tyr Cys Ala Trp Asp Gly Ser Ala Cys Ser Arg
```

```
                530                 535                 540
Tyr Phe Pro Thr Ala Lys Arg Thr Arg Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Arg Ile Ile Tyr Gly Val Glu Asn Ser Ser
                580                 585                 590

Thr Phe Leu Glu Cys Ser Pro Lys Ser Gln Arg Ala Leu Val Tyr Trp
                595                 600                 605

Gln Phe Gln Arg Arg Asn Glu Glu Arg Lys Glu Glu Ile Arg Val Asp
        610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
                645                 650                 655

Ile Gln Thr Leu Leu Lys Val Thr Leu Glu Val Ile Asp Thr Glu His
                660                 665                 670

Leu Glu Glu Leu Leu His Lys Asp Asp Gly Asp Gly Ser Lys Thr
        675                 680                 685

Lys Glu Met Ser Asn Ser Met Thr Pro Ser Gln Lys Val Trp Tyr Arg
690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
                740                 745                 750

Asn Lys Lys Gly Arg Asn Arg Arg Thr His Glu Phe Glu Arg Ala Pro
                755                 760                 765

Arg Ser Val
        770

<210> SEQ ID NO 27
<211> LENGTH: 748
<212> TYPE: PRT
<213> ORGANISM: Homo sapiens

<400> SEQUENCE: 27

Met Gly Arg Ala Gly Ala Ala Val Ile Pro Gly Leu Ala Leu Leu
1               5                   10                  15

Trp Ala Val Gly Leu Gly Ser Ala Ala Pro Ser Pro Arg Leu Arg
                20                  25                  30

Leu Ser Phe Gln Glu Leu Gln Ala Trp His Gly Leu Gln Thr Phe Ser
                35                  40                  45

Leu Glu Arg Thr Cys Cys Tyr Gln Ala Leu Leu Val Asp Glu Glu Arg
        50                  55                  60

Gly Arg Leu Phe Val Gly Ala Glu Asn His Val Ala Ser Leu Asn Leu
65                  70                  75                  80

Asp Asn Ile Ser Lys Arg Ala Lys Lys Leu Ala Trp Pro Ala Pro Val
                85                  90                  95

Glu Trp Arg Glu Glu Cys Asn Trp Ala Gly Lys Asp Ile Gly Thr Glu
                100                 105                 110

Cys Met Asn Phe Val Lys Leu Leu His Ala Tyr Asn Arg Thr His Leu
                115                 120                 125

Leu Ala Cys Gly Thr Gly Ala Phe His Pro Thr Cys Ala Phe Val Glu
```

```
            130                 135                 140
Val Gly His Arg Ala Glu Glu Pro Val Leu Arg Leu Asp Pro Gly Arg
145                 150                 155                 160

Ile Glu Asp Gly Lys Gly Lys Ser Pro Tyr Asp Pro Arg His Arg Ala
                165                 170                 175

Ala Ser Val Leu Val Gly Glu Glu Leu Tyr Ser Gly Val Ala Ala Asp
                180                 185                 190

Leu Met Gly Arg Asp Phe Thr Ile Phe Arg Ser Leu Gly Gln Arg Pro
                195                 200                 205

Ser Leu Arg Thr Glu Pro His Asp Ser Arg Trp Leu Asn Glu Pro Lys
                210                 215                 220

Phe Val Lys Val Phe Trp Ile Pro Glu Ser Glu Asn Pro Asp Asp Asp
225                 230                 235                 240

Lys Ile Tyr Phe Phe Arg Glu Thr Ala Val Glu Ala Ala Pro Pro Ala
                245                 250                 255

Leu Gly Arg Leu Ser Val Ser Arg Val Gly Gln Ile Cys Arg Asn Asp
                260                 265                 270

Val Gly Gly Gln Arg Ser Leu Val Asn Lys Trp Thr Thr Phe Leu Lys
275                 280                 285

Ala Arg Leu Val Cys Ser Val Pro Gly Val Glu Gly Asp Thr His Phe
290                 295                 300

Asp Gln Leu Gln Asp Val Phe Leu Leu Ser Arg Asp His Arg Thr
305                 310                 315                 320

Pro Leu Leu Tyr Ala Val Phe Ser Thr Ser Ser Ile Phe Gln Gly Ser
                325                 330                 335

Ala Val Cys Val Tyr Ser Met Asn Asp Val Arg Arg Ala Phe Leu Gly
                340                 345                 350

Pro Phe Ala His Lys Glu Gly Pro Met His Gln Trp Val Ser Tyr Gln
                355                 360                 365

Gly Arg Val Pro Tyr Pro Arg Pro Gly Met Cys Pro Ser Lys Thr Phe
                370                 375                 380

Gly Thr Phe Ser Ser Thr Lys Asp Phe Pro Asp Asp Val Ile Gln Phe
385                 390                 395                 400

Ala Arg Asn His Pro Leu Met Tyr Asn Ser Val Leu Pro Thr Gly Gly
                405                 410                 415

Arg Pro Leu Phe Leu Gln Val Gly Ala Asn Tyr Thr Phe Thr Gln Ile
                420                 425                 430

Ala Ala Asp Arg Val Ala Ala Asp Gly His Tyr Asp Val Leu Phe
                435                 440                 445

Ile Gly Thr Asp Val Gly Thr Val Leu Lys Val Ile Ser Val Pro Lys
450                 455                 460

Gly Ser Arg Pro Ser Ala Glu Gly Leu Leu Leu Glu Glu Leu His Val
465                 470                 475                 480

Phe Glu Asp Ser Ala Ala Val Thr Ser Met Gln Ile Ser Ser Lys Arg
                485                 490                 495

His Gln Leu Tyr Val Ala Ser Arg Ser Ala Val Ala Gln Ile Ala Leu
                500                 505                 510

His Arg Cys Ala Ala His Gly Arg Val Cys Thr Glu Cys Cys Leu Ala
                515                 520                 525

Arg Asp Pro Tyr Cys Ala Trp Asp Gly Val Ala Cys Thr Arg Phe Gln
                530                 535                 540

Pro Ser Ala Lys Arg Arg Phe Arg Arg Gln Asp Val Arg Asn Gly Asp
545                 550                 555                 560
```

```
Pro Ser Thr Leu Cys Ser Gly Asp Ser Ser Arg Pro Ala Leu Leu Glu
            565                 570                 575

His Lys Val Phe Gly Val Glu Gly Ser Ser Ala Phe Leu Glu Cys Glu
            580                 585                 590

Pro Arg Ser Leu Gln Ala Arg Val Glu Trp Thr Phe Gln Arg Ala Gly
            595                 600                 605

Val Thr Ala His Thr Gln Val Leu Ala Glu Glu Arg Thr Glu Arg Thr
            610                 615                 620

Ala Arg Gly Leu Leu Leu Arg Arg Leu Arg Arg Asp Ser Gly Val
625                 630                 635                 640

Tyr Leu Cys Ala Ala Val Glu Gln Gly Phe Thr Gln Pro Leu Arg Arg
            645                 650                 655

Leu Ser Leu His Val Leu Ser Ala Thr Gln Ala Glu Arg Leu Ala Arg
            660                 665                 670

Ala Glu Glu Ala Ala Pro Ala Ala Pro Pro Gly Pro Lys Leu Trp Tyr
            675                 680                 685

Arg Asp Phe Leu Gln Leu Val Glu Pro Gly Gly Gly Ser Ala Asn
            690                 695                 700

Ser Leu Arg Met Cys Arg Pro Gln Pro Ala Leu Gln Ser Leu Pro Leu
705                 710                 715                 720

Glu Ser Arg Arg Lys Gly Arg Asn Arg Thr His Ala Pro Glu Pro
            725                 730                 735

Arg Ala Glu Arg Gly Pro Arg Ser Ala Thr His Trp
            740                 745

<210> SEQ ID NO 28
<211> LENGTH: 751
<212> TYPE: PRT
<213> ORGANISM: Homo sapiens

<400> SEQUENCE: 28

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
            115                 120                 125

Val Cys Gly Ser Gly Ala Phe Ser Pro Val Cys Thr Tyr Leu Asn Arg
        130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190
```

-continued

```
Gly Thr Asp Ala Ala Ile Phe Arg Ser Leu Thr Lys Arg Asn Ala Val
            195                 200                 205

Arg Thr Asp Gln His Asn Ser Lys Trp Leu Ser Glu Pro Met Phe Val
        210                 215                 220

Asp Ala His Val Ile Pro Asp Gly Thr Asp Pro Asn Asp Ala Lys Val
225                 230                 235                 240

Tyr Phe Phe Lys Glu Lys Leu Thr Asp Asn Asn Arg Ser Thr Lys
            245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
        290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
            325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
        370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
            405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Leu Pro Thr
        450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
            485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
        530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
            565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
            595                 600                 605

Lys Asp Arg Arg Lys Glu Val Lys Leu Asn Glu Arg Ile Ile Ala Thr
610                 615                 620
```

```
Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
                660                 665                 670

Lys Trp Ser Pro Trp Thr Trp Ala Ser Ser Val Arg Ala Leu Pro Phe
                675                 680                 685

His Pro Lys Asp Ile Met Gly Ala Phe Ser His Ser Glu Met Gln Met
            690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
                740                 745                 750
```

<210> SEQ ID NO 29
<211> LENGTH: 777
<212> TYPE: PRT
<213> ORGANISM: Homo sapiens

<400> SEQUENCE: 29

```
Met Asn Ala Asn Lys Asp Glu Arg Leu Lys Ala Arg Ser Gln Asp Phe
1               5                   10                  15

His Leu Phe Pro Ala Leu Met Met Leu Ser Met Thr Met Leu Phe Leu
                20                  25                  30

Pro Val Thr Gly Thr Leu Lys Gln Asn Ile Pro Arg Leu Lys Leu Thr
                35                  40                  45

Tyr Lys Asp Leu Leu Leu Ser Asn Ser Cys Ile Pro Phe Leu Gly Ser
            50                  55                  60

Ser Glu Gly Leu Asp Phe Gln Thr Leu Leu Leu Asp Glu Glu Arg Gly
65              70                  75                  80

Arg Leu Leu Leu Gly Ala Lys Asp His Ile Phe Leu Leu Ser Leu Val
                85                  90                  95

Asp Leu Asn Lys Asn Phe Lys Lys Ile Tyr Trp Pro Ala Ala Lys Glu
                100                 105                 110

Arg Val Glu Leu Cys Lys Leu Ala Gly Lys Asp Ala Asn Thr Glu Cys
            115                 120                 125

Ala Asn Phe Ile Arg Val Leu Gln Pro Tyr Asn Lys Thr His Ile Tyr
130                 135                 140

Val Cys Gly Thr Gly Ala Phe His Pro Ile Cys Gly Tyr Ile Asp Leu
145                 150                 155                 160

Gly Val Tyr Lys Glu Asp Ile Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu Tyr Leu Tyr Ser Gly Thr Ala Ser Asp Phe
                195                 200                 205

Leu Gly Lys Asp Thr Ala Phe Thr Arg Ser Leu Gly Pro Thr His Asp
        210                 215                 220

His His Tyr Ile Arg Thr Asp Ile Ser Glu His Tyr Trp Leu Asn Gly
225                 230                 235                 240

Ala Lys Phe Ile Gly Thr Phe Phe Ile Pro Asp Thr Tyr Asn Pro Asp
                245                 250                 255
```

```
Asp Asp Lys Ile Tyr Phe Phe Arg Glu Ser Ser Gln Glu Gly Ser
            260                 265                 270

Thr Ser Asp Lys Thr Ile Leu Ser Arg Val Gly Arg Val Cys Lys Asn
        275                 280                 285

Asp Val Gly Gly Gln Arg Ser Leu Ile Asn Lys Trp Thr Thr Phe Leu
        290                 295                 300

Lys Ala Arg Leu Ile Cys Ser Ile Pro Gly Ser Asp Gly Ala Asp Thr
305                 310                 315                 320

Tyr Phe Asp Glu Leu Gln Asp Ile Tyr Leu Leu Pro Thr Arg Asp Glu
            325                 330                 335

Arg Asn Pro Val Val Tyr Gly Val Phe Thr Thr Thr Ser Ser Ile Phe
                340                 345                 350

Lys Gly Ser Ala Val Cys Val Tyr Ser Met Ala Asp Ile Arg Ala Val
            355                 360                 365

Phe Asn Gly Pro Tyr Ala His Lys Glu Ser Ala Asp His Arg Trp Val
        370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Lys Arg His Ser Val Met Tyr Lys Ser Val Tyr
            420                 425                 430

Pro Val Ala Gly Gly Pro Thr Phe Lys Arg Ile Asn Val Asp Tyr Arg
                435                 440                 445

Leu Thr Gln Ile Val Val Asp His Val Ile Ala Glu Asp Gly Gln Tyr
        450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
            485                 490                 495

Leu Gln Ile Phe Lys His Ser Ser Ile Ile Leu Asn Met Glu Leu Ser
            500                 505                 510

Leu Lys Gln Gln Gln Leu Tyr Ile Gly Ser Arg Asp Gly Leu Val Gln
        515                 520                 525

Leu Ser Leu His Arg Cys Asp Thr Tyr Gly Lys Ala Cys Ala Asp Cys
530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Arg Ala Arg Arg Gln Asp Val Lys
                565                 570                 575

Tyr Gly Asp Pro Ile Thr Gln Cys Trp Asp Ile Glu Asp Ser Ile Ser
            580                 585                 590

His Glu Thr Ala Asp Glu Lys Val Ile Phe Gly Ile Glu Phe Asn Ser
            595                 600                 605

Thr Phe Leu Glu Cys Ile Pro Lys Ser Gln Gln Ala Thr Ile Lys Trp
        610                 615                 620

Tyr Ile Gln Arg Ser Gly Asp Glu His Arg Glu Leu Lys Pro Asp
625                 630                 635                 640

Glu Arg Ile Ile Lys Thr Glu Tyr Gly Leu Leu Ile Arg Ser Leu Gln
                645                 650                 655

Lys Lys Asp Ser Gly Met Tyr Tyr Cys Lys Ala Gln Glu His Thr Phe
                660                 665                 670

Ile His Thr Ile Val Lys Leu Thr Leu Asn Val Ile Glu Asn Glu Gln
```

```
                        675                 680                 685
Met Glu Asn Thr Gln Arg Ala Glu His Glu Gly Lys Val Lys Asp
            690                 695                 700

Leu Leu Ala Glu Ser Arg Leu Arg Tyr Lys Asp Tyr Ile Gln Ile Leu
705                 710                 715                 720

Ser Ser Pro Asn Phe Ser Leu Asp Gln Tyr Cys Glu Gln Met Trp His
                        725                 730                 735

Arg Glu Lys Arg Arg Gln Arg Asn Lys Gly Gly Pro Lys Trp Lys His
                740                 745                 750

Met Gln Glu Met Lys Lys Lys Arg Asn Arg Arg His His Arg Asp Leu
            755                 760                 765

Asp Glu Leu Pro Arg Ala Val Ala Thr
        770                 775

<210> SEQ ID NO 30
<211> LENGTH: 775
<212> TYPE: PRT
<213> ORGANISM: Homo sapiens

<400> SEQUENCE: 30

Met Ala Ser Ala Gly His Ile Ile Thr Leu Leu Trp Gly Tyr Leu
1               5                   10                  15

Leu Glu Leu Trp Thr Gly Gly His Thr Ala Asp Thr Thr His Pro Arg
            20                  25                  30

Leu Arg Leu Ser His Lys Glu Leu Leu Asn Leu Asn Arg Thr Ser Ile
        35                  40                  45

Phe His Ser Pro Phe Gly Phe Leu Asp Leu His Thr Met Leu Leu Asp
    50                  55                  60

Glu Tyr Gln Glu Arg Leu Phe Val Gly Gly Arg Asp Leu Val Tyr Ser
65                  70                  75                  80

Leu Ser Leu Glu Arg Ile Ser Asp Gly Tyr Lys Glu Ile His Trp Pro
                85                  90                  95

Ser Thr Ala Leu Lys Met Glu Glu Cys Ile Met Lys Gly Lys Asp Ala
            100                 105                 110

Gly Glu Cys Ala Asn Tyr Val Arg Val Leu His His Tyr Asn Arg Thr
        115                 120                 125

His Leu Leu Thr Cys Gly Thr Gly Ala Phe Asp Pro Val Cys Ala Phe
    130                 135                 140

Ile Arg Val Gly Tyr His Leu Glu Asp Pro Leu Phe His Leu Glu Ser
145                 150                 155                 160

Pro Arg Ser Glu Arg Gly Arg Gly Arg Cys Pro Phe Asp Pro Ser Ser
                165                 170                 175

Ser Phe Ile Ser Thr Leu Ile Gly Ser Glu Leu Phe Ala Gly Leu Tyr
            180                 185                 190

Ser Asp Tyr Trp Ser Arg Asp Ala Ala Ile Phe Arg Ser Met Gly Arg
        195                 200                 205

Leu Ala His Ile Arg Thr Glu His Asp Asp Glu Arg Leu Leu Lys Glu
    210                 215                 220

Pro Lys Phe Val Gly Ser Tyr Met Ile Pro Asp Asn Glu Asp Arg Asp
225                 230                 235                 240

Asp Asn Lys Val Tyr Phe Phe Phe Thr Glu Lys Ala Leu Glu Ala Glu
                245                 250                 255

Asn Asn Ala His Ala Ile Tyr Thr Arg Val Gly Arg Leu Cys Val Asn
            260                 265                 270

Asp Val Gly Gly Gln Arg Ile Leu Val Asn Lys Trp Ser Thr Phe Leu
```

-continued

```
                275                 280                 285
Lys Ala Arg Leu Val Cys Ser Val Pro Gly Met Asn Gly Ile Asp Thr
            290                 295                 300
Tyr Phe Asp Glu Leu Glu Asp Val Phe Leu Leu Pro Thr Arg Asp His
305                 310                 315                 320
Lys Asn Pro Val Ile Phe Gly Leu Phe Asn Thr Thr Ser Asn Ile Phe
                325                 330                 335
Arg Gly His Ala Ile Cys Val Tyr His Met Ser Ser Ile Arg Ala Ala
            340                 345                 350
Phe Asn Gly Pro Tyr Ala His Lys Glu Gly Pro Glu Tyr His Trp Ser
            355                 360                 365
Val Tyr Glu Gly Lys Val Pro Tyr Pro Arg Pro Gly Ser Cys Ala Ser
    370                 375                 380
Lys Val Asn Gly Gly Arg Tyr Gly Thr Thr Lys Asp Tyr Pro Asp Asp
385                 390                 395                 400
Ala Ile Arg Phe Ala Arg Ser His Pro Leu Met Tyr Gln Ala Ile Lys
                405                 410                 415
Pro Ala His Lys Lys Pro Ile Leu Val Lys Thr Asp Gly Lys Tyr Asn
            420                 425                 430
Leu Lys Gln Ile Ala Val Asp Arg Val Glu Ala Glu Asp Gly Gln Tyr
        435                 440                 445
Asp Val Leu Phe Ile Gly Thr Asp Asn Gly Ile Val Leu Lys Val Ile
    450                 455                 460
Thr Ile Tyr Asn Gln Glu Met Glu Ser Met Glu Glu Val Ile Leu Glu
465                 470                 475                 480
Glu Leu Gln Ile Phe Lys Asp Pro Val Pro Ile Ile Ser Met Glu Ile
                485                 490                 495
Ser Ser Lys Arg Gln Gln Leu Tyr Ile Gly Ser Ala Ser Ala Val Ala
            500                 505                 510
Gln Val Arg Phe His His Cys Asp Met Tyr Gly Ser Ala Cys Ala Asp
            515                 520                 525
Cys Cys Leu Ala Arg Asp Pro Tyr Cys Ala Trp Asp Gly Ile Ser Cys
    530                 535                 540
Ser Arg Tyr Tyr Pro Thr Gly Thr His Ala Lys Arg Arg Phe Arg Arg
545                 550                 555                 560
Gln Asp Val Arg His Gly Asn Ala Ala Gln Cys Phe Gly Gln Gln
                565                 570                 575
Phe Val Gly Asp Ala Leu Asp Lys Thr Glu Glu His Leu Ala Tyr Gly
            580                 585                 590
Ile Glu Asn Asn Ser Thr Leu Leu Glu Cys Thr Pro Arg Ser Leu Gln
            595                 600                 605
Ala Lys Val Ile Trp Phe Val Gln Lys Gly Arg Glu Thr Arg Lys Glu
    610                 615                 620
Glu Val Lys Thr Asp Asp Arg Val Lys Met Asp Leu Gly Leu Leu
625                 630                 635                 640
Phe Leu Arg Leu His Lys Ser Asp Ala Gly Thr Tyr Phe Cys Gln Thr
                645                 650                 655
Val Glu His Ser Phe Val His Thr Val Arg Lys Ile Thr Leu Glu Val
            660                 665                 670
Val Glu Glu Glu Lys Val Glu Asp Met Phe Asn Lys Asp Glu Glu
            675                 680                 685
Asp Arg His His Arg Met Pro Cys Pro Ala Gln Ser Ser Ile Ser Gln
    690                 695                 700
```

```
Gly Ala Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
            725                 730                 735

Arg Lys Arg Lys Lys Leu Lys Met Ser Pro Ser Lys Trp Lys Tyr Ala
        740                 745                 750

Asn Pro Gln Glu Lys Lys Leu Arg Ser Lys Pro Glu His Tyr Arg Leu
    755                 760                 765

Pro Arg His Thr Leu Asp Ser
    770                 775

<210> SEQ ID NO 31
<211> LENGTH: 785
<212> TYPE: PRT
<213> ORGANISM: Homo sapiens

<400> SEQUENCE: 31

Met Leu Val Ala Gly Leu Leu Trp Ala Ser Leu Thr Gly Ala
1               5                   10                  15

Trp Pro Ser Phe Pro Thr Gln Asp His Leu Pro Ala Thr Pro Arg Val
            20                  25                  30

Arg Leu Ser Phe Lys Glu Leu Lys Ala Thr Gly Thr Ala His Phe Phe
        35                  40                  45

Asn Phe Leu Leu Asn Thr Thr Asp Tyr Arg Ile Leu Leu Lys Asp Glu
    50                  55                  60

Asp His Asp Arg Met Tyr Val Gly Ser Lys Asp Tyr Val Leu Ser Leu
65                  70                  75                  80

Asp Leu His Asp Ile Asn Arg Glu Pro Leu Ile Ile His Trp Ala Ala
                85                  90                  95

Ser Pro Gln Arg Ile Glu Glu Cys Val Leu Ser Gly Lys Asp Val Asn
            100                 105                 110

Gly Glu Cys Gly Asn Phe Val Arg Leu Ile Gln Pro Trp Asn Arg Thr
        115                 120                 125

His Leu Tyr Val Cys Gly Thr Gly Ala Tyr Asn Pro Met Cys Thr Tyr
    130                 135                 140

Val Asn Arg Gly Arg Arg Ala Gln Ala Thr Pro Trp Thr Gln Thr Gln
145                 150                 155                 160

Ala Val Arg Gly Arg Gly Ser Arg Ala Thr Asp Gly Ala Leu Arg Pro
                165                 170                 175

Met Pro Thr Ala Pro Arg Gln Asp Tyr Ile Phe Tyr Leu Glu Pro Glu
            180                 185                 190

Arg Leu Glu Ser Gly Lys Gly Lys Cys Pro Tyr Asp Pro Lys Leu Asp
        195                 200                 205

Thr Ala Ser Ala Leu Ile Asn Glu Glu Leu Tyr Ala Gly Val Tyr Ile
    210                 215                 220

Asp Phe Met Gly Thr Asp Ala Ala Ile Phe Arg Thr Leu Gly Lys Gln
225                 230                 235                 240

Thr Ala Met Arg Thr Asp Gln Tyr Asn Ser Arg Trp Leu Asn Asp Pro
                245                 250                 255

Ser Phe Ile His Ala Glu Leu Ile Pro Asp Ser Ala Glu Arg Asn Asp
            260                 265                 270

Asp Lys Leu Tyr Phe Phe Phe Arg Glu Arg Ser Ala Glu Ala Pro Gln
        275                 280                 285

Ser Pro Ala Val Tyr Ala Arg Ile Gly Arg Ile Cys Leu Asn Asp Asp
    290                 295                 300
```

-continued

```
Gly Gly His Cys Cys Leu Val Asn Lys Trp Ser Thr Phe Leu Lys Ala
305                 310                 315                 320

Arg Leu Val Cys Ser Val Pro Gly Glu Asp Gly Ile Glu Thr His Phe
                325                 330                 335

Asp Glu Leu Gln Asp Val Phe Val Gln Thr Gln Asp Val Arg Asn
                340                 345                 350

Pro Val Ile Tyr Ala Val Phe Thr Ser Ser Gly Ser Val Phe Arg Gly
                355                 360                 365

Ser Ala Val Cys Val Tyr Ser Met Ala Asp Ile Arg Met Val Phe Asn
370                 375                 380

Gly Pro Phe Ala His Lys Glu Gly Pro Asn Tyr Gln Trp Met Pro Phe
385                 390                 395                 400

Ser Gly Lys Met Pro Tyr Pro Arg Pro Gly Thr Cys Pro Gly Gly Thr
                405                 410                 415

Phe Thr Pro Ser Met Lys Ser Thr Lys Asp Tyr Pro Asp Glu Val Ile
                420                 425                 430

Asn Phe Met Arg Ser His Pro Leu Met Tyr Gln Ala Val Tyr Pro Leu
                435                 440                 445

Gln Arg Arg Pro Leu Val Val Arg Thr Gly Ala Pro Tyr Arg Leu Thr
450                 455                 460

Thr Ile Ala Val Asp Gln Val Asp Ala Ala Asp Gly Arg Tyr Glu Val
465                 470                 475                 480

Leu Phe Leu Gly Thr Asp Arg Gly Thr Val Gln Lys Val Ile Val Leu
                485                 490                 495

Pro Lys Asp Asp Gln Glu Leu Glu Glu Leu Met Leu Glu Glu Val Glu
                500                 505                 510

Val Phe Lys Asp Pro Ala Pro Val Lys Thr Met Thr Ile Ser Ser Lys
                515                 520                 525

Arg Gln Gln Leu Tyr Val Ala Ser Ala Val Gly Val Thr His Leu Ser
530                 535                 540

Leu His Arg Cys Gln Ala Tyr Gly Ala Ala Cys Ala Asp Cys Cys Leu
545                 550                 555                 560

Ala Arg Asp Pro Tyr Cys Ala Trp Asp Gly Gln Ala Cys Ser Arg Tyr
                565                 570                 575

Thr Ala Ser Ser Lys Arg Arg Ser Arg Arg Gln Asp Val Arg His Gly
                580                 585                 590

Asn Pro Ile Arg Gln Cys Arg Gly Phe Asn Ser Asn Ala Asn Lys Asn
                595                 600                 605

Ala Val Glu Ser Val Gln Tyr Gly Val Ala Gly Ser Ala Ala Phe Leu
                610                 615                 620

Glu Cys Gln Pro Arg Ser Pro Gln Ala Thr Val Lys Trp Leu Phe Gln
625                 630                 635                 640

Arg Asp Pro Gly Asp Arg Arg Glu Ile Arg Ala Glu Asp Arg Phe
                645                 650                 655

Leu Arg Thr Glu Gln Gly Leu Leu Leu Arg Ala Leu Gln Leu Ser Asp
                660                 665                 670

Arg Gly Leu Tyr Ser Cys Thr Ala Thr Glu Asn Asn Phe Lys His Val
                675                 680                 685

Val Thr Arg Val Gln Leu His Val Leu Gly Arg Asp Ala Val His Ala
                690                 695                 700

Ala Leu Phe Pro Pro Leu Ser Met Ser Ala Pro Pro Pro Gly Ala
705                 710                 715                 720

Gly Pro Pro Thr Pro Tyr Gln Glu Leu Ala Gln Leu Leu Ala Gln
                725                 730                 735
```

```
Pro Glu Val Gly Leu Ile His Gln Tyr Cys Gln Gly Tyr Trp Arg His
                740                 745                 750

Val Pro Pro Ser Pro Arg Glu Ala Pro Gly Ala Pro Arg Ser Pro Glu
            755                 760                 765

Pro Gln Asp Gln Lys Lys Pro Arg Asn Arg Arg His His Pro Pro Asp
770                 775                 780

Thr
785

<210> SEQ ID NO 32
<211> LENGTH: 782
<212> TYPE: PRT
<213> ORGANISM: Homo sapiens

<400> SEQUENCE: 32

Met Ala Pro Ser Ala Trp Ala Ile Cys Trp Leu Leu Gly Gly Leu Leu
1               5                   10                  15

Leu His Gly Gly Ser Ser Gly Pro Ser Pro Gly Pro Ser Val Pro Arg
            20                  25                  30

Leu Arg Leu Ser Tyr Arg Asp Leu Leu Ser Ala Asn Arg Ser Ala Ile
        35                  40                  45

Phe Leu Gly Pro Gln Gly Ser Leu Asn Leu Gln Ala Met Tyr Leu Asp
    50                  55                  60

Glu Tyr Arg Asp Arg Leu Phe Leu Gly Gly Leu Asp Ala Leu Tyr Ser
65                  70                  75                  80

Leu Arg Leu Asp Gln Ala Trp Pro Asp Pro Arg Glu Val Leu Trp Pro
                85                  90                  95

Pro Gln Pro Gly Gln Arg Glu Glu Cys Val Arg Lys Gly Arg Asp Pro
            100                 105                 110

Leu Thr Glu Cys Ala Asn Phe Val Arg Val Leu Gln Pro His Asn Arg
        115                 120                 125

Thr His Leu Leu Ala Cys Gly Thr Gly Ala Phe Gln Pro Thr Cys Ala
    130                 135                 140

Leu Ile Thr Val Gly His Arg Gly Glu His Val Leu His Leu Glu Pro
145                 150                 155                 160

Gly Ser Val Glu Ser Gly Arg Gly Arg Cys Pro His Glu Pro Ser Arg
                165                 170                 175

Pro Phe Ala Ser Thr Phe Ile Asp Gly Glu Leu Tyr Thr Gly Leu Thr
            180                 185                 190

Ala Asp Phe Leu Gly Arg Glu Ala Met Ile Phe Arg Ser Gly Gly Pro
        195                 200                 205

Arg Pro Ala Leu Arg Ser Asp Ser Asp Gln Ser Leu Leu His Asp Pro
    210                 215                 220

Arg Phe Val Met Ala Ala Arg Ile Pro Glu Asn Ser Asp Gln Asp Asn
225                 230                 235                 240

Asp Lys Val Tyr Phe Phe Ser Glu Thr Val Pro Ser Pro Asp Gly
                245                 250                 255

Gly Ser Asn His Val Thr Val Ser Arg Val Gly Arg Val Cys Val Asn
            260                 265                 270

Asp Ala Gly Gly Gln Arg Val Leu Val Asn Lys Trp Ser Thr Phe Leu
        275                 280                 285

Lys Ala Arg Leu Val Cys Ser Val Pro Gly Pro Gly Gly Ala Glu Thr
    290                 295                 300

His Phe Asp Gln Leu Glu Asp Val Phe Leu Leu Trp Pro Lys Ala Gly
305                 310                 315                 320
```

```
Lys Ser Leu Glu Val Tyr Ala Leu Phe Ser Thr Val Ser Ala Val Phe
                325                 330                 335

Gln Gly Phe Ala Val Cys Val Tyr His Met Ala Asp Ile Trp Glu Val
                340                 345                 350

Phe Asn Gly Pro Phe Ala His Arg Asp Gly Pro Gln His Gln Trp Gly
                355                 360                 365

Pro Tyr Gly Gly Lys Val Pro Phe Pro Arg Pro Gly Val Cys Pro Ser
                370                 375                 380

Lys Met Thr Ala Gln Pro Gly Arg Pro Phe Gly Ser Thr Lys Asp Tyr
385                 390                 395                 400

Pro Asp Glu Val Leu Gln Phe Ala Arg Ala His Pro Leu Met Phe Trp
                405                 410                 415

Pro Val Arg Pro Arg His Gly Arg Pro Val Leu Val Lys Thr His Leu
                420                 425                 430

Ala Gln Gln Leu His Gln Ile Val Val Asp Arg Val Glu Ala Glu Asp
                435                 440                 445

Gly Thr Tyr Asp Val Ile Phe Leu Gly Thr Asp Ser Gly Ser Val Leu
                450                 455                 460

Lys Val Ile Ala Leu Gln Ala Gly Gly Ser Ala Glu Pro Glu Glu Val
465                 470                 475                 480

Val Leu Glu Glu Leu Gln Val Phe Lys Val Pro Thr Pro Ile Thr Glu
                485                 490                 495

Met Glu Ile Ser Val Lys Arg Gln Met Leu Tyr Val Gly Ser Arg Leu
                500                 505                 510

Gly Val Ala Gln Leu Arg Leu His Gln Cys Glu Thr Tyr Gly Thr Ala
                515                 520                 525

Cys Ala Glu Cys Cys Leu Ala Arg Asp Pro Tyr Cys Ala Trp Asp Gly
                530                 535                 540

Ala Ser Cys Thr His Tyr Arg Pro Ser Leu Gly Lys Arg Arg Phe Arg
545                 550                 555                 560

Arg Gln Asp Ile Arg His Gly Asn Pro Ala Leu Gln Cys Leu Gly Gln
                565                 570                 575

Ser Gln Glu Glu Glu Ala Val Gly Leu Val Ala Ala Thr Met Val Tyr
                580                 585                 590

Gly Thr Glu His Asn Ser Thr Phe Leu Glu Cys Leu Pro Lys Ser Pro
                595                 600                 605

Gln Ala Ala Val Arg Trp Leu Leu Gln Arg Pro Gly Asp Glu Gly Pro
610                 615                 620

Asp Gln Val Lys Thr Asp Glu Arg Val Leu His Thr Glu Arg Gly Leu
625                 630                 635                 640

Leu Phe Arg Arg Leu Ser Arg Phe Asp Ala Gly Thr Tyr Thr Cys Thr
                645                 650                 655

Thr Leu Glu His Gly Phe Ser Gln Thr Val Val Arg Leu Ala Leu Val
                660                 665                 670

Val Ile Val Ala Ser Gln Leu Asp Asn Leu Phe Pro Pro Glu Pro Lys
                675                 680                 685

Pro Glu Glu Pro Pro Ala Arg Gly Gly Leu Ala Ser Thr Pro Pro Lys
                690                 695                 700

Ala Trp Tyr Lys Asp Ile Leu Gln Leu Ile Gly Phe Ala Asn Leu Pro
705                 710                 715                 720

Arg Val Asp Glu Tyr Cys Glu Arg Val Trp Cys Arg Gly Thr Thr Glu
                725                 730                 735

Cys Ser Gly Cys Phe Arg Ser Arg Ser Arg Gly Lys Gln Ala Arg Gly
```

```
                740                 745                 750
Lys Ser Trp Ala Gly Leu Glu Leu Gly Lys Lys Met Lys Ser Arg Val
        755                 760                 765
His Ala Glu His Asn Arg Thr Pro Arg Glu Val Glu Ala Thr
    770                 775                 780

<210> SEQ ID NO 33
<211> LENGTH: 2334
<212> TYPE: DNA
<213> ORGANISM: Homo sapiens

<400> SEQUENCE: 33
atgaatgcta ataaagatga aagacttaaa gccagaagcc aagattttca ccttttttcct    60 gctttgatga tgctaagcat gaccatgttg tttcttccag tcactggcac tttgaagcaa   120
aatattccaa gactcaagct aacctacaaa gacttgctgc tttcaaatag ctgtattccc   180
tttttgggtt catcagaagg actggatttt caaactcttc tcttagatga ggaaagaggc   240
aggctgctct gggagccaa agaccacatc tttctactca gtctggttga cttaaacaaa   300
aattttaaga gatttattg gcctgctgca aggaacggg tggaattatg taaattagct   360
gggaaagatg ccaatacaga atgtgcaaat ttcatcagag tacttcagcc ctataacaaa   420
actcacatat atgtgtgtgg aactggagca tttcatccaa tatgtgggta tattgatctt   480
ggagtctaca aggaggatat atattcaaa ctagacacac ataatttgga gtctggcaga   540
ctgaaatgtc ctttcgatcc tcagcagcct tttgcttcag taatgacaga tgagtacctc   600
tactctggaa cagcttctga tttccttggc aaagatactg cattcactcg atcccttggg   660
cctactcatg accaccacta catcagaact gacatttcag agcactactg gctcaatgga   720
gcaaaattta ttggaacttt cttcatacca gacacctaca atccagatga tgataaaata   780
tatttcttct ttcgtgaatc atctcaagaa ggcagtacct ccgataaaac catcctttct   840
cgagttggaa gagtttgtaa gaatgatgta ggaggacaac gcagcctgat aaacaagtgg   900 acgactttc ttaaggccag actgatttgc tcaattcctg aagtgatgg ggcagatact   960 tactttgatg agcttcaaga tatttattta ctccccacaa gagatgaaag aaatcctgta  1020
gtatatggag tctttactac aaccagctcc atcttcaaag ctctgctgt ttgtgtgtat  1080 agcatggctg acatcagagc agttttttaat ggtccatatg ctcataagga aagtgcagac  1140
catcgttggg tgcagtatga tgggagaatt ccttatccac ggcctggtac atgtccaagc  1200
aaaacctatg acccactgat taagtccacc cgagattttc agatgatgt catcagtttc  1260 ataaagcggc actctgtgat gtataagtcc gtataccag ttgcaggagg accaacgttc  1320
aagagaatca atgtggatta cagactgaca cagatagtgg tggatcatgt cattgcagaa  1380
gatggccagt acgatgtaat gtttcttgga acagacattg gaactgtcct caaagttgtc  1440
agcatttcaa aggaaaagtg gaatatgaa gaggtagtgc tggaggagtt gcagatattc  1500
aagcactcat caatcatctt gaacatggaa ttgtctctga gcagcaaca attgtacatt  1560 ggttcccgag atggattggt tcagctctcc ttgcacagat gcgacactta tgggaaagct  1620
tgcgcagact gttgtcttgc cagagacccc tactgtgcct gggatggaaa tgcatgctct  1680
cgatatgctc ctacttctaa aaggaaagct aagaaacaag atgtaaaata tggcgaccca  1740
atcacccagt gctgggacat cgaagacagc attagtcatg aaactgctga tgaaaaggtg  1800
atttttggca ttgaatttaa ctcaaccttt ctggaatgta tacctaaatc ccaacaagca  1860
actattaaat ggtatatcca gaggtcaggg gatgagcatc gagaggagtt gaagcccgat  1920
```

-continued

| | |
|---|---|
| gaaagaatca tcaaaacgga atatgggcta ctgattcgaa gtttgcagaa gaaggattct | 1980 |
| gggatgtatt actgcaaagc ccaggagcac actttcatcc acaccatagt gaagctgact | 2040 |
| ttgaatgtca ttgagaatga acagatggaa aatacccaga gggcagagca tgaggagggg | 2100 |
| aaggtcaagg atctattggc tgagtcacgg ttgagataca aagactacat ccaaatcctt | 2160 |
| agcagcccaa acttcagcct cgaccagtac tgcgaacaga tgtggcacag ggagaagcgg | 2220 |
| agacagagaa acaaggggggg cccaaagtgg aagcacatgc aggaaatgaa gaagaaacga | 2280 |
| aatcgaagac atcacagaga cctggatgag ctccctagag ctgtagccac gtag | 2334 |

<210> SEQ ID NO 34
<211> LENGTH: 2328
<212> TYPE: DNA
<213> ORGANISM: Homo sapiens

<400> SEQUENCE: 34

| | |
|---|---|
| atggcatccg cggggcacat tatcaccttg ctcctgtggg gttacttact ggagctttgg | 60 |
| acaggaggtc atacagctga tactacccac ccccggttac gcctgtcaca taaagagctc | 120 |
| ttgaatctga acagaacatc aatatttcat agccctttg gatttcttga tctccataca | 180 |
| atgctgctgg atgaatatca agagaggctc ttcgtgggag gcagggacct tgtatattcc | 240 |
| ctcagcttgg agagaatcag tgacggctat aaagagatac actggccgag tacagctcta | 300 |
| aaaatggaag aatgcataat gaagggaaaa gatgcgggtg aatgtgcaaa ttatgttcgg | 360 |
| gttttgcatc actataacag gacacacctt ctgacctgtg gtactggagc ttttgatcca | 420 |
| gtttgtgcct tcatcagagt tggatatcat ttggaggatc ctctgtttca cctggaatca | 480 |
| cccagatctg agagaggaag gggcagatgt ccttttgacc ccagctcctc cttcatctcc | 540 |
| actttaattg gtagtgaatt gtttgctgga ctctacagtg actactggag cagagacgct | 600 |
| gcgatcttcc gcagcatggg gcgactggcc catatccgca ctgagcatga cgatgagcgt | 660 |
| ctgttgaaag aaccaaaatt tgtaggttca tacatgattc ctgacaatga agacagagat | 720 |
| gacaacaaag tatatttctt ttttactgag aaggcactgg aggcagaaaa caatgctcac | 780 |
| gcaatttaca ccagggtcgg gcgactctgt gtgaatgatg taggagggca gagaatactg | 840 |
| gtgaataagt ggagcacttt cctaaaagcg agactcgttt gctcagtacc aggaatgaat | 900 |
| ggaattgaca catattttga tgaattagag acgttttttt gctacctac cagagatcat | 960 |
| aagaatccag tgatatttgg actctttaac actaccagta atattttcg agggcatgct | 1020 |
| atatgtgtct atcacatgtc tagcattcgg gcagccttca acggaccata tgcacataag | 1080 |
| gaaggacctg aataccactg gtcagtctat gaaggaaaag tcccttatcc aaggcctggt | 1140 |
| tcttgtgcca gcaaagtaaa tggagggaga tacggaacca ccaaggacta tcctgatgat | 1200 |
| gccatccgat ttgcaagaag tcatccacta atgtaccagg ccataaaacc tgcccataaa | 1260 |
| aaaccaatat tggtaaaaac agatggaaaa tataacctga acaaatagc agtagatcga | 1320 |
| gtggaagctg aggatggcca atatgacgtc ttgtttattg ggacagataa tggaattgtg | 1380 |
| ctgaaagtaa tcacaattta caaccaagaa atggaatcaa tggaagaagt aattctagaa | 1440 |
| gaacttcaga tattcaagga tccagttcct attatttcta tggagatttc ttcaaaacgg | 1500 |
| caacagctgt atattggatc tgcttctgct gtggctcaag tcagattcca tcactgtgac | 1560 |
| atgtatggaa gtgcttgtgc tgactgctgc ctggctcgag acccttactg tgcctgggat | 1620 |
| ggcatatcct gctcccggta ttacccaaca ggcacacatg caaaaaggaa gttcaagaaa | 1680 |
| caagatgttc gacatggaaa tgcagctcag cagtgctttg gacaacagtt tgttggggat | 1740 |

```
gctttggata agactgaaga acatctggct tatggcatag agaacaacag tactttgctg     1800
gaatgtaccc cacgatcttt acaagcgaaa gttatctggt ttgtacagaa aggacgtgag     1860
acaagaaaag aggaggtgaa gacagatgac agagtggtta agatggacct tggtttactc     1920
ttcctaaggt tacacaaatc agatgctggg acctattttt gccagacagt agagcatagc     1980
tttgtccata cggtccgtaa aatcaccttg gaggtagtgg aagaggagaa agtcgaggat     2040
atgtttaaca aggacgatga ggaggacagg catcacagga tgccttgtcc tgctcagagt     2100
agcatctcgc agggagcaaa accatggtac aaggaattct gcagctgatc ggttatagc      2160 aacttccaga gagtggaaga atactgcgag aaagtatggt gcacagatag aaagaggaaa     2220
aagcttaaaa tgtcaccctc caagtggaag tatgccaacc ctcaggaaaa gaagctccgt     2280
tccaaacctg agcattaccg cctgcccagg cacacgctgg actcctga                 2328

<210> SEQ ID NO 35
<211> LENGTH: 2349
<212> TYPE: DNA
<213> ORGANISM: Homo sapiens

<400> SEQUENCE: 35 atggcccccct cggcctgggc catttgctgg ctgctagggg gcctcctgct ccatggggt      60 agctctggcc ccagccccgg ccccagtgtg ccccgcctgc ggctctccta ccgagacctc     120
ctgtctgcca accgctctgc catctttctg gcccccagg gctccctgaa cctccaggcc      180
atgtacctag atgagtaccg agaccgcctc tttctgggtg gcctggacgc cctctactct     240
ctgcggctgg accaggcatg gccagatccc cgggaggtcc tgtggccacc gcagccagga     300
cagagggagg agtgtgttcg aaagggaaga gatcctttga cagagtgcgc caacttcgtg     360
cgggtgctac agcctcacaa ccggacccac ctgctagcct gtggcactgg ggccttccag     420
cccacctgtg ccctcatcac agttggccac cgtggggagc atgtgctcca cctggagcct     480
ggcagtgtgg aaagtggccg ggggcggtgc cctcacgagc ccagccgtcc ctttgccagc     540
accttcatag acggggagct gtacacgggt ctcactgctg acttcctggg gcgagaggcc     600
atgatcttcc gaagtggagg tcctcggcca gctctgcgtt ccgactctga ccagagtctc     660
ttgcacgacc cccggtttgt gatggccgcc cggatccctg agaactctga ccaggacaat     720
gacaaggtgt acttcttctt ctcggagacg gtccccctcg ccgatggtgg ctcgaaccat     780
gtcactgtca gccgcgtggg ccgcgtctgc gtgaatgatg ctgggggcca gcgggtgctg     840
gtgaacaaat ggagcacttt cctcaaggcc aggctggtct gctcggtgcc cggccctggt     900
ggtgccgaga cccactttga ccagctagag gatgtgttcc tgctgtggcc caaggccggg     960
aagagcctcg aggtgtacgc gctgttcagc accgtcagtg ccgtgttcca gggcttcgcc    1020
gtctgtgtgt accacatggc agacatctgg gaggttttca cgggcccctt gcccaccga    1080 gatgggcctc agcaccagtg ggggcccctat ggggcaagg tgcccttccc tcgccctggc    1140
gtgtgcccca gcaagatgac cgcacagcca ggacggcctt ttggcagcac caaggactac    1200
ccagatgagg tgctgcagtt tgcccgagcc cacccctca tgttctggcc tgtgcggcct    1260
cgacatggcc gccctgtcct tgtcaagacc cacctggccc agcagctaca ccagatcgtg    1320
gtggaccgcg tggaggcaga ggatgggacc tacgatgtca ttttcctggg gactgactca    1380
gggtctgtgc tcaaagtcat cgctctccag gcaggggct cagctgaacc tgaggaagtg    1440
gttctggagg agctccaggt gtttaaggtg ccaacaccta tcaccgaaat ggagatctct    1500
gtcaaaaggc aaatgctata cgtgggctct cggctgggtg tggcccagct gcggctgcac    1560
```

```
caatgtgaga cttacggcac tgcctgtgca gagtgctgcc tggcccggga cccatactgt    1620
gcctgggatg gtgcctcctg tacccactac cgccccagcc ttggcaagcg caaattcaaa    1680
aagcaggaca tccggcacgg caaccctgcc ctgcagtgcc tgggccagag ccaggaagaa    1740
gaggcagtgg gacttgtggc agccaccatg gtctacggca cggagcacaa tagcaccttc    1800
ctggagtgcc tgcccaagtc tccccaggct gctgtgcgct ggctcttgca gaggccaggg    1860
gatgagggc ctgaccaggt gaagacggac gagcgagtct tgcacacgga gcggggctg      1920
ctgttccgca ggcttagccg tttcgatgcg gcacctaca cctgcaccac tctggagcat     1980
ggcttctccc agactgtggt ccgcctggct ctggtggtga ttgtggcctc acagctggac    2040
aacctgttcc ctccggagcc aaagccagag gagcccccag cccggggagg cctggcttcc    2100
accccaccca aggcctggta caaggacatc ctgcagctca ttggcttcgc caacctgccc    2160
cgggtggatg agtactgtga gcgcgtgtgg tgcagggca ccacggaatg ctcaggctgc      2220
ttccggagcc ggagccgggg caagcaggcc aggggcaaga ctgggcagg ctggagcta      2280
ggcaagaaga tgaagagccg ggtgcatgcc gagcacaatc ggacgccccg ggaggtggag    2340
gccacgtag                                                            2349
```

<210> SEQ ID NO 36
<211> LENGTH: 777
<212> TYPE: PRT
<213> ORGANISM: Homo sapiens

<400> SEQUENCE: 36

Met Asn Ala Asn Lys Asp Glu Arg Leu Lys Ala Arg Ser Gln Asp Phe
1               5                   10                  15

His Leu Phe Pro Ala Leu Met Met Leu Ser Met Thr Met Leu Phe Leu
            20                  25                  30

Pro Val Thr Gly Thr Leu Lys Gln Asn Ile Pro Arg Leu Lys Leu Thr
        35                  40                  45

Tyr Lys Asp Leu Leu Leu Ser Asn Ser Cys Ile Pro Phe Leu Gly Ser
    50                  55                  60

Ser Glu Gly Leu Asp Phe Gln Thr Leu Leu Asp Glu Glu Arg Gly
65                  70                  75                  80

Arg Leu Leu Leu Gly Ala Lys Asp His Ile Phe Leu Leu Ser Leu Val
                85                  90                  95

Asp Leu Asn Lys Asn Phe Lys Lys Ile Tyr Trp Pro Ala Ala Lys Glu
            100                 105                 110

Arg Val Glu Leu Cys Lys Leu Ala Gly Lys Asp Ala Asn Thr Glu Cys
        115                 120                 125

Ala Asn Phe Ile Arg Val Leu Gln Pro Tyr Asn Lys Thr His Ile Tyr
    130                 135                 140

Val Cys Gly Thr Gly Ala Phe His Pro Ile Cys Gly Tyr Ile Asp Leu
145                 150                 155                 160

Gly Val Tyr Lys Glu Asp Ile Ile Phe Lys Leu Asp Thr His Asn Leu
                165                 170                 175

Glu Ser Gly Arg Leu Lys Cys Pro Phe Asp Pro Gln Gln Pro Phe Ala
            180                 185                 190

Ser Val Met Thr Asp Glu Tyr Leu Tyr Ser Gly Thr Ala Ser Asp Phe
        195                 200                 205

Leu Gly Lys Asp Thr Ala Phe Thr Arg Ser Leu Gly Pro Thr His Asp
    210                 215                 220

His His Tyr Ile Arg Thr Asp Ile Ser Glu His Tyr Trp Leu Asn Gly
225                 230                 235                 240

```
Ala Lys Phe Ile Gly Thr Phe Ile Pro Asp Thr Tyr Asn Pro Asp
            245                 250                 255

Asp Asp Lys Ile Tyr Phe Phe Arg Glu Ser Ser Gln Glu Gly Ser
            260                 265                 270

Thr Ser Asp Lys Thr Ile Leu Ser Arg Val Gly Arg Val Cys Lys Asn
            275                 280                 285

Asp Val Gly Gly Gln Arg Ser Leu Ile Asn Lys Trp Thr Thr Phe Leu
            290                 295                 300

Lys Ala Arg Leu Ile Cys Ser Ile Pro Gly Ser Asp Gly Ala Asp Thr
305                 310                 315                 320

Tyr Phe Asp Glu Leu Gln Asp Ile Tyr Leu Leu Pro Thr Arg Asp Glu
                325                 330                 335

Arg Asn Pro Val Val Tyr Gly Val Phe Thr Thr Thr Ser Ser Ile Phe
                340                 345                 350

Lys Gly Ser Ala Val Cys Val Tyr Ser Met Ala Asp Ile Arg Ala Val
                355                 360                 365

Phe Asn Gly Pro Tyr Ala His Lys Glu Ser Ala Asp His Arg Trp Val
370                 375                 380

Gln Tyr Asp Gly Arg Ile Pro Tyr Pro Arg Pro Gly Thr Cys Pro Ser
385                 390                 395                 400

Lys Thr Tyr Asp Pro Leu Ile Lys Ser Thr Arg Asp Phe Pro Asp Asp
                405                 410                 415

Val Ile Ser Phe Ile Lys Arg His Ser Val Met Tyr Lys Ser Val Tyr
                420                 425                 430

Pro Val Ala Gly Gly Pro Thr Phe Lys Arg Ile Asn Val Asp Tyr Arg
                435                 440                 445

Leu Thr Gln Ile Val Val Asp His Val Ile Ala Glu Asp Gly Gln Tyr
                450                 455                 460

Asp Val Met Phe Leu Gly Thr Asp Ile Gly Thr Val Leu Lys Val Val
465                 470                 475                 480

Ser Ile Ser Lys Glu Lys Trp Asn Met Glu Glu Val Val Leu Glu Glu
                485                 490                 495

Leu Gln Ile Phe Lys His Ser Ser Ile Ile Leu Asn Met Glu Leu Ser
                500                 505                 510

Leu Lys Gln Gln Gln Leu Tyr Ile Gly Ser Arg Asp Gly Leu Val Gln
                515                 520                 525

Leu Ser Leu His Arg Cys Asp Thr Tyr Gly Lys Ala Cys Ala Asp Cys
530                 535                 540

Cys Leu Ala Arg Asp Pro Tyr Cys Ala Trp Asp Gly Asn Ala Cys Ser
545                 550                 555                 560

Arg Tyr Ala Pro Thr Ser Lys Arg Lys Ala Lys Lys Gln Asp Val Lys
                565                 570                 575

Tyr Gly Asp Pro Ile Thr Gln Cys Trp Asp Ile Glu Asp Ser Ile Ser
                580                 585                 590

His Glu Thr Ala Asp Glu Lys Val Ile Phe Gly Ile Glu Phe Asn Ser
                595                 600                 605

Thr Phe Leu Glu Cys Ile Pro Lys Ser Gln Gln Ala Thr Ile Lys Trp
                610                 615                 620

Tyr Ile Gln Arg Ser Gly Asp Glu His Arg Glu Glu Leu Lys Pro Asp
625                 630                 635                 640

Glu Arg Ile Ile Lys Thr Glu Tyr Gly Leu Leu Ile Arg Ser Leu Gln
                645                 650                 655

Lys Lys Asp Ser Gly Met Tyr Tyr Cys Lys Ala Gln Glu His Thr Phe
```

-continued

```
                660             665             670
Ile His Thr Ile Val Lys Leu Thr Leu Asn Val Ile Glu Asn Glu Gln
            675             680             685

Met Glu Asn Thr Gln Arg Ala Glu His Glu Glu Gly Lys Val Lys Asp
            690             695             700

Leu Leu Ala Glu Ser Arg Leu Arg Tyr Lys Asp Tyr Ile Gln Ile Leu
705             710             715             720

Ser Ser Pro Asn Phe Ser Leu Asp Gln Tyr Cys Glu Gln Met Trp His
            725             730             735

Arg Glu Lys Arg Arg Gln Arg Asn Lys Gly Gly Pro Lys Trp Lys His
            740             745             750

Met Gln Glu Met Lys Lys Lys Arg Asn Arg Arg His His Arg Asp Leu
            755             760             765

Asp Glu Leu Pro Arg Ala Val Ala Thr
            770             775

<210> SEQ ID NO 37
<211> LENGTH: 775
<212> TYPE: PRT
<213> ORGANISM: Homo sapiens

<400> SEQUENCE: 37

Met Ala Ser Ala Gly His Ile Ile Thr Leu Leu Leu Trp Gly Tyr Leu
1               5               10              15

Leu Glu Leu Trp Thr Gly Gly His Thr Ala Asp Thr Thr His Pro Arg
            20              25              30

Leu Arg Leu Ser His Lys Glu Leu Asn Leu Asn Arg Thr Ser Ile
            35              40              45

Phe His Ser Pro Phe Gly Phe Leu Asp Leu His Thr Met Leu Leu Asp
    50              55              60

Glu Tyr Gln Glu Arg Leu Phe Val Gly Gly Arg Asp Leu Val Tyr Ser
65              70              75              80

Leu Ser Leu Glu Arg Ile Ser Asp Gly Tyr Lys Glu Ile His Trp Pro
            85              90              95

Ser Thr Ala Leu Lys Met Glu Glu Cys Ile Met Lys Gly Lys Asp Ala
            100             105             110

Gly Glu Cys Ala Asn Tyr Val Arg Val Leu His His Tyr Asn Arg Thr
            115             120             125

His Leu Leu Thr Cys Gly Thr Gly Ala Phe Asp Pro Val Cys Ala Phe
    130             135             140

Ile Arg Val Gly Tyr His Leu Glu Asp Pro Leu Phe His Leu Glu Ser
145             150             155             160

Pro Arg Ser Glu Arg Gly Arg Gly Arg Cys Pro Phe Asp Pro Ser Ser
            165             170             175

Ser Phe Ile Ser Thr Leu Ile Gly Ser Glu Leu Phe Ala Gly Leu Tyr
            180             185             190

Ser Asp Tyr Trp Ser Arg Asp Ala Ala Ile Phe Arg Ser Met Gly Arg
            195             200             205

Leu Ala His Ile Arg Thr Glu His Asp Asp Glu Arg Leu Leu Lys Glu
    210             215             220

Pro Lys Phe Val Gly Ser Tyr Met Ile Pro Asp Asn Glu Asp Arg Asp
225             230             235             240

Asp Asn Lys Val Tyr Phe Phe Phe Thr Glu Lys Ala Leu Glu Ala Glu
            245             250             255

Asn Asn Ala His Ala Ile Tyr Thr Arg Val Gly Arg Leu Cys Val Asn
```

```
                    260             265                 270
Asp Val Gly Gly Gln Arg Ile Leu Val Asn Lys Trp Ser Thr Phe Leu
            275                 280             285

Lys Ala Arg Leu Val Cys Ser Val Pro Gly Met Asn Gly Ile Asp Thr
            290                 295             300

Tyr Phe Asp Glu Leu Glu Asp Val Phe Leu Leu Pro Thr Arg Asp His
305             310              315                         320

Lys Asn Pro Val Ile Phe Gly Leu Phe Asn Thr Thr Ser Asn Ile Phe
                    325                 330             335

Arg Gly His Ala Ile Cys Val Tyr His Met Ser Ser Ile Arg Ala Ala
                340                 345             350

Phe Asn Gly Pro Tyr Ala His Lys Glu Gly Pro Glu Tyr His Trp Ser
            355                 360             365

Val Tyr Glu Gly Lys Val Pro Tyr Pro Arg Pro Gly Ser Cys Ala Ser
            370                 375             380

Lys Val Asn Gly Gly Arg Tyr Gly Thr Thr Lys Asp Tyr Pro Asp Asp
385                 390                 395                 400

Ala Ile Arg Phe Ala Arg Ser His Pro Leu Met Tyr Gln Ala Ile Lys
                    405                 410             415

Pro Ala His Lys Lys Pro Ile Leu Val Lys Thr Asp Gly Lys Tyr Asn
                420                 425             430

Leu Lys Gln Ile Ala Val Asp Arg Val Glu Ala Glu Asp Gly Gln Tyr
            435                 440             445

Asp Val Leu Phe Ile Gly Thr Asp Asn Gly Ile Val Leu Lys Val Ile
            450                 455             460

Thr Ile Tyr Asn Gln Glu Met Glu Ser Met Glu Glu Val Ile Leu Glu
465                 470                 475                 480

Glu Leu Gln Ile Phe Lys Asp Pro Val Pro Ile Ile Ser Met Glu Ile
                    485                 490             495

Ser Ser Lys Arg Gln Gln Leu Tyr Ile Gly Ser Ala Ser Ala Val Ala
                500                 505             510

Gln Val Arg Phe His His Cys Asp Met Tyr Gly Ser Ala Cys Ala Asp
            515                 520             525

Cys Cys Leu Ala Arg Asp Pro Tyr Cys Ala Trp Asp Gly Ile Ser Cys
            530                 535             540

Ser Arg Tyr Tyr Pro Thr Gly Thr His Ala Lys Arg Lys Phe Lys Lys
545                 550                 555                 560

Gln Asp Val Arg His Gly Asn Ala Ala Gln Gln Cys Phe Gly Gln Gln
                    565                 570             575

Phe Val Gly Asp Ala Leu Asp Lys Thr Glu Glu His Leu Ala Tyr Gly
                580                 585             590

Ile Glu Asn Asn Ser Thr Leu Leu Glu Cys Thr Pro Arg Ser Leu Gln
            595                 600             605

Ala Lys Val Ile Trp Phe Val Gln Lys Gly Arg Glu Thr Arg Lys Glu
            610                 615             620

Glu Val Lys Thr Asp Asp Arg Val Val Lys Met Asp Leu Gly Leu Leu
625                 630                 635                 640

Phe Leu Arg Leu His Lys Ser Asp Ala Gly Thr Tyr Phe Cys Gln Thr
                    645                 650             655

Val Glu His Ser Phe Val His Thr Val Arg Lys Ile Thr Leu Glu Val
                660                 665             670

Val Glu Glu Glu Lys Val Glu Asp Met Phe Asn Lys Asp Asp Glu Glu
            675                 680             685
```

```
Asp Arg His His Arg Met Pro Cys Pro Ala Gln Ser Ser Ile Ser Gln
            690                 695                 700

Gly Ala Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Arg Lys Arg Lys Lys Leu Lys Met Ser Pro Ser Lys Trp Lys Tyr Ala
            740                 745                 750

Asn Pro Gln Glu Lys Lys Leu Arg Ser Lys Pro Glu His Tyr Arg Leu
                755                 760                 765

Pro Arg His Thr Leu Asp Ser
            770             775

<210> SEQ ID NO 38
<211> LENGTH: 782
<212> TYPE: PRT
<213> ORGANISM: Homo sapiens

<400> SEQUENCE: 38

Met Ala Pro Ser Ala Trp Ala Ile Cys Trp Leu Leu Gly Gly Leu Leu
1               5                   10                  15

Leu His Gly Gly Ser Ser Gly Pro Ser Pro Gly Pro Ser Val Pro Arg
                20                  25                  30

Leu Arg Leu Ser Tyr Arg Asp Leu Leu Ser Ala Asn Arg Ser Ala Ile
            35                  40                  45

Phe Leu Gly Pro Gln Gly Ser Leu Asn Leu Gln Ala Met Tyr Leu Asp
        50                  55                  60

Glu Tyr Arg Asp Arg Leu Phe Leu Gly Gly Leu Asp Ala Leu Tyr Ser
65                  70                  75                  80

Leu Arg Leu Asp Gln Ala Trp Pro Asp Pro Arg Glu Val Leu Trp Pro
                85                  90                  95

Pro Gln Pro Gly Gln Arg Glu Glu Cys Val Arg Lys Gly Arg Asp Pro
            100                 105                 110

Leu Thr Glu Cys Ala Asn Phe Val Arg Val Leu Gln Pro His Asn Arg
        115                 120                 125

Thr His Leu Leu Ala Cys Gly Thr Gly Ala Phe Gln Pro Thr Cys Ala
    130                 135                 140

Leu Ile Thr Val Gly His Arg Gly Glu His Val Leu His Leu Glu Pro
145                 150                 155                 160

Gly Ser Val Glu Ser Gly Arg Gly Arg Cys Pro His Glu Pro Ser Arg
                165                 170                 175

Pro Phe Ala Ser Thr Phe Ile Asp Gly Glu Leu Tyr Thr Gly Leu Thr
            180                 185                 190

Ala Asp Phe Leu Gly Arg Glu Ala Met Ile Phe Arg Ser Gly Gly Pro
        195                 200                 205

Arg Pro Ala Leu Arg Ser Asp Ser Asp Gln Ser Leu Leu His Asp Pro
    210                 215                 220

Arg Phe Val Met Ala Ala Arg Ile Pro Glu Asn Ser Asp Gln Asp Asn
225                 230                 235                 240

Asp Lys Val Tyr Phe Phe Phe Ser Glu Thr Val Pro Ser Pro Asp Gly
                245                 250                 255

Gly Ser Asn His Val Thr Val Ser Arg Val Gly Arg Val Cys Val Asn
            260                 265                 270

Asp Ala Gly Gly Gln Arg Val Leu Val Asn Lys Trp Ser Thr Phe Leu
        275                 280                 285
```

-continued

```
Lys Ala Arg Leu Val Cys Ser Val Pro Gly Pro Gly Ala Glu Thr
290                 295                 300

His Phe Asp Gln Leu Glu Asp Val Phe Leu Leu Trp Pro Lys Ala Gly
305                 310                 315                 320

Lys Ser Leu Glu Val Tyr Ala Leu Phe Ser Thr Val Ser Ala Val Phe
                325                 330                 335

Gln Gly Phe Ala Val Cys Val Tyr His Met Ala Asp Ile Trp Glu Val
                340                 345                 350

Phe Asn Gly Pro Phe Ala His Arg Asp Gly Pro Gln His Gln Trp Gly
                355                 360                 365

Pro Tyr Gly Gly Lys Val Pro Phe Pro Arg Pro Gly Val Cys Pro Ser
370                 375                 380

Lys Met Thr Ala Gln Pro Gly Arg Pro Phe Gly Ser Thr Lys Asp Tyr
385                 390                 395                 400

Pro Asp Glu Val Leu Gln Phe Ala Arg Ala His Pro Leu Met Phe Trp
                405                 410                 415

Pro Val Arg Pro Arg His Gly Arg Pro Val Leu Val Lys Thr His Leu
                420                 425                 430

Ala Gln Gln Leu His Gln Ile Val Val Asp Arg Val Glu Ala Glu Asp
                435                 440                 445

Gly Thr Tyr Asp Val Ile Phe Leu Gly Thr Asp Ser Gly Ser Val Leu
                450                 455                 460

Lys Val Ile Ala Leu Gln Ala Gly Gly Ser Ala Glu Pro Glu Glu Val
465                 470                 475                 480

Val Leu Glu Glu Leu Gln Val Phe Lys Val Pro Thr Pro Ile Thr Glu
                485                 490                 495

Met Glu Ile Ser Val Lys Arg Gln Met Leu Tyr Val Gly Ser Arg Leu
                500                 505                 510

Gly Val Ala Gln Leu Arg Leu His Gln Cys Glu Thr Tyr Gly Thr Ala
                515                 520                 525

Cys Ala Glu Cys Cys Leu Ala Arg Asp Pro Tyr Cys Ala Trp Asp Gly
                530                 535                 540

Ala Ser Cys Thr His Tyr Arg Pro Ser Leu Gly Lys Arg Lys Phe Lys
545                 550                 555                 560

Lys Gln Asp Ile Arg His Gly Asn Pro Ala Leu Gln Cys Leu Gly Gln
                565                 570                 575

Ser Gln Glu Glu Glu Ala Val Gly Leu Val Ala Ala Thr Met Val Tyr
                580                 585                 590

Gly Thr Glu His Asn Ser Thr Phe Leu Glu Cys Leu Pro Lys Ser Pro
                595                 600                 605

Gln Ala Ala Val Arg Trp Leu Leu Gln Arg Pro Gly Asp Glu Gly Pro
610                 615                 620

Asp Gln Val Lys Thr Asp Glu Arg Val Leu His Thr Glu Arg Gly Leu
625                 630                 635                 640

Leu Phe Arg Arg Leu Ser Arg Phe Asp Ala Gly Thr Tyr Thr Cys Thr
                645                 650                 655

Thr Leu Glu His Gly Phe Ser Gln Thr Val Val Arg Leu Ala Leu Val
                660                 665                 670

Val Ile Val Ala Ser Gln Leu Asp Asn Leu Phe Pro Pro Glu Pro Lys
                675                 680                 685

Pro Glu Glu Pro Pro Ala Arg Gly Gly Leu Ala Ser Thr Pro Pro Lys
                690                 695                 700

Ala Trp Tyr Lys Asp Ile Leu Gln Leu Ile Gly Phe Ala Asn Leu Pro
705                 710                 715                 720
```

```
Arg Val Asp Glu Tyr Cys Glu Arg Val Trp Cys Arg Gly Thr Thr Glu
                725                 730                 735

Cys Ser Gly Cys Phe Arg Ser Arg Ser Arg Gly Lys Gln Ala Arg Gly
            740                 745                 750

Lys Ser Trp Ala Gly Leu Glu Leu Gly Lys Lys Met Lys Ser Arg Val
        755                 760                 765

His Ala Glu His Asn Arg Thr Pro Arg Glu Val Glu Ala Thr
    770                 775                 780

<210> SEQ ID NO 39
<211> LENGTH: 4
<212> TYPE: PRT
<213> ORGANISM: Artificial sequence
<220> FEATURE:
<223> OTHER INFORMATION: Pro-protein convertase recognition sequence

<400> SEQUENCE: 39

Arg Phe Arg Arg
1

<210> SEQ ID NO 40
<211> LENGTH: 4
<212> TYPE: PRT
<213> ORGANISM: Artificial sequence
<220> FEATURE:
<223> OTHER INFORMATION: Mutated pro-protein convertase recognition
      sequence

<400> SEQUENCE: 40

Lys Phe Lys Lys
1
```

COMPOSITIONS COMPRISING SEMAPHORINS FOR THE TREATMENT OF ANGIOGENESIS RELATED DISEASES AND METHODS OF SELECTION THEREOF

RELATED APPLICATIONS

This application is a divisional of U.S. patent application Ser. No. 12/738,634 filed on Apr. 18, 2010, which is a National Phase of PCT Patent Application No. PCT/IL2008/001307 having International filing date of Oct. 2, 2008, which claims the benefit of priority under 35 USC 119(e) of U.S. Provisional Patent Application Nos. 61/071,560 filed on May 6, 2008, 61/071,053 filed on Apr. 10, 2008, 61/006,496 filed on Jan. 16, 2008, and 60/960,910 filed on Oct. 19, 2007.

The contents of all of the above applications are incorporated by reference as if fully set forth herein.

FIELD AND BACKGROUND OF THE INVENTION

The present invention, in some embodiments thereof, relates to methods and compositions for treating angiogenesis-related diseases such as cancer, and methods of selection thereof.

The neuropilin-1 (np1) and the neuropilin-2 (np2) receptors were originally characterized as functional receptors for axon guidance factors belonging to the class-3 semaphorin (sema3) family. It was subsequently realized that the neuropilins are expressed by endothelial cells and by many types of cancer cells. It was also found that the neuropilins function in addition as receptors for several angiogenic factors belonging to the VEGF family and as receptors for the angiogenesis/metastasis inducing growth factor hepatocyte growth factor/scatter factor (HGF/SF), and that they function as potent enhancers of their pro-angiogenic activity.

Most of the sema3s, with the exception of sema3E which binds to PlexD1, bind to one of the two neuropilin receptors or to both. Neuropilins form spontaneous complexes with several members of the plexin receptor family. In these complexes the sema3s bind to neuropilins while the plexins function as the signal transducing elements. The four type-A plexins (plexins-A1 to plexin-A4) as well as plexin-D1 form complexes with neuropilins and participate in neuropilin mediated signal transduction.

Semaphorins sema3B and sema3F were also characterized as tumor suppressors whose loss contributes to the development of lung cancer [Tomizawa, Y., 2001, Proc. Natl. Acad. Sci. U.S.A 98:13954-13959; Xiang, R., 2002. Cancer Res. 62:2637-2643].

The identification of neuropilins in endothelial cells suggested that class-3 semaphorins may be able to regulate angiogenesis. Indeed, the class-3 semaphorin sema3F, a np2 agonist, functions as a repellant of endothelial cells, induces apoptosis of endothelial cells upon prolonged stimulation [Bielenberg, D. R., et al., 2004, J. Clin. Invest 114:1260-1271; Guttmann-Raviv, N., et al., 2007, J. Biol. Chem. 282: 26294-26305] and inhibits angiogenesis and tumor progression in-vivo [Bielenberg, D. R., et al., 2004, J. Clin. Invest 114:1260-1271; Kessler, O., et al 2004. Cancer Res. 64:1008-1015. The np1 agonist sema3A was also shown to inhibit in-vitro and in-vivo angiogenesis [Miao, H. Q., 1999. J. Cell Biol. 146:233-242. Bates, D., 2003, Dev. Biol. 255:77-98; Acevedo, L. M., 2008. Blood. 111:2674-2680]. Sema3E was also characterized as a repulsive agent that inhibits the invasion of PlexD1 expressing blood vessels into somites during embryonic development [Gu C. et al., 2005, Science 307:265-268].

In contrast, existing data suggests that sema3C functions as a pro-tumorigenic and pro-angiogenic agent [Herman J G, et al, Int. J. Oncol. 2007; 30:1231-1238; Banu N, FASEB J. 2006; 20:2150-2152].

The fact that neuropilins and plexins such as PlexD1 are also expressed by many types of tumor cells indicates that semaphorins may also affect the behavior of tumor cells directly. Indeed, sema3s such as sema3F and sema3B have been observed to inhibit the adhesion, migration or the proliferation of tumor cells expressing appropriate semaphorin receptors [Tomizawa, Y., 2001, Proc. Natl. Acad. Sci. U.S.A 98:13954-13959; Xiang, R., 2002. Cancer Res. 62:2637-2643; Bielenberg, D. R., et al., 2004, J. Clin. Invest 114:1260-1271; Nasarre, 2006, Neoplasia. 7:180-189]. In contrast, however, the cleavage product of Sema3E, was shown to be an inducer of tumor invasiveness and tumor metastasis [Christensen, C, 2005, Cancer Res. 65, 6167-6177].

SUMMARY OF THE INVENTION

According to an aspect of some embodiments of the present invention there is provided a method of selecting a semaphorin for treating cancer in a subject, the method comprising determining an expression of a semaphorin receptor on tumor cells of a tumor sample of the subject wherein an amount of the semaphorin receptor is indicative of the semaphorin suitable for treating the cancer in the subject.

According to an aspect of some embodiments of the present invention there is provided a method of treating cancer in a subject in need thereof, the method comprising:

(a) selecting a semaphorin for treating cancer in the subject according to the method of the present invention; and (b) contacting cancerous cells of the subject with a therapeutically effective amount of an agent capable of upregulating said semaphorin, thereby treating the cancer.

According to an aspect of some embodiments of the present invention there is provided a kit for treating cancer, the kit comprising at least one agent capable of identifying a semaphorin receptor sub-type and at least one semaphorin.

According to an aspect of some embodiments of the present invention there is provided a method of treating a disease associated with angiogenesis in a subject in need thereof, the method comprising administering to the subject a therapeutically effective amount of a semaphorin selected from the group consisting of Sema3D, Sema3E and Sema3G, thereby treating the disease associated with angiogenesis.

According to an aspect of some embodiments of the present invention there is provided a use of a semaphorin selected from the group consisting of Sema3D, Sema3E and Sema3G for the treatment of a disease associated with angiogenesis.

According to an aspect of some embodiments of the present invention there is provided a pharmaceutical composition comprising as an active ingredient a semaphorin selected from the group consisting of Sema3D, Sema3E and Sema3G and a pharmaceutically acceptable carrier.

According to some embodiments of the invention, when the semaphorin receptor comprises NP1, the semaphorin comprises Sema3A or Sema3D.

According to some embodiments of the invention, when the semaphorin receptor comprises NP2, the semaphorin comprises Sema3G or Sema3F.

According to some embodiments of the invention, when the semaphorin receptor comprises PlexD1, the semaphorin comprises Sema3E.

According to some embodiments of the invention, the agent is an antibody.

According to some embodiments of the invention, the determining is effected using an antibody.

According to some embodiments of the invention, the semaphorin is a class 3 semaphorin.

According to some embodiments of the invention, the class 3 semaphorin is selected from the group consisting of sema3A, sema3C, sema3D, sema3E and sema3G.

According to some embodiments of the invention, the contacting is effected in vivo.

According to some embodiments of the invention, the contacting is effected ex vivo.

According to some embodiments of the invention, the agent is a polynucleotide agent comprising a nucleic acid sequence encoding the semaphorin.

According to some embodiments of the invention, the semaphorin receptor is selected from the group consisting of Np1, Np2, PlexA1-4 and PlexD.

According to some embodiments of the invention, the semaphorin is sema3E.

According to some embodiments of the invention, the sema3E is a pro-protein convertase resistant Sema3E.

According to some embodiments of the invention, the disease associated with angiogenesis is selected from the group consisting of cancer, arthritis, rheumatoid arthritis, atherosclerotic plaques, corneal graft neovascularization, hypertrophic or keloid scars, proliferative retinopathy, diabetic retinopathy, macular degeneration, granulation, neovascular glaucoma and uveitis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C:
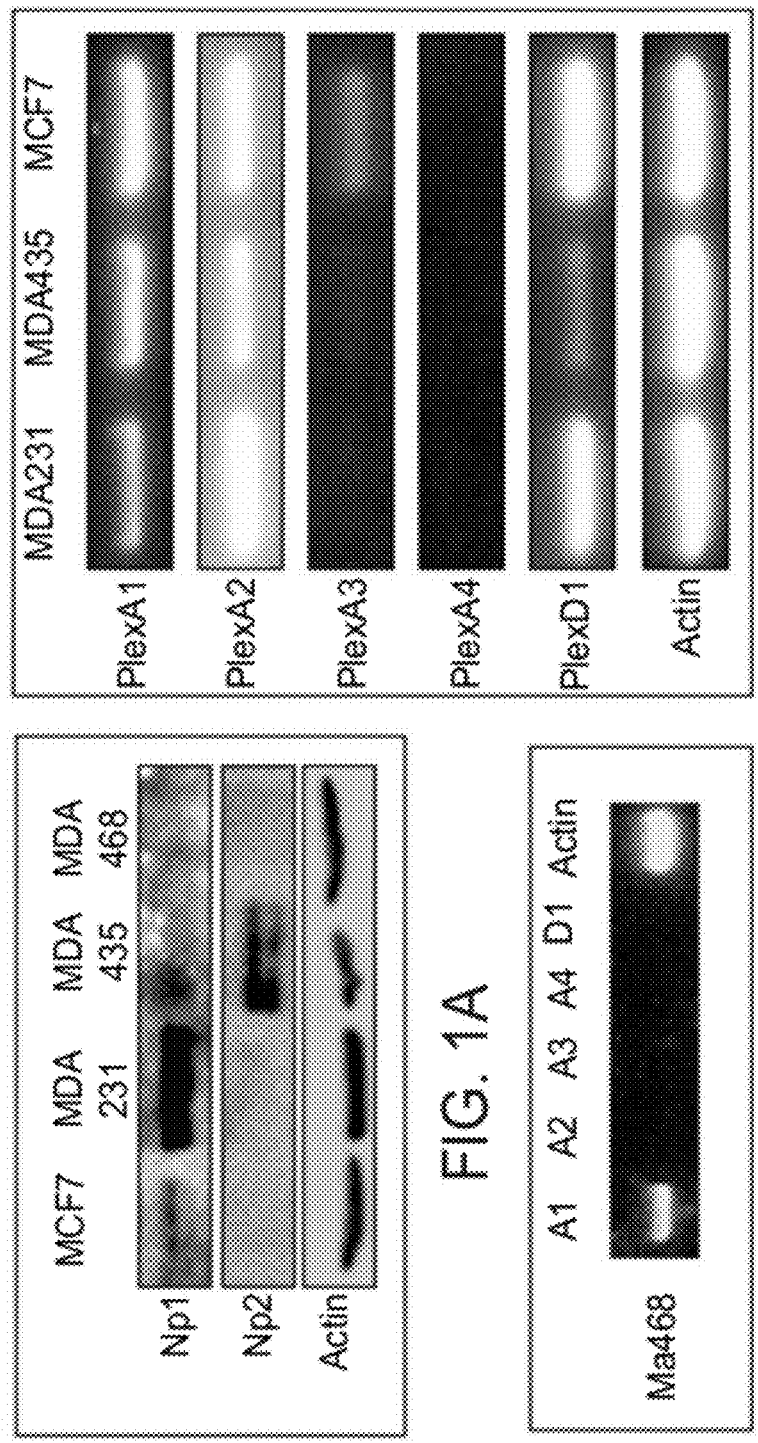

FIGS. 1A-C are photographs illustrating the expression of sema3 receptors in breast cancer derived cell lines. FIG. 1A. Cells were grown to 80% confluency and lysed. Equal amounts of protein were loaded and separated on SDS/PAGE gels and blotted on nitrocellulose. Western blot analysis of np1 and np2 was performed as described. FIGS. 1B-C. Reverse PCR analysis of plexA1-A4 and plexD1 expression was performed according to the instruction of the PerfectPure kit using primer pairs specific to the different plexins.

FIGS. 2A-L are graphs and photographs illustrating the effect of the expression of different sema3s on the development of tumors from MDA-MB-231 cells. MDA-MB-231 cells were implanted in the mammary fat pads of balb\c nu/nu mice as described. FIGS. 2A, D, G, J. Western blot analysis of aliquots of conditioned medium derived from cells expressing the different sema3s. At the end of the experiment tumors were excised and photographed. FIGS. 2B, E, H, K. The average volume of the developing tumors was measured as described. FIGS. 2C, F, I, L. The average weight of the tumors at the end of the experiment was determined as described.

Figure 3A:
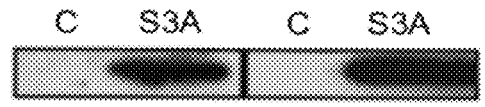
Figure 3B:
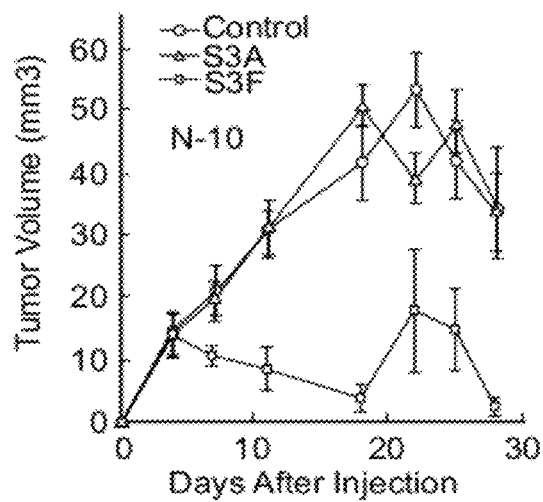
Figure 3C:
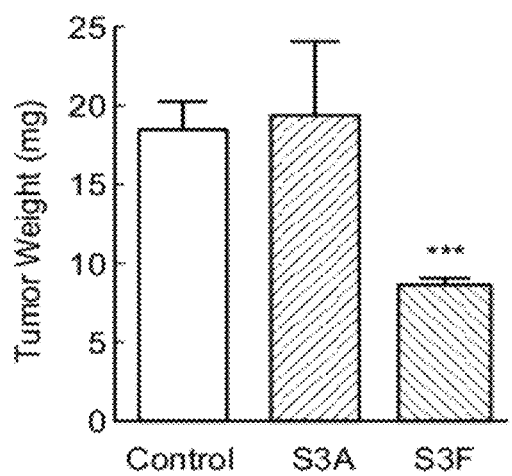
Figure 3D:
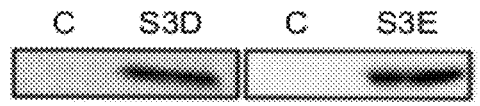

FIGS. 3A-I are graphs and photographs illustrating the effect of the expression of different sema3s on the development of tumors from MDA-MB-435 cells. MDA-MB-435 cells were implanted in the mammary fat pad of balb\c nu/nu mice as described. FIGS. 3A, D, G. Western blot analysis of aliquots of conditioned medium derived from cells expressing the different sema3s. FIGS. 3B, E, H. The average volume of the developing tumors was measured as described. FIGS. 3C, F, I. The average weight of the tumors at the end of the experiment was determined as described.

Figure 4A:
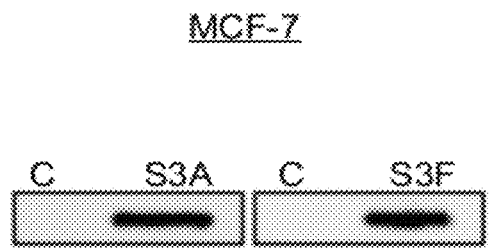
Figure 4B:
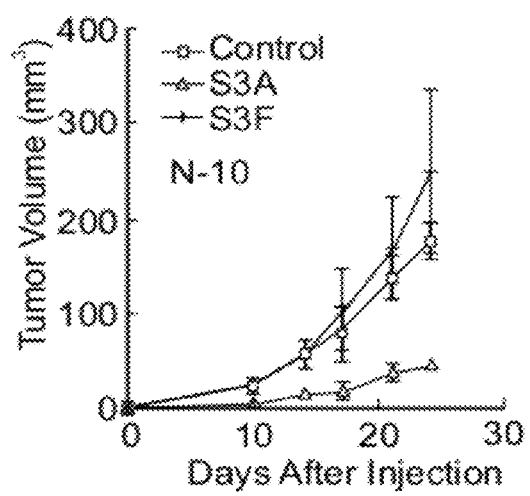
Figure 4C:
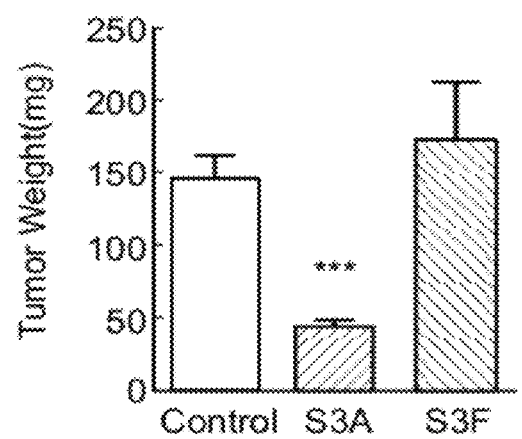
Figure 4D:

FIGS. 4A-F are graphs and photographs illustrating the effect of the expression of sema3A and sema3F on the development of tumors from MCF-7 and MDA-MB-468 cells. MCF-7 and MDA-MB-468 cells were implanted in the mammary fat pad of balb\c nu/nu mice as described. FIGS. 4A, D. Western blot analysis of aliquots of conditioned medium derived from cells expressing either sema3A or sema3F. FIGS. 4B, E. The average volume of the developing tumors was measured as described. FIGS. 4C, F. The average weight of the tumors at the end of the experiment was determined as described.

Figure 5A:
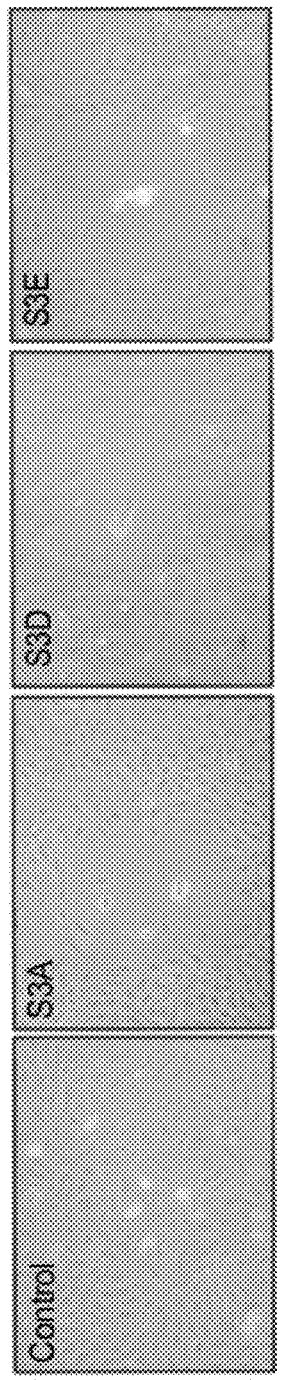
Figure 5B:
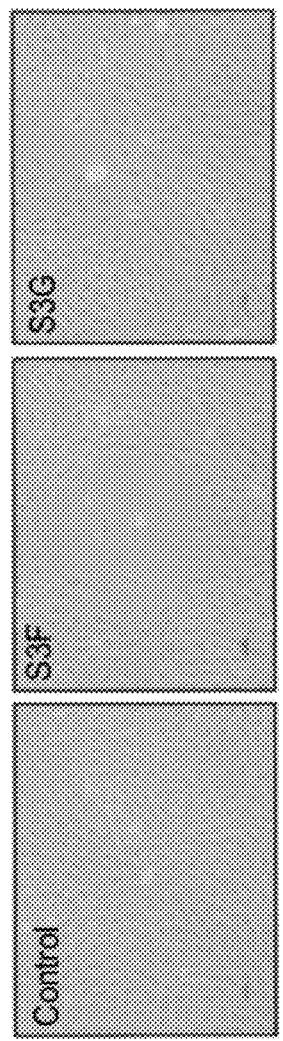
Figure 5E:
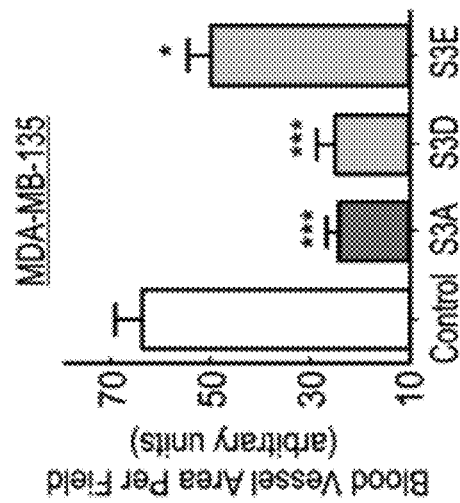
Figure 5D:
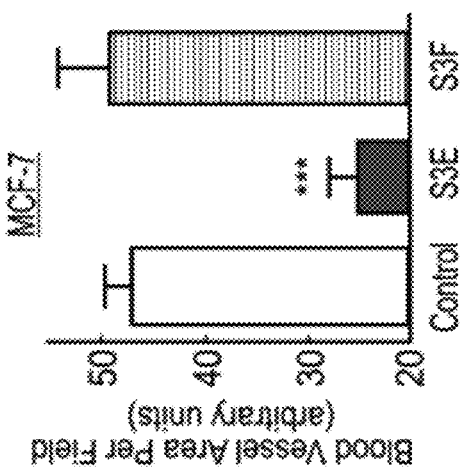
Figure 5C:
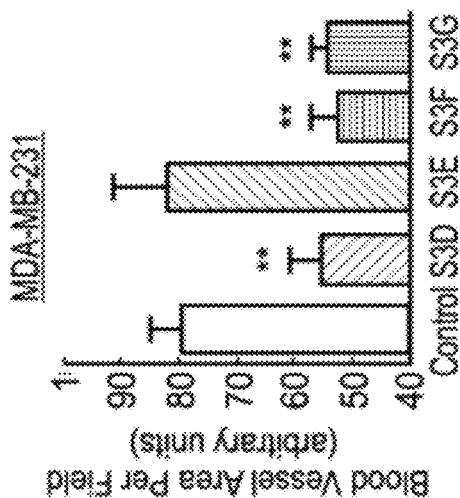

FIGS. 5A-E are graphs and photographs illustrating that different sema3s repel endothelial cells in-vitro and reduce the density of tumor associated blood vessels in-vivo. FIG. 5A: Control HEK293 cells infected with an empty lentiviral vector or HEK293 cells expressing sema3A, sema3D or sema3E were seeded on top of a monolayer of HUVEC cells as described in experimental procedures. The HEK292 cells were labeled with the fluorescent vital dye DIasp prior to seeding. Shown are composite pictures taken by phase and fluorescent microscopy. FIG. 5B. Control HEK293 cells infected with an empty lentiviral vector or HEK293 cells expressing sema3F, sema3G were seeded on a monolayer of PAE cells expressing np2 and plexA1 as described in the Materials and Methods. The HEK293 cells were stained with DIasp and photographed as described herein above. FIG. 5C. The average area of blood vessels per microscopic field was determined in sections derived from tumors that developed from control MDA-MB-231 cells or from MDA-MB-231 cells expressing different sema3s as described herein. Since the tumors that did develop from sema3A expressing cells were extremely small, the density of blood vessels in them could not be determined FIG. 5D. The average area of blood vessels per microscopic field was determined in tumors derived from control MCF-7 cells or from MCF-7 cells expressing sema3A or sema3F as described herein above. FIG. 5E. The average area of blood vessels per microscopic field was determined in tumors that developed from control MDA-MB-435 cells or from MDA-MB-435 cells expressing different sema3s as described herein above. No tumors developed from sema3G expressing cells.

FIGS. 6A-D are graphs and photographs illustrating that different sema3s inhibit the formation of soft agar colonies from MDA-MB-231 or MDA-MB-435 cells. FIG. 13A.

Figure 6A:
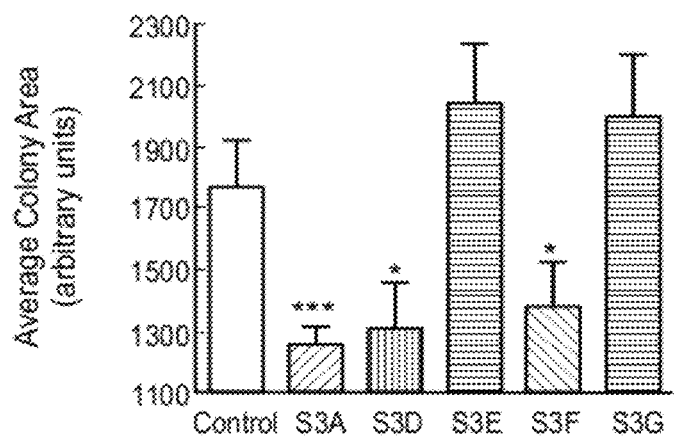
Figure 6B:
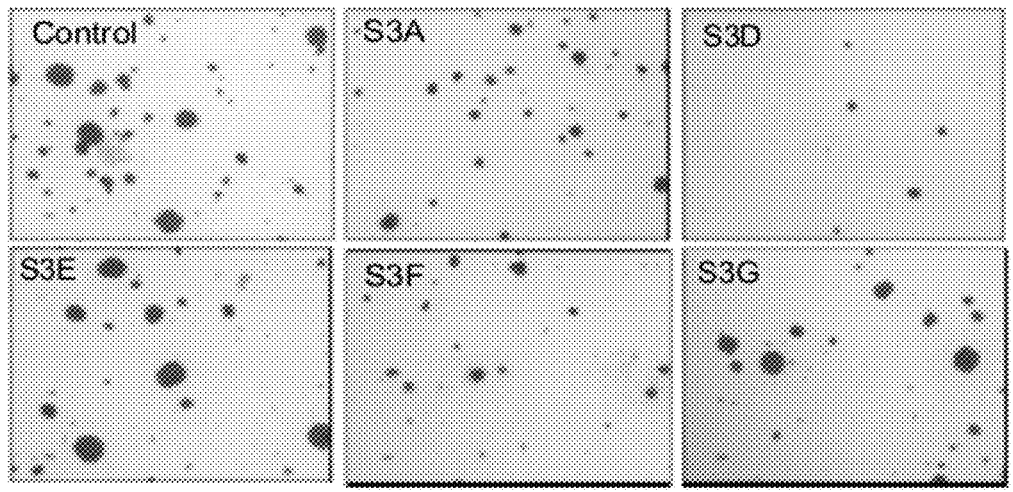
Figure 6C:
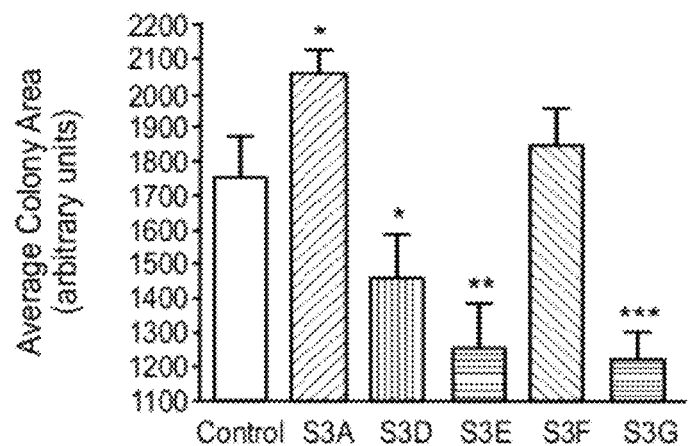
Figure 6D:
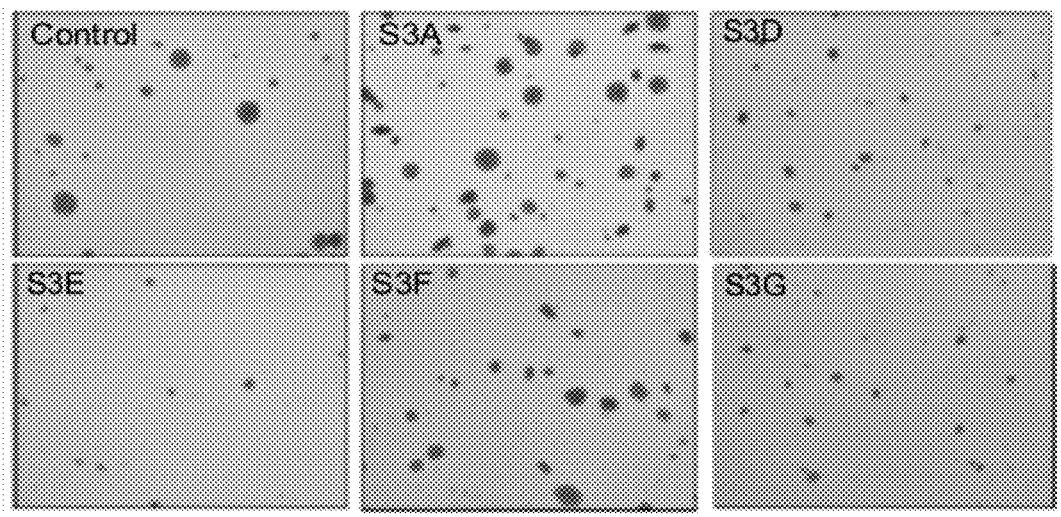

Single cell suspensions of control MDA-MB-231 cells or MDA-MB-231 cells expressing different sema3s were seeded in soft agar as described herein. Colonies were allowed to form for 21 days. The colonies were then stained with crystal violet and microscopic fields photographed. The average number/field of colonies with a diameter exceeding 150 μm was then determined as described under experimental procedures. FIG. 6B. Photographs of representative microscopic fields containing crystal violet stained colonies that developed in soft agar from control MDA-MB-231 cells or from sema3s expressing MDA-MB-231 cells. FIG. 6C. The formation of colonies in soft agar from control MDA-MB-435 cells or from MDA-MB-435 cells expressing different sema3s was determined as described herein above. FIG. 6D. Photographs of representative microscopic fields containing crystal violet stained colonies that developed in soft agar from control MDA-MB-435 cells or from sema3s expressing MDA-MB-435 cells.

Figure 7A:
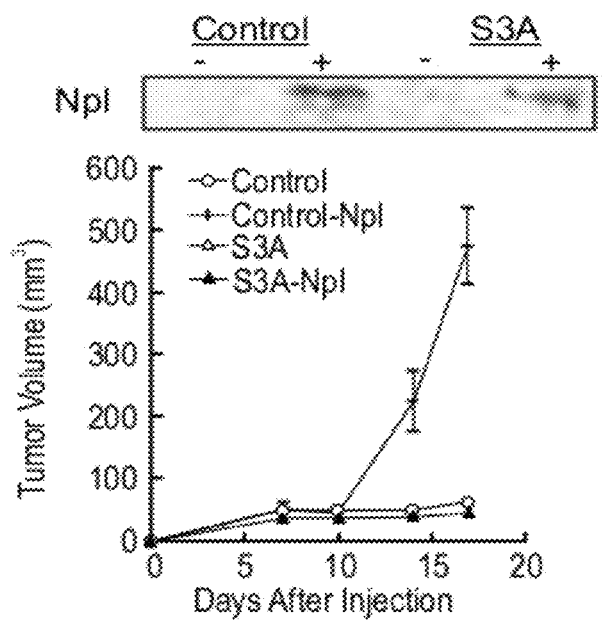
Figure 7B:
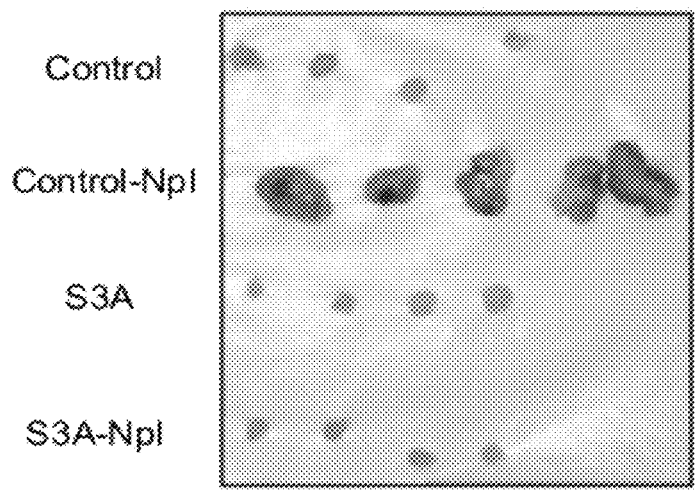
Figure 7C:
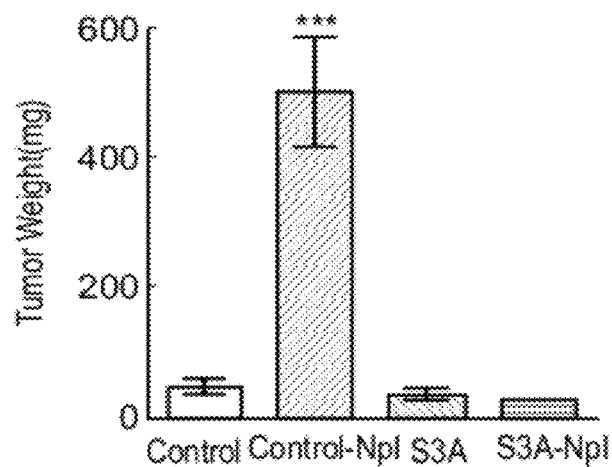

FIGS. 7A-D are graphs and photographs illustrating that expression of np1 in MDA-MB-435 cells enhances the growth of resulting tumors and sema3A abrogate the enhancing effect. FIG. 7A. A western blot comparing the expression of np1 in MDA-MB-435 cells infected with various combinations as depicted of a control lentiviral vector, a lentiviral vector containing the np1cDNA and a lentiviral vector containing the sema3A cDNA is shown at the top. The Average tumor volume as was measured during the experiment as described and is shown in the graph below. FIG. 7B. Photographs of tumors excised at the end of the experiment. FIG. 7C. The average weight of the tumors at the end of the experiment was determined FIG. 7D. The average area of blood vessels/field in tumor sections was determined.

DESCRIPTION OF SPECIFIC EMBODIMENTS OF THE INVENTION

The present invention, in some embodiments thereof, relates to methods and compositions for treating angiogenesis-related diseases such as cancer, and methods of selection thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The semaphorins belonging to the class-3 semaphorin sub-family (sema-3s) function as axon guidance factors during embryonic development. Most of the class-3 semaphorins, with the exception of sema3E, bind to one of the two neuropilin receptors, which in turn form complexes with several members of the plexin receptor family. In these complexes the neuropilins bind the semaphorins while the plexins function as the signal transducing elements.

Semaphorins sema3B and sema3F have been characterized as tumor suppressors, whilst sema3F, sema3A and sema3E have each been attributed an anti angiogenic function.

Whilst reducing the present invention to practice, the present inventors have shown that sema3A, sema3D, sema3E and sema3G each function as potent anti-tumorigenic agents (FIGS. 2A-L; FIGS. 3A-I; FIGS. 4A-F). Specifically, injection of breast cancer cells expressing these semaphorins into nude mice resulted in tumors of reduced size as compared to tumors resulting from injection of tumor cells not expressing these semaphorins.

Whilst further reducing the present invention to practice, the present inventors have shown that semaphorin induced inhibition of tumor development from specific types of breast cancer cells is correlated with the expression of appropriate semaphorin receptors by the tumor cells. Although, the majority of the tested semaphorins also inhibited tumor angiogenesis, the present inventors showed that there was no correlation between inhibition of tumor angiogenesis and inhibition of tumor development. These results suggest that inhibition of tumor development by semaphorins depends on the expression of appropriate semaphorin receptors by tumor cells, and suggest that inhibition of angiogenesis is of lesser importance. They also suggest that tumors containing tumor cells expressing semaphorin receptors may be amenable to inhibition by appropriate sema3s and open the way for improved methods of personalized medicine for cancer treatment.

Thus, according to one aspect of the present invention, there is provided a method of selecting a semaphorin for treating cancer in a subject. The method comprises determining an expression of a semaphorin receptor on tumor cells of a tumor sample of the subject wherein an amount of the semaphorin receptor is indicative of the semaphorin suitable for treating the cancer in the subject.

As used herein, the term "semaphorin" refers to a mammalian polypeptide (e.g. human) belonging to the semaphorin family (including semaphorins of class 3, 4, 5, 6 and 7). Semaphorins typically function as signals during axon guidance and comprise a sema domain.

According to one embodiment, the semaphorin belongs to the class-3 semaphorin sub-family. Accordingly, the semaphorin may be semaphorin 3A (Genbank accession number NM_006080, SEQ ID NO: 26); semaphorin 3B (Genbank accession number NM_001005914, SEQ ID NO: 27); semaphorin 3C (Genbank accession number NM_006379, SEQ ID NO: 28); semaphorin 3D (Genbank accession number NM_152754, SEQ ID NO: 29); semaphorin 3E (Genbank accession number NM_012431, SEQ ID NO: 30); semaphorin 3F (Genbank accession number NM_004186, SEQ ID NO: 31); or semaphorin 3G (Genbank accession number NM_020163, SEQ ID NO: 32).

A semaphorin of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to semaphorin sequences listed herein above as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

The term "treating" as used herein includes abrogating, substantially inhibiting, slowing or reversing the progression of the cancer, substantially ameliorating clinical or aesthetical symptoms of the cancer or substantially preventing the appearance of clinical or aesthetical symptoms of the cancer.

Typically, the subject for whom the semaphorin is selected is a mammalian subject e.g. a human.

As used herein the term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Typically, the cancer cells are in the form of a tumor; existing locally within an animal, or circulating in the blood stream as independent cells, for example, leukemic cells.

Specific examples of cancer for which semaphorins may be selected according to this aspect of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a particular embodiment of this aspect of the present invention, the cancer is breast cancer.

As mentioned, the method of the present invention is effected by determining an expression of a semaphorin receptor on tumor cells of a tumor sample of a subject.

As used herein, the phrase "semaphorin receptor" refers to a cell-surface polypeptide that is capable of binding to a semaphorin and transducing a response. Exemplary semaphorin receptors include, neuropilins, plexins and integrins.

Thus, for example, the neuropilin receptor may be a neuropilin 1 receptor (NP1; e.g. NM_001024628; SEQ ID NO: 17) or a neuropilin 2 receptor (NP2; e.g. NM_201279; SEQ ID NO: 18).

The plexin receptor may be a plexinA1 receptor (PlexA1; e.g. NM_032242; SEQ ID NO: 19), a plexinA2 receptor (PlexA2; e.g. NM_025179; SEQ ID NO: 20), a plexinA3 receptor (PlexA3; e.g. NM_017514; SEQ ID NO: 21), a plexinA4 receptor (PlexA4; e.g. NM_020911, SEQ ID NO: 22; NM_001105543, SEQ ID NO: 23; NM_181775, SEQ ID NO: 24) or a plexinD receptor (PlexD; e.g. NM_015103, SEQ ID NO: 25).

Methods of determining an expression of a semaphorin receptor are known in the art. Specifically, determining an expression of semaphorin receptors may be effected on the RNA or protein level as detailed below.

Methods of Detecting Expression of a Semaphorin Receptor on the RNA Level
Northern Blot Analysis:
This method involves the detection of a particular RNA i.e. a semaphoring receptor RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radioisotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:
This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls. Exemplary primers that may be used to detect NRP1 receptors are set forth in SEQ ID NOs: 3 and 4. Exemplary primers that may be used to detect NRP2 receptors are set forth in SEQ ID NOs: 5 and 6. Exemplary primers that may be used to detect PLXNA1 receptors are set forth in SEQ ID NOs: 7 and 8. Exemplary primers that may be used to detect PLXNA2 receptors are set forth in SEQ ID NOs: 9 and 10. Exemplary primers that may be used to detect PLXNA3 receptors are set forth in SEQ ID NOs: 11 and 12. Exemplary primers that may be used to detect PLXNA4 receptors are set forth in SEQ ID NOs: 13 and 14. Exemplary primers that may be used to detect PLXND1 receptors are set forth in SEQ ID NOs: 15 and 16. Exemplary primers that may be used to detect CDH2 receptors are set forth in SEQ ID NOs: 1 and 2.

RNA in Situ Hybridization Stain:
In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In Situ RT-PCR Stain:

This Method is Described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide Microarray—

In this method oligonucleotide probes capable of specifically hybridizing with the polynucleotides encoding the semaphorin receptors of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., tumor cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Methods of Detecting Semaphorin Receptors on the Protein Level

Determining expression of a semaphorin receptor on the protein level is typically effected using an antibody capable of specifically binding with a particular semaphorin receptor.

Exemplary antibodies capable of specifically interacting with NP1 and NP2 are widely available e.g. from Santa-Cruz Biotechnology (Santa Cruz, Calif., Catalogue nos. sc-12122, sc 12123, sc-12125, sc-12128 and sc-50408).

Exemplary antibodies capable of specifically interacting with plexin receptors are also widely available e.g. from Santa-Cruz Biotechnology (Santa Cruz, Calif., Catalogue Nos. sc-25639, sc-10138, sc-10139, sc-10144, sc-25640, sc-10143, sc-25641, sc-10135, sc-10134, sc-28372, sc10147, sc-25642, sc-10145, sc-67034, sc-34504, sc-34506, sc-34507, sc-46240, sc-67144, sc-46241, sc-46242, sc46243, sc-10152, sc-10149, sc-46244, sc-46245, sc-67145, sc-46246 and sc-46247. Antibodies are also available from Abcam Mass., U.S.A. (Catalogue Nos. ab32960, ab23391, ab39350, ab39357, ab39008, ab41564 and ab39715).

Preferably, the antibody specifically binds at least one epitope of the semaphorin receptor. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof which bind to specific semaphorin receptors are well known in the art (See for example, Harlow and Lane, Antibodies: A Laboratory Manual, Cold Spring Harbor Laboratory, New York, 1988, incorporated herein by reference).

Methods of detecting semaphorin receptors include immunoassays which include but are not limited to competitive and non-competitive assay systems using techniques such as Western blots, radioimmunoassays, ELISA (enzyme linked immunosorbent assay), "sandwich" immunoassays, and immunoprecipitation assays and immunohistochemical assays as detailed herein below.

Enzyme Linked Immunosorbent Assay (ELISA):

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

It will be appreciated that the tumor cells of the subject are obtained from a tumor sample e.g. during a tumor biopsy.

As mentioned, the amount of the semaphorin receptor is indicative of the semaphorin suitable for treating the cancer in the subject.

It will be appreciated that the amount of the semaphorin receptor should be sufficient to transduce a biological response (i.e. tumor inhibition). The amount of receptor sufficient to generate such a response is typically dependent on the affinity of the semaphorin for that receptor. Thus, for example if a semaphorin has a high affinity for a receptor (e.g. comprises a Km of about $10^{-7}$ M, $10^{-8}$ M, $10^{-9}$ M, $10^{-10}$ M or even $10^{-11}$ M), the amount of receptor does not have to be as great the amount of receptor for which the semaphorin has a low affinity receptor (e.g. comprises a Km of about $10^{-6}$ M $10^{-5}$ M, $10^{-4}$ M, $10^{-3}$ M).

According to one embodiment, the amount of receptor on the tumor cells is at least 20% the total number of semaphorin receptors on the tumor cells. According to another embodiment, the amount of receptor on the tumor cells is at least 30% the total number of semaphorin receptors on the tumor cells. According to another embodiment, the amount of receptor on the tumor cells is at least 40% the total number of semaphorin receptors on the tumor cells. According to another embodiment, the amount of receptor on the tumor cells is at least 50% the total number of semaphorin receptors on the tumor cells. According to another embodiment, the amount of receptor on the tumor cells is at least 60% the total number of semaphorin receptors on the tumor cells. According to another embodiment, the amount of receptor on the tumor cells is at least 70% the total number of semaphorin receptors on the tumor cells. According to another embodiment, the amount of receptor on the tumor cells is at least 80% the total number of semaphorin receptors on the tumor cells.

Accordingly, the present inventors have found that if a sufficient quantity of NP1 receptors are located on the tumor cells, the most preferable semaphorin for treatment comprises Sema3A or Sema3D. If a sufficient quantity of NP2 receptors are located on the tumor cells, the most preferable semaphorin for treatment comprises Sema3G or Sema3F. If a sufficient quantity of PlexD1 receptors are located on the tumor cells, the most preferable semaphorin for treatment comprises Sema3E.

It will be appreciated that selection of the semaphorin is not only based on the quantity of a receptor, but also expression profile of a plurality of semaphorin receptors subtypes. For example, it is known that neuropilins form spontaneous complexes with several members of the plexin receptor family. Accordingly, selection of the semaphorin may also be effected based on the expression pattern of both the neuropilin receptor and the plexin receptor.

The present inventors have also found that an additional method for selecting a semaphorin for treating a cancer. Semaphorins that were shown to inhibit the anchorage independent growth of a particular tumor cell were also shown to be effective at inhibiting tumor formation. A method of measuring anchorage independent growth of tumor cells is described in the Materials and Methods section of the Examples herein below involving measurement of colonies in soft agar.

It will be appreciated that the agents used for detecting semaphorin receptor expression may be provided as a kit, such as an FDA-approved kit, which may contain one or more unit dosage form containing the active agent (e.g. antibody or probe capable of specifically interacting with a semaphorin subtype). The kit may also comprise other agents useful for analyzing semaphorin receptor expression (e.g. suitable buffers, control antibodies or probes). In addition, the kit may comprise agents used for measuring tumor colonies in soft agar.

The kit may be accompanied by instructions for administration. The kit may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration.

Following selection, treatment of the cancer may be initiated by contacting (either in vivo or ex vivo) the cancer cells with an agent capable of upregulating the appropriate semaphorin.

Accordingly, the present invention contemplates administration of therapeutically effective amounts of semaphorins themselves, or administration of polynucleotides encoding the semaphorins (i.e. gene therapy) to subjects in need thereof in order to treat cancer.

The semaphorins polypeptides may comprise the full length sequences of those set forth in SEQ ID NOs: 26-32. Alternatively the semaphorins may be homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to semaphorin sequences listed herein above as determined using BlastP software of the National Center of Biotechnology Information (NCBI) using default parameters) comprising semaphorin activity. The homolog may also refer to a deletion, insertion, or substitution variant, including an amino acid substitution, thereof and biologically active polypeptide fragments thereof.

The term "polypeptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |

TABLE 2-continued

| Non-conventional amino acid | Code |
|---|---|
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchex |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α thylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchex |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α ethylhistidine | Mhis |
| L-α thylisoleucine | Mile |
| L-α-methylleucine | Mleu |
| L-α-methylmethionine | Mmet |
| L-α-methylnorvaline | Mnva |
| L-α-methylphenylalaine | Mphe |
| L-α-methylserine | mser |
| L-α ethylvaline | Mtrp |
| L-α-methylleucine | Mvalnbhm |
| N-(N-(2,2-diphenylethyl) carbamylmethyl-glycine | Nnbhm |
| 1-carboxy-1-(2,2-diphenylhylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α ethylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |

TABLE 2-continued

| Non-conventional amino acid | Code |
|---|---|
| D-N-methylserine | Dnmser |
| D-N-methylthreonine | Dnmthr |
| N-(1-methylethyl)glycine | Nval |
| N-methyla-naphthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

As mentioned herein above, the semaphorin of the present invention may comprise a conservative or non-conservative substitution.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having semaphorin-like properties.

As mentioned, the semaphorins of the present invention may comprise substitutions. According to one embodiment, the semaphorin may be engineered to resist cleavage by furin-like pro-protein convertases. Thus, for example the pro-protein convertase recognition sequence RFRR (SEQ ID NO: 39) may be mutated into the sequence KFKK (SEQ ID NO: 40). This has been effected for semaphorin-3B, where the authors showed that this mutation conferred partial resistance to pro-protein convertases of cancer cells without affecting the biological activity of full length semaphorin-3B [Varshaysky A, Kessler O, Abramovitch S, Kigel B, Zaffryar S, et al (2008) Cancer Res 68:6922-6931]. Exemplary polypeptide and polynucleotide sequences of semaphorins that are at least partially resistant to pro-protein convertase are set forth in SEQ ID NOs: 33-38.

As mentioned, the N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl) (ethyl), —NH(benzyl), —N(C1-C4 alkyl)(benzyl), —NH(phenyl), —N(C1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

The sempahorins of the present invention may also comprise non-amino acid moieties, such as for example, hydrophobic moieties (various linear, branched, cyclic, polycyclic or hetrocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the sempahorins of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the semaphorins of the invention to other non-amino acid agents may be by covalent linking, by non-covalent complexion, for example, by complexion to a hydrophobic polymer, which can be degraded or cleaved producing a compound capable of sustained release; by entrapping the amino acid part of the semaphorin in liposomes or micelles to produce the final semaphorin of the invention. The association may be by the entrapment of the amino acid sequence within the other component (liposome, micelle) or the impregnation of the amino acid sequence within a polymer to produce the final peptide of the invention.

The semaphorins of the present invention can be biochemically synthesized such as by using standard solid phase techniques. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Polypeptide Syntheses (2nd Ed., Pierce Chemical Company, 1984).

Recombinant techniques may also be used to generate the semaphorins of the present invention. These techniques may be preferred due to the number of amino acids in a semaphorin polypeptide and the large amounts required thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce an expression vector for the expression of the semaphorins of the present invention, a polynucleotide encoding the semaphorins of the present invention are ligated into a nucleic acid expression vector, which comprises the polynucleotide sequence under the transcriptional control of a cis-regulatory sequence (e.g., promoter sequence) suitable for directing constitutive, tissue specific or inducible transcription of the semaphorins of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the semaphorin of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant semaphorin. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

A variety of prokaryotic or eukaryotic cells can be used as host-expression systems to express the semaphorins of the present invention. These include, but are not limited to, microorganisms, such as bacteria transformed with a recombinant bacteriophage DNA, plasmid DNA or cosmid DNA expression vector containing the semaphorin coding sequence; yeast transformed with recombinant yeast expression vectors containing the semaphorin coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the semaphorin coding sequence.

Other than containing the necessary elements for the transcription and translation of the inserted coding sequence (encoding the semaphorin), the expression construct of the present invention can also include sequences engineered to optimize stability, production, purification, yield or activity of the expressed semaphorin.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant peptide. Effective culture conditions include, but are not limited to, effective media, bioreactor, temperature, pH and oxygen conditions that permit protein production. An effective medium refers to any medium in which a cell is cultured to produce the recombinant semaphorin of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant semaphorins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant semaphorin is effected.

The phrase "recovering the recombinant semaphorin" used herein refers to collecting the whole fermentation medium containing the semaphorin and need not imply additional steps of separation or purification.

Thus, the semaphorins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode a semaphorin fused to a cleavable moiety. Such a fusion protein can be designed so that the semaphorin can be readily isolated by affinity chromatography; e.g., by immobilization on a column specific for the cleavable moiety. Where a cleavage site is engineered between the semaphorin and the cleavable moiety, the semaphorin can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The semaphorin of the present invention is preferably retrieved in "substantially pure" form.

As used herein, the phrase "substantially pure" refers to a purity that allows for the effective use of the semaphorin in the applications described herein.

In addition to being synthesizable in host cells, the semaphorin of the present invention can also be synthesized using in vitro expression systems. These methods are well known in the art and the components of the system are commercially available.

As mentioned, the semaphorin may be administered to the subject in need thereof as polynucleotides where they are expressed in vivo i.e. gene therapy.

The phrase "gene therapy" as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject rather the genetic material to be transferred is introduced into the cells of the recipient organism in situ, that is within the recipient. These genetically altered cells have been shown to express the transfected genetic material in situ.

To confer specificity, preferably the nucleic acid constructs used to express the semaphorins of the present invention comprise cell-specific promoter sequence elements.

Recombinant viral vectors are useful for in vivo expression of the semaphorins of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

The present inventors have shown that as well as having a direct effect on tumor cells, semaphorins also affect angiogenesis by interacting with receptors on endothelial cells.

Thus, as well as treating cancer, the semaphorins of the present invention may also treat other angiogenesis related disorders.

Angiogenesis-related diseases include, but are not limited to, inflammatory, autoimmune, and infectious diseases;

angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; eczema; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. In addition, compositions of this invention can be used to treat diseases such as, but not limited to, intestinal adhesions, atherosclerosis, scleroderma, warts, and hypertrophic scars (i.e., keloids). Compositions of this invention may also be useful in the treatment of diseases that have angiogenesis as a pathologic consequence such as cat scratch disease (Rochele minalia quintosa), ulcers (*Helobacter pylori*), tuberculosis, and leprosy.

The semaphorins or polynucleotides encoding same may be administered to a subject per se or they may be part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the semaphorin accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (semaphorins) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Class-3 Semaphorins Inhibit the Development of Breast Cancer Derived Tumors by Targeting Receptor Expressing Tumor Cells Materials and Methods Materials:

Antibodies directed against β-actin, and against the myc and FLAG epitope tags as well as chemicals were from Sigma (St. Louis, Mich.). Media and sera for cell culture were from Biological-Industries Inc. (Kibbutz Beth-Haemek, Israel). Fugene-6 was obtained from Roche Ltd (Switzerland). Antibodies directed against np1 and np2 were purchased from Santa-Cruz inc. (San-Diego, Calif.). The cDNAs encoding different semaphorins were cloned to the NSPI-CMV-MCS-myc-His lentiviral expression vector containing SV40 promoter driving Puromycin selection marker. Antibodies directed against CD-31 were from BD biosciences Pharmingen. The PerfectPure RNA reverse PCR kit was from 5-Prime (Gaithersburg, Md.).

Expression Plasmids:

The cDNAs of sema3A, sema3F and sema3E were subcloned into the NSPI-CMV-myc-his lentiviral expression vector. The sema3G cDNA was cloned from HUVEC mRNA using RT-PCR. The sema3D cDNA was cloned using RT-PCR from HUVEC cells treated with 30 ng/ml of VEGF for 6 hours. The cDNAs encoding sema3D and sema3G were also subcloned into the NSPI expression vector. cDNA's containing the myc epitope tag were added in frame upstream to the stop codon of sema3D, sema3E, sema3F and sema3G. A FLAG epitope tag was added upstream to the stop codon of sema3A as described [Guttman-Raviv et al., 2007, J. Biol. Chem. 282:26294-26305].

Generation of Recombinant Lentiviruses and Letiviral Mediated Infection of Cells:

HEK293-T cells were seeded in 100 mm tissue culture dishes ($2.5 \times 10^6$ cells per dish). A day after seeding, the cells were co-transfected with the appropriate lentiviral expression plasmid (8 μg), with the packaging vector pCMVdR8.91 (5 μg), and with a plasmid encoding the vesicular stomatitis virus coat envelope pMD2-VSVG (2 μg) using Fugene-6 according to the instructions of the vendor. Conditioned medium containing infective lentiviral particles was collected 48 hours and 72 hours post transfection. Polybrene (8 μg/ml) was added to the conditioned medium and incubated 8 hours with the target cells.

Cell Lines:

Mycoplasma free MDA-MB-231, MDA-MB-435, MDA-MB-468 and MCF7 breast cancer derived cells were obtained from the ATCC. The cells were cultured in DMEM containing 4.5 mg/ml glucose supplemented with 10% FCS and antibiotics. HUVEC, PAE, HEK293 and HEK293-T cells were cultured as previously described [Kessler O. et al, 2004, Cancer Res. 64:1008-1015]. HUVEC were used between passages 3-7.

In-Vivo Tumor Formation Assays:

Cells expressing semaphorins or control cells infected with empty lentiviral vectors were implanted ($5 \times 10^6$/mouse) into the mammary fat pads of 4-6 week old balb\c nu/nu female mice (Harlan laboratories). In most experiments we groups of 9 animals/experiment were used. The tumors were measured twice a week using a caliper. The tumor volume (V) was determined using the formula, $V=0.52 \times A^2 \times B$ in which A is the short diameter and B is the long one. When MDA-MB-231 tumors reached an average volume of 200-300 mm$^3$, they were excised and weighted. Each experiment was repeated at least twice to confirm the results. Estrogen pellets were used in experiments in which the development of tumors from MCF-7 cells was determined as previously described [Akiri G et al., 2003, Cancer Res. 63:1657-1666].

Immunohistochemistry:

Tumors were embedded in OCT and frozen in 2-methylbutane cooled by liquid nitrogen. They were then sectioned into 30 μm thick sections using a cryostat. Sections were blocked with cold acetone, and reacted with an antibody directed against the endothelial marker CD-31, counterstained with hematoxilin and photographed. Eight different microscopic fields derived from different sections of three different tumors were photographed. These photographs were taken from areas in which the density of blood vessels was highest (hot spot method) [Vermeulen, P. B., 1996, Eur. J. Cancer 32A: 2474-2484]. The area of the blood vessels in fields of equal area was quantified using the Image Pro Plus software.

Western Blots:

Cell lysates were prepared and the concentration of protein determined as previously described [Guttman-Raviv, 2007, J. Biol. Chem. 282:26294-26305]. In order to determine the concentration of secreted sema3s in conditioned mediums of the various cell lines, cells were seeded in 12 well dishes at a concentration of $2 \times 10^5$ cells/well. The cells were incubated for 48 hours in 0.4 ml of serum-free medium. Aliquots of equal volume were analyzed by western blot analysis for the presence of sema3s using antibodies directed against the appropriate myc or FLAG epitope tags as previously described [Guttman-Raviv, 2007, J. Biol. Chem. 282:26294-26305]. None of the expressed semaphorins affected the proliferation rate or the survival of the various cell lines (data not shown).

Proliferation Assay:

Tumor cells ($10^4$ cells/well) were seeded in triplicate in 24 well dishes. Adherent cells were trypsinized and counted every 24 hours for 4 days, using a coulter counter. The data was plotted on a semi-log graph in which the slope of the graph represents the growth rate of the cell line.

Adhesion Assay:

In cell adhesion experiments uncoated 12 well cell culture dishes were used as well as non-adhesive 12 well dishes coated with fibronectin (5 μl/ml). Tumor cells ($10^5$ cells/well) were seeded in triplicates in growth media. The cells were washed twice with PBS, trypsinized to release adherent cells, and counted with a coulter counter. The cells were counted 5, 10, 20 and 45 minutes after they were seeded. The percentage of adherent cells relative to the number of seeded cells was then calculated and plotted. The time required for the adherence of 50% of the seeded cells was used as a measure to compare the adhesive properties of control cells and of the semaphorin expressing cells.

Endothelial Cells Repulsion Assay:

Cell repulsion assays were performed essentially as described [Guttman-Raviv, 2007, J. Biol. Chem. 282:26294-26305].

Soft-Agar Colony Formation Assay:

A first layer of agar containing 2 ml of 0.5% low melting agar (Bio-Rad) dissolved in growth media was poured into the wells of a 6 well cell culture dish and allowed to polymerize at 4° C. for 20 minutes. A second layer (1 ml) containing 0.3% of low melting agar dissolved on growth media containing cells ($3 \times 10^3$/ml) was placed on top of the first layer and allowed to set at 4° C. for 20 minutes. Growth medium (2 ml) was added on top of the second layer and the cells were incubated in a humidified incubator at 37° C. for 21 days with a twice a week change of medium. At the end of the experiment, colonies were stained for 1 hour with 0.005% crystal violet, and incubated with PBS overnight to remove excess crystal violet. The colonies were photographed and colonies with a diameter of 150 μm or more were counted using the Image-pro morphometric software.

Statistical Analysis:

Statistical analysis was performed using the upaired data with unequal variance student's T-test. Error bars represent the standard error of the mean. Statistical significance is presented in the following manner: *p<0.05, p<0.01 and *p<0.001.

Results

Expression Patterns of Class-3 Semaphorin Receptors in Breast Cancer Derived Cell Lines:

Semaphorins may affect the development of tumors by several mechanisms which include direct effects on the tumor cells, effects on angiogenesis and effects on stromal cells. In order to find out if the class-3 semaphorins sema3A, sema3D, sema3E, sema3F and sema3G can influence the formation of tumors from breast cancer cells by directly influencing tumor cell behavior, the present inventors first determined the expression patterns of known sema3s receptors in the cells. The different types of breast cancer derived cells differed in their expression of sema3 receptors. MDA-MB-231 cells express predominantly np1, a receptor for sema3A and sema3D, but very little np2 if at all. MDA-MB-435 cells on the other hand express predominantly np2, a receptor for sema3F and sema3G and very little if any np1. MCF-7 cells express np1 (although at lower levels as compared to the MDA-MB-231 cells) and do not express np2 (FIG. 1A).

Because of their short intracellular domains the neuropilins cannot transduce sema3 signals on their own and form complexes with plexins in which the plexins serve as the signal transducing elements. All four cell lines expressed plexA1 and all but the MDA-MB-468 cells also expressed plexA2. However, none of the breast cancer derived cell lines expressed plexA4 and only the MCF-7 cells expressed low levels of plexA3 (FIGS. 1B-C). The mRNA encoding sema3E receptor PlexD1 was expressed in MDA-MB-231 and MCF-7 while MDA-MB-435 cells expressed lower concentrations and MDA-MB-468 cells did not express at all (FIGS. 1B-C).

The Effects of Different Sema3s on the Development of Tumors from MDA-MB-231, MDA-MB-435, MDA-MB-468 and MCF-7 Breast Cancer Cells:

In order to determine the effects of sema3A, sema3D, sema3E, sema3F and sema3G in the breast cancer cell lines, the full length cDNAs encoding the five semaphorins (or a control of empty expression vector) were expressed in the cells using lentiviral vectors carrying a selection marker that conveys resistance to puromycin. Pools of infected cells were selected and examined for semaphorin expression by western blot analysis using antibodies directed against epitope tags incorporated into the recombinant semaphorins. Sema3s contain conserved cleavage sites for furin like pro-protein convertases and in the case of sema3E the cleaved product possess pro-metastatic properties. However, there was only minimal cleavage of any of the recombinant semaphorins in MDA-MB-231 cells or in the MDA-MB-435 cells (data not shown). The MDA-MB-231 cells were subsequently implanted in the mammary fat pads of immune deficient mice, and allowed to develop into tumors. In the case of the MDA-MB-231 cells, all the semaphorins that were tested were efficiently expressed (FIGS. 2A, D, G and J). Expression of the np1 agonist sema3A inhibited almost completely the development of tumors from these cells (FIGS. 2B-C). Sema3D is an agonist for np1 and for np2. Sema3D inhibited tumor formation completely in one experiment (data not shown) and in another experiment inhibited strongly though not completely the development of tumors (FIGS. 2E-F). In contrast, the np2 agonist sema3G was not able to inhibit the development of tumors from MDA-MB-231 cells (FIGS. 2K-L). Expression of the np2 agonist sema3F on the other hand, inhibited significantly the development of tumors from these cells despite the lack of np2 receptors. The tumors that developed from the sema3F expressing MDA-MB-231 cells (FIG. 2C) appeared much less bloody than the control tumors suggesting that sema3F inhibited tumor angiogenesis (FIG. 2A). Expression of the PlexD1 agonist sema3E also inhibited significantly the development of tumors from MDA-MB-231 cells but the resulting tumors did not look starved of blood vessels (FIG. 2G-I).

Figure 3E:
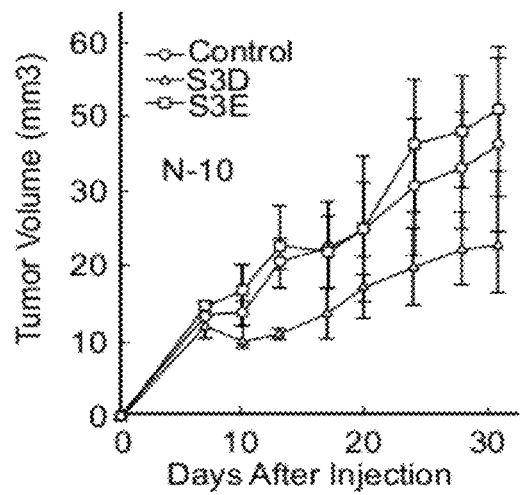
Figure 3F:
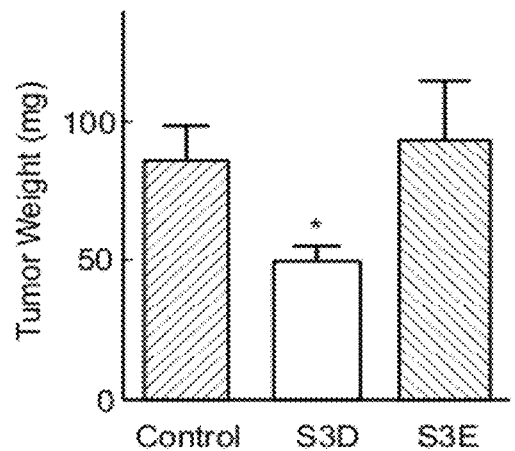
Figure 3G:
Figure 3H:
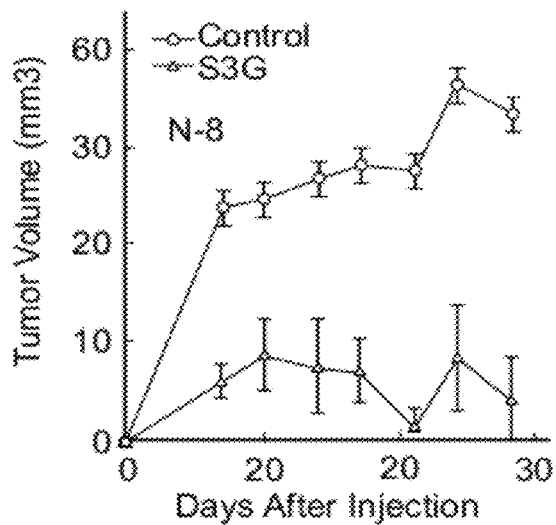
Figure 3I:
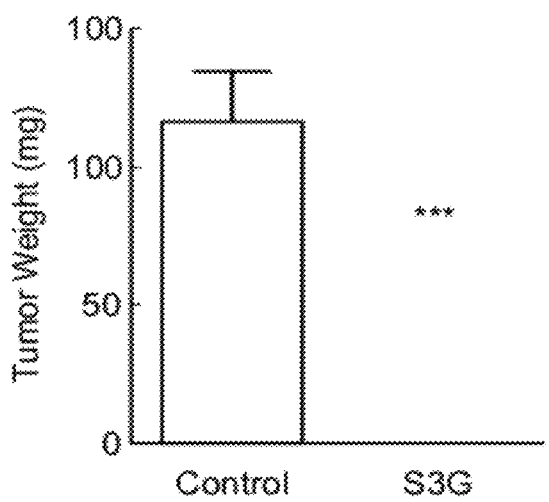

A different picture emerges when the effects of these semaphorins on the development of tumors from np2 expressing MDA-MB-435 cells are examined. When control cells are injected into the mammary fat pads of nu/nu balb/c mice they develop into small tumors that stop growing when they reach an average volume of 50-100 mm$^3$ (FIGS. 3B, E and H). In contrast, there is no such limitation on the development of tumors from any of the other breast cancer derived cell lines used in this study. Expression of the np2 agonist sema3F inhibited significantly the development of tumors from these cells (FIGS. 3B and C) and the np2 agonist sema3G was an even stronger inhibitor (FIGS. 3H-I). In contrast, expression of the np1 specific sema3A did not inhibit the development of tumors from these cells (FIGS. 3B-C), while sema3D, a semaphorin that binds to both neuropilins, also inhibited their development significantly but less potently than sema3G (FIGS. 3E-F). MDA-MB-435 cells also express the sema3E receptor PlexD1, although at a lower expression levels than those found in MDA-MB-231 cells (FIGS. 1A-B). Expression of sema3E did not inhibit the formation of tumors from the MDA-MB-435 cells. This was not due to cleavage by furin like pro-protein convertases since less than 5% of the sema3E found in the conditioned medium of these cells was cleaved (data not shown).

The present inventors also determined how the expression of sema3A and sema3F, the best studied np1 and np2 agonists respectively, affects the development of tumors from non-metastatic, estrogen dependent MCF-7 cells which express predominantly np1. Expression of sema3A inhibited significantly though not completely the development of tumors from these cells while sema3F did not (FIGS. 4A-C). These effects are similar to those observed with regard to the effect of these semaphorins on the development of tumors from MDA-MB-231 cells (FIGS. 2A and 2C). Taken together, these results suggest that sema3s ability to inhibit tumor formation from a given breast cancer derived cell type depends on the identity of the semaphorin receptors expressed by the cells of the developing tumor, and further suggest that sema3s should not be able to inhibit the formation of tumors from breast cancer cells that do not express sema3 receptors.

Figure 4E:
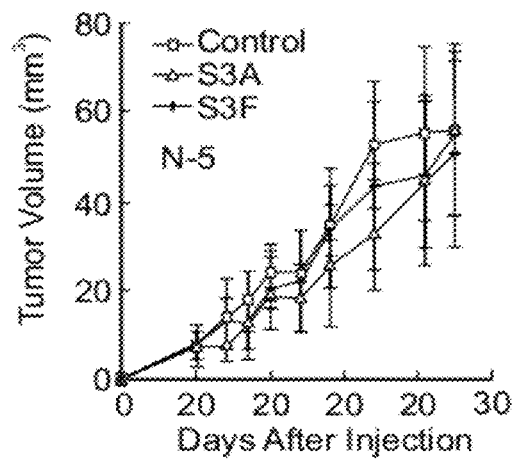
Figure 4F:
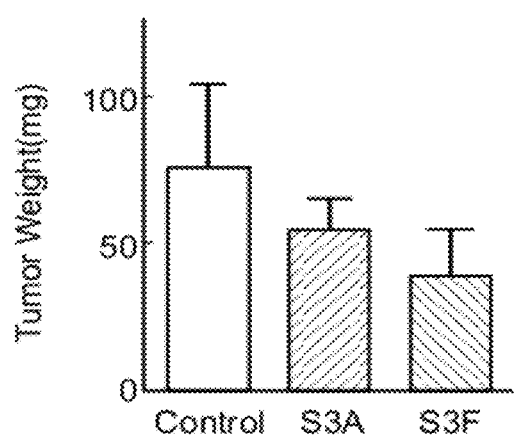

To put this prediction to the test, sema3A and sema3F were expressed in MDA-MB-468 breast cancer cells, which do not express np1, np2 or PlexD1 (FIGS. 1A, C). These cells form slowly growing tumors upon injection into the mammary fat pads of nu/nu balb/c mice. In agreement with the present prediction, neither the expression of sema3A nor expression of sema3F significantly inhibited the formation of tumors from these cells (FIGS. 4E-F).

The Effects of Different Class-3 Semaphorins on Tumor Angiogenesis:

Sema3F was characterized in several studies as an inhibitor of tumor angiogenesis and as a repulsive factor for endothelial cells and sema3A was also found to function as an inhibitor of VEGF induced angiogenesis and as a repulsive factor for endothelial cells although not as an inhibitor of tumor angiogenesis. To compare the repulsive properties of the different class-3 semaphorins HEK293 cells expressing similar levels of semaphorins were seeded on top of monolayers of human umbilical vein derived endothelial (HUVEC) cells at clonal densities. The HEK293 cells secreted similar concentrations of semaphorin into their growth media as determined by western blot analysis using antibodies directed against myc epitope tags that were fused in frame before the stop codon of the cDNAs of the different semaphorins (data not shown). Control cells infected with the empty lentiviral vector did not repel the endothelial cells but sema3A, sema3D and sema3E expressing cells repelled the endothelial cells efficiently (FIG. 5A). However, the np2 agonists sema3F and in particular sema3G repelled HUVEC less potently than the np1 agonists or the PlexD1 agonist sema3E (data not shown). Therefore cells expressing either sema3F or sema3G were seeded on top of porcine aortic endothelial (PAE) cells engineered to co-express np2 and plexA1. These cells were repelled very strongly by sema3F as expected but were still repelled rather inefficiently by sema3G (FIG. 5B).

In order to find out if the various sema3s that were examined in the present example inhibit tumor angiogenesis, the concentration of blood vessels in tumors that developed from control and semaphorin expressing breast cancer derived cells was determined. Since sema3A inhibited tumor formation in MDA-MB-231 cell almost completely it was not possible to determine the concentration of blood vessels in this case. However, expression of the np1 agonist sema3D in this cell type resulted in the formation of tumors containing significantly lower concentrations of blood vessels than in tumors that developed from control cells (FIG. 5C). The reduction in the concentration of tumor associated blood vessels was not correlated with the types of semaphorin receptors expressed by the cancer cells since expression of the np2 agonists sema3F and sema3G also reduced significantly the concentration of tumor associated blood vessels in tumors developing from MDA-MB-231 cells (FIG. 5C). Quantitatively, a similar reduction in the concentration of tumor associated blood vessels was observed regardless of whether sema3D or sema3G were used, even though sema3D expression inhibited tumor formation efficiently while sema3G did not inhibit tumor formation (FIGS. 2A-L). In-contrast, expression of sema3E, a semaphorin which inhibited the development of tumors from MDA-MB-231 cells (FIGS. 2G-I) and which inhibits the invasion of blood vessels into somites during early development, did not result in a decrease in the concentration of tumor associated blood vessels in MDA-MB-231 derived tumors (FIG. 5C).

The effects of sema3A and sema3F expression on the concentration of tumor associated blood vessels in MCF-7 cells were also examined. These tumors develop in the mammary fat pads of the mice only in the presence of slow estrogen release pellets. Expression of sema3A in these cells consistently and significantly reduced the concentration of tumor associated blood vessels. However, expression of sema3F did not (FIG. 5D).

In the case of the tumors that developed from the MDA-MB-435 cells, the expression of sema3A and sema3D was found to strongly reduce the concentration of blood vessels in resulting tumors (FIG. 5E) even though tumor development from these cells was not inhibited by these semaphorins (FIGS. 3A-I). It was not possible to determine the blood vessel concentration in tumors that developed from cells expressing sema3F or sema3G since the resulting tumors were too small or non-existent as in the case of sema3G. Expression of sema3E did produce a decrease in the concentration of blood vessels in tumors developing from these cells, but the decrease, although statistically significant, was small.

Taken together, these experiments indicate that although most of the semaphorins are able to inhibit angiogenesis, as manifested by the reduction in the concentration of blood vessels in tumors, and even though the inhibition may contribute to the inhibition of tumor progression, there was generally no correlation between this ability and the inhibition of tumor development which was mostly correlated with the expression of the appropriate semaphorin receptors by the tumor cells.

The Effects of the Expression of Different Class-3 Semaphorins on the Behavior of the Tumor Cells In-Vitro:

The experiments described hereinabove suggest that semaphorin expression may strongly modulate the behavior of tumor cells. Indeed, other researchers have described effects of various class-3 semaphorins on the adhesion, spreading and proliferation of various types of tumor cells [Tomizawa, Y., et al., 2001, Proc. Natl. Acad. Sci. U.S.A 98:13954-13959; Bielenberg, D. R., et al., 2004, J. Clin. Invest 114:1260-1271; Nasarre, P et al., 2005, Neoplasia. 7:180-189]. However, the proliferation of MDA-MB-231 cells expressing either sema3A, sema3F, sema3D or sema3E was not inhibited as compared to control cells infected with empty vector containing lentiviruses. Similarly, the proliferation of MCF-7 cells expressing either sema3A or sema3F was not altered as compared to controls and MDA-MB-435 cells expressing sema3A or sema3F were also not affected as compared to control cells (data not shown). These results indicate that the effect that these semaphorins have on the growth of tumors in-vivo are probably not mediated by a direct effect on the proliferation machinery of the tumor cells. The effect of the expression of different semaphorins on the adhesion of the various tumor cells to plastic or to fibronectin was also examined. Neither sema3A nor sema3F expression affected the rate or extent of adhesion of MDA-MB-231, MDA-MB-435 or MCF-7 cells regardless of whether the substrate was plastic or fibronectin (data not shown).

The ability to form colonies in soft-agar is a hallmark that differentiates many types of cancer cells from their normal counterparts. Therefore, the present inventors determined whether the expression of different class-3 semaphorins in MDA-MB-231 or MDA-MB-435 cells affects their ability to form colonies in soft-agar. None of the semaphorins inhibited completely the formation of colonies by MDA-MB-231 cells. However, both sema3A and sema3D, semaphorins that strongly inhibit tumor formation from these cells (FIGS. 2A-L), also significantly inhibited the formation of large colonies in soft agar (FIGS. 6A-B). Surprisingly, sema3F also inhibited significantly the formation of large colonies in soft agar despite the absence of np2 receptors on these cells. However, sema3F does bind to np1, albeit with a 10 fold lower affinity, and it is possible that this inhibitory effect is mediated by np1. Another np2 agonist, sema3G, which in contrast to sema3F does not inhibit the development of tumors from MDA-MB-231 cells at all (FIGS. 2J-L) and does not bind to np1, had no effect on the development of colonies in soft agar (FIGS. 6A-B). These results suggested that the semaphorin needs to bind to the semaphorin receptor expressed by the tumor cells in order to be able to inhibit soft-agar colony formation. MDA-MB-231 cells also express the sema3E receptor PlexD1 and expression of sema3E inhibits the formation of tumor formation from these cells (FIGS. 2G-I). However, sema3E failed to inhibit the formation of large colonies of MDA-MB-231 cells in soft-agar (FIGS. 6A-B).

Based on these results the present inventors predicted that sema3D, sema3F and sema3G, which inhibit tumor formation from MDA-MB-435 cells (FIGS. 3A-I), should also inhibit efficiently the formation of soft-agar colonies from these np2 expressing cells. Indeed, sema3d and sema3G inhibited colony formation efficiently as predicted. However, unexpectedly it was found that sema3F inhibited the formation of colonies in soft agar from these cells even though it did not inhibit the formation of tumors from these cells (FIGS. 6C-D). Another unexpected observation was that sema3E, which did not inhibit the formation of tumors from these cells did inhibit colony formation (FIGS. 6C-D). Lastly, it was expected that sema3A would not affect colony formation since its receptor is not expressed by MDA-MB-435 cells (FIGS. 10A-C). Indeed, colony formation from MDA-MB-435 cells was not inhibited by sema3A. Instead it was even enhanced (FIGS. 6C-D).

Taken together these results suggest that the different semaphorins are able to modulate the behavior of MDA-MB-231 and MDA-MB-435 cells directly, although there were exceptions to this rule.

Figure 7D:
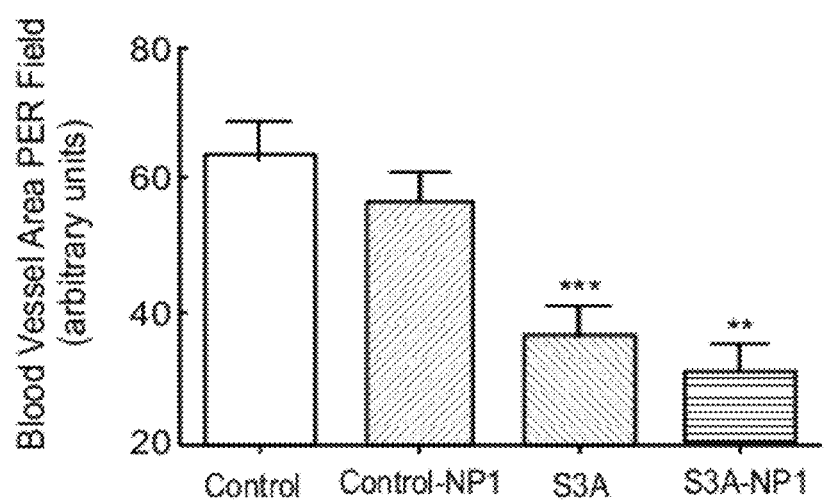

Expression of np1 in MDA-MB-435 Cells Enhances Tumor Development and the Enhancement is Negated by Co-Expression of Sema3a:

The experiments described above suggest that the expression of specific class-3 semaphorin receptors by breast cancer derived tumor cells is probably the most important factor that determines whether a given class-3 semaphorin will be an effective inhibitor of tumor development. To test this hypothesis the present inventors asked whether expression of np1 in MDA-MB-435 cells would render tumors that will develop from these cells sensitive to sema3A. Tumors that developed from MDA-MB-435 cells that express np1 did not stop developing when they reached a mean volume of 50-100 mm$^3$ like wild-type MDA-MB-435 cells (FIGS. 3A-I). The np1 expressing MDA-MB-435 cells formed rapidly forming tumors when implanted in the mammary fat pads of mice (FIGS. 7A-C). Even though these np1 expressing cells formed tumors that appeared bloody, the concentration of blood vessels within these tumors, as determined by staining with an antibody directed against CD-31, was not significantly different from that of control tumors (FIG. 7D). When the np1 agonist sema3A was co-expressed in these cells with np1, the cells that expressed both genes reverted to the behavior exhibited by the parental cells and formed tumors that stopped growing when the tumors reached a volume of 50-100 mm$^3$ thereby eliminating the growth advantage conferred by the presence of np1 (FIGS. 7A-C), but not that conferred by the presence of np2 which can be inhibited by np2 agonists such as sema3F or sema3G (FIGS. 3A-I). Interestingly, the density of blood vessels in tumors that developed from MDA-MB-435 cells expressing sema3A or sema3A+np1 was similar and significantly lower than in tumors that developed from MDA-MB-435 cells that do not express sema3A (FIG. 7D), suggesting once again that inhibition of angiogenesis represents part of the mechanism by which semaphorins modulate tumor progression, but that it may not always be sufficient to inhibit tumor expansion.

Discussion

The present results indicate for the first time that sema3A, sema3D, sema3E and sema3G inhibit the formation of tumors from several cell lines derived from human breast carcinomas. It should be noted that sema3E was previously described as a pro-metastatic agent, but the pro-metastatic activity was associated with a cleavage product generated by furin like pro-protein convertases and not by the full length protein. In the present experiments there was almost no cleavage of sema3E in the MDA-MB-231 cells or MDA-MB-435 cells.

Many types of tumorigenic cells express one or more than one of the class-3 semaphorin receptors np1, np2 or PlexD1. The breast cancer derived cell types that were employed in the present examples in order to study the anti-tumorigenic effects of the different semaphorins, express different combinations of class-3 semaphorin receptors on their cell surfaces. Both neuropilins as well as several types of plexins are also expressed in endothelial cells in which they play an important role in the transduction of VEGF induced angiogenic signals, and mediate the anti-angiogenic effects of sema3s. In the present study the present inventors have tried to evaluate the relative importance of the anti-angiogenic effects versus the direct effects of the sema3s in the determination of the anti-tumorigenic properties of different sema3s. Taken together, the present examples indicate that the expression of a given semaphorin receptor by the tumorigenic cells is probably the most important factor which determines whether a given class-3 semaphorin will function as an effective inhibitor of tumor development. Thus, the development of tumors from MDA-MB-231 cells that express np1 but not np2 is strongly inhibited by the np1 agonists sema3A and sema3D but not by the np2 agonist sema3G. This conclusion is also supported by experiments which have shown that in the case of the np2 expressing MDA-MB-435 cells sema3A does not inhibit tumor development and sema3D inhibits tumor development weakly while sema3G and sema3F function in the case of these cells as very effective inhibitors. Furthermore, neither sema3A nor sema3F were able to inhibit the development of tumors from MDA-MB-468 cell that do not express neuropilins.

Sema3E is unique among sema3s as it is the only semaphorin which does not bind to neuropilins and instead activates directly PlexD1. Both MDA-MB-231 and MDA-MB-435 cells express PlexD1 although the expression levels in MDA-MB-435 cells are significantly lower than in MDA-MB-231 cells. Sema3E inhibited significantly tumor development from MDA-MB-231 cells but not at all from MDA-MB-435 cells. It is possible that the levels of expression of PlexD1 in the MDA-MB-435 cells are below a critical threshold that does not enable inhibition of tumor development by sema3E. Thus, this result may perhaps also be regarded as one that supports the above mentioned rule of thumb. PlexD1 can form complexes with neuropilins, and at least in the case of np1 this interaction can affect the nature of the biological response to sema3E. It is therefore possible that in the MDA-MB-435 cells, the effect of sema3E may be inhibited by np2 while in MDA-MB-231 cells np1 may affect sema3E signaling differently, resulting in diverse biological responses.

The present inventors showed for the first time that sema3D, sema3G, sema3A and sema3E function as inhibitors of tumor angiogenesis since their expression in tumor cells resulted in a significant reduction in the density of tumor associated blood vessels. These results indicate that as a rule, semaphorin expression tends to reduce the density of blood vessels in tumors that develop from MDA-MB-231, MDA-MB-435 or MCF-7 cells even in cases in which tumor development is not inhibited by the given semaphorin. However, there were a few exceptions to this rule. The density of blood vessels in tumors derived from sema3F expressing MCF-7 cells was not reduced in comparison with tumors derived from control MCF-7 cells. However, the development of tumors from MCF-7 cells requires estrogen, a hormone that was recently found to inhibit the expression of the sema3F receptor np2, which may perhaps explain the lack of the anti-angiogenic effect in this case. In addition it was found that expression of sema3E in MDA-MB-231 cells also failed to reduce the density of blood vessels in resulting tumors in spite of significant inhibition of tumor growth.

The density of tumor associated blood vessels is determined by a balance between the rate of tumor angiogenesis, which tends to increase blood vessel density, and the rate of tumor cell proliferation which tends to decrease it. It is therefore possible that a small tumor whose expansion was strongly inhibited by an anti-angiogenic agent will contain the same density of blood vessels as a tumor whose expansion was much less affected by the anti-angiogenic agent, simply because in the latter case the reduction in the density of blood vessels did not reach that threshold below which the expansion of the tumor mass is inhibited. It was observed that in most cases the expression of class-3 semaphorins by the tumor cells reduces the density of blood vessels in resulting tumors, regardless of the receptor types with which the specific semaphorins interact and regardless of whether the sema3s were able to inhibit the development of the tumors. For example, sema3G decreased significantly the density of blood vessels in tumors derived from MDA-MB-231 cells as did sema3D and sema3F even though in contrast with these semaphorins sema3G did not inhibit tumor development.

The present inventors reasoned that if the expression of semaphorin receptors by the tumor cells is the primary factor that determines whether sema3s will be able to inhibit tumor development, than the expression of semaphorins should affect the behavior of such tumor cells in in-vitro assays too. Class-3 semaphorins such as sema3F and sema3B inhibit the adhesion and migration of some tumor cells. It was therefore surprising that neither the proliferation, nor the adhesive properties of the different tumor cells used in this study were modified the expression of the different semaphorins. So far, the only property of the tumor cells which was found to be affected by the expression of semaphorins was their ability to form colonies in soft-agar. In general, semaphorins that inhibited the formation of tumors from either MDA-MB-231 or MDA-MB-435 cells were also able to inhibit the anchorage independent growth of the tumor cells. Anchorage independent growth is a hallmark of most malignant cells and these observations indicate that the sema3s directly influence a tumor cell characteristic that is correlated with their malignant properties. However, a few exceptions to this rule were also noticed. Expression of sema3E in MDA-MB-231 cells did not inhibit the anchorage free growth of the cells even though the formation of tumors from these cells was inhibited. Another discrepancy was noted in the case of sema3F, which when expressed in MDA-MB-435 cells inhibited strongly tumor formation but not the anchorage free growth of these cells. The reason for these discrepancies is still under investigation, but nevertheless, in general there is good agreement between the effects of the sema3s on the development of the tumors and their ability to inhibit anchorage free growth.

In conclusion, the present inventors have found for the first time that sema3A, sema3D, sema3E and sema3G possess anti-tumorigenic properties similar to those displayed by the previously identified tumor suppressors sema3F and sema3B. It was also found that all of these semaphorins can repulse endothelial cells with varying potencies and that all of them are able to significantly reduce the density of blood vessels in tumors that develop from tumor cells expressing these semaphorins. Sema3E was an exception since even though it functioned as a potent repulsive agent for endothelial cells in-vitro, it had no effect on the density of blood vessels in tumors that developed from MDA-MB-231 cells and only a small effect on the density of blood vessels in tumors that develop from MDA-MB-435 cells. In addition, a strong correlation between the ability to inhibit tumor growth in-vivo and the ability to inhibit anchorage independent growth in-vitro by individual semaphorins was noted. These observations lead to the conclusion that efficient inhibition of tumor development by semaphorins is enabled when an individual semaphorin is able to inhibit directly the malignant properties of the tumor cells and when this semaphorin is also able to efficiently inhibit tumor angiogenesis. The present results argue that semaphorins may find use as general anti-angiogenic agents. However, for maximal effectiveness as anti-tumorigenic agents the selection of specific semaphorins or semaphorin combinations will have to take into account the identity of the semaphorin receptors expressed by the tumorigenic cells of target tumors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating cancer in a subject in need thereof, the method comprising administering to the subject a therapeutically effective amount Semaphorin3D (Sema3D), having an amino acid sequence at least 95% identical to the sequence as set forth in SEQ ID NO: 29 or 36, thereby treating cancer.

2. The method of claim 1, wherein said semaphorin3D is a pro-protein convertase resistant semaphorin3D.

3. The method claim 1, wherein said semaphorin comprises the amino acid sequence as set forth in SEQ ID NO: 29 or 36.

4. The method of claim 1, wherein said cancer is selected from the group consisting of breast cancer, pancreatic cancer and lung cancer.

5. The method of claim 1, wherein the cancer is associated with tumor metastasis.

6. A method of inhibiting tumor angiogenesis in a subject in need thereof comprising administering to the subject a therapeutically effective amount of Sema3D having an amino acid sequence at least 95% identical to the sequence as set forth in SEQ ID NO: 29 or 36, thereby inhibiting tumor angiogenesis.

* * * * *